US009320513B2

(12) United States Patent
Van Bladel et al.

(10) Patent No.: US 9,320,513 B2
(45) Date of Patent: Apr. 26, 2016

(54) TRANS-CATHETER VENTRICULAR RECONSTRUCTION STRUCTURES, METHODS, AND SYSTEMS FOR TREATMENT OF CONGESTIVE HEART FAILURE AND OTHER CONDITIONS

(71) Applicant: BioVentrix, Inc., San Ramon, CA (US)

(72) Inventors: Kevin Van Bladel, Livermore, CA (US); Lon Annest, New York, NY (US); Murray Sheldon, Martinez, CA (US); Ernie Heflin, Pleasanton, CA (US); Andrew Wechsler, Philadelphia, PA (US); John Stiggelbout, Sausalito, CA (US); Rovil Arcia, Fremont, CA (US); John Bower, Livermore, CA (US)

(73) Assignee: BioVentrix, Inc., San Ramon, CA (US)

( * ) Notice: Subject to any disclaimer, the term of this patent is extended or adjusted under 35 U.S.C. 154(b) by 0 days.

(21) Appl. No.: 14/657,180

(22) Filed: Mar. 13, 2015

(65) Prior Publication Data
US 2015/0282802 A1 Oct. 8, 2015

Related U.S. Application Data

(62) Division of application No. 13/632,104, filed on Sep. 30, 2012, now Pat. No. 8,979,750.

(60) Provisional application No. 61/541,624, filed on Sep. 30, 2011, provisional application No. 61/541,975, filed on Sep. 30, 2011, provisional application No. 61/541,980, filed on Sep. 30, 2011, provisional application No. 61/541,978, filed on Sep. 30, 2011.

(51) Int. Cl.
*A61B 17/00* (2006.01)
*A61B 17/04* (2006.01)
(Continued)

(52) U.S. Cl.
CPC ............ *A61B 17/0401* (2013.01); *A61B 17/00* (2013.01); *A61B 17/0057* (2013.01);
(Continued)

(58) Field of Classification Search
CPC ............... A61B 2017/3488; A61B 2017/3458; A61B 2017/306; A61B 2017/22065; A61B 2017/2038; A61B 2017/00243; A61B 2017/0409; A61B 2017/0417; A61B 17/0401; A61B 17/0057; A61B 19/22; A61B 17/0485; A61B 17/3417; A61B 17/3478; A61F 2/2487; A61M 29/02
USPC ........................................................ 600/16
See application file for complete search history.

(56) References Cited

U.S. PATENT DOCUMENTS 4,007,743 A 2/1977 Blake
5,295,958 A 3/1994 Shturman
(Continued)

FOREIGN PATENT DOCUMENTS

EP 1 078 644 A1 2/2001
EP 1 100 378 A1 5/2001
(Continued)

OTHER PUBLICATIONS

European Examination Report of EP Patent Application 05810316.9 dated Mar. 10, 2009, 6 pages.
(Continued)

*Primary Examiner* — Paula J Stice
(74) *Attorney, Agent, or Firm* — Kilpatrick Townsend & Stockton LLP

(57) ABSTRACT

Embodiments described include devices, systems, and methods for reducing the distance between two locations in tissue. An anchor may reside within the right ventricle in engagement with the septum. A tension member may extend from that anchor through the septum and an exterior wall of the left ventricle to a second anchor disposed along a surface of the heart. Perforating the exterior wall and the septum from an epicardial approach can provide control over the reshaping of the ventricular chamber. Guiding deployment of the implant from along the epicardial access path and another access path into and through the right ventricle provides control over movement of the anchor within the ventricle. The joined epicardial pathway and right atrial pathway allows the tension member to be advanced into the heart through the right atrium and pulled into engagement along the epicardial access path.

23 Claims, 52 Drawing Sheets

(51) Int. Cl.
*A61B 19/00* (2006.01)
*A61M 29/02* (2006.01)
*A61F 2/24* (2006.01)
*A61B 17/22* (2006.01)
*A61B 17/30* (2006.01)
*A61B 17/34* (2006.01)
*A61B 18/14* (2006.01)

(52) U.S. Cl.
CPC ............... *A61B19/22* (2013.01); *A61F 2/2487* (2013.01); *A61M 29/02* (2013.01); *A61B 17/0485* (2013.01); *A61B 17/3417* (2013.01); *A61B 17/3478* (2013.01); *A61B 2017/00243* (2013.01); *A61B 2017/0409* (2013.01); *A61B 2017/0417* (2013.01); *A61B 2017/22038* (2013.01); *A61B 2017/22065* (2013.01); *A61B 2017/306* (2013.01); *A61B 2017/3458* (2013.01); *A61B 2017/3488* (2013.01); *A61B 2018/1425* (2013.01)

(56) References Cited

U.S. PATENT DOCUMENTS

| | | |
|---|---|---|
| 5,830,224 A | 11/1998 | Cohn et al. |
| 5,961,440 A | 10/1999 | Schweich, Jr. et al. |
| 6,045,497 A | 4/2000 | Schweich et al. |
| 6,050,936 A | 4/2000 | Schweich, Jr. et al. |
| 6,059,715 A | 5/2000 | Schweich, Jr. et al. |
| 6,125,852 A | 10/2000 | Stevens et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,166,684 A | 12/2000 | Yoshikawa et al. |
| 6,258,021 B1 | 7/2001 | Wilk |
| 6,260,552 B1 | 7/2001 | Mortier et al. |
| 6,406,420 B1 | 6/2002 | McCarthy et al. |
| 6,494,825 B1 | 12/2002 | Talpade |
| 6,511,416 B1 | 1/2003 | Green et al. |
| 6,572,529 B2 | 6/2003 | Wilk |
| 6,616,684 B1 | 9/2003 | Vidlund et al. |
| 6,705,988 B2 | 3/2004 | Spence et al. |
| 6,709,382 B1 | 3/2004 | Horner |
| 6,746,471 B2 | 6/2004 | Mortier et al. |
| 6,776,754 B1 | 8/2004 | Wilk |
| 6,808,488 B2 | 10/2004 | Mortier |
| 6,859,662 B2 | 2/2005 | Bombardini |
| 6,890,295 B2 | 5/2005 | Michels et al. |
| 7,146,225 B2 | 12/2006 | Guenst et al. |
| 7,326,177 B2 | 2/2008 | Williamson |
| 7,390,329 B2 | 6/2008 | Westra et al. |
| 7,722,523 B2 | 5/2010 | Mortier et al. |
| 7,753,923 B2 | 7/2010 | St. Goar et al. |
| 7,766,816 B2 | 8/2010 | Chin et al. |
| 7,785,248 B2 | 8/2010 | Annest et al. |
| 8,066,766 B2 | 11/2011 | To et al. |
| 8,123,668 B2 | 2/2012 | Annest et al. |
| 8,394,008 B2 | 3/2013 | Annest et al. |
| 8,425,402 B2 | 4/2013 | Annest et al. |
| 8,449,442 B2 | 5/2013 | Annest et al. |
| 8,491,455 B2 | 7/2013 | Annest et al. |
| 8,506,474 B2 | 8/2013 | Chin et al. |
| 8,636,639 B2 | 1/2014 | Annest et al. |
| 8,979,750 B2 | 3/2015 | Van Bladel et al. |
| 2001/0041821 A1 | 11/2001 | Wilk |
| 2002/0058855 A1 | 5/2002 | Schweick, Jr. et al. |
| 2002/0077524 A1 | 6/2002 | Schweich, Jr. et al. |
| 2002/0120298 A1 | 8/2002 | Kramer et al. |
| 2002/0123768 A1 | 9/2002 | Gilkerson et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2003/0032979 A1 | 2/2003 | Mortier et al. |
| 2003/0163165 A1 | 8/2003 | Bornzin et al. |
| 2003/0166992 A1 | 9/2003 | Schweich, Jr. et al. |
| 2003/0181951 A1 | 9/2003 | Cates |
| 2003/0233022 A1 | 12/2003 | Vidlund et al. |
| 2004/0167580 A1 | 8/2004 | Mann et al. |
| 2004/0225304 A1 | 11/2004 | Vidlund et al. |
| 2005/0065506 A1 | 3/2005 | Phan |
| 2005/0096498 A1 | 5/2005 | Houser et al. |
| 2005/0137688 A1 | 6/2005 | Salahieh et al. |
| 2005/0143620 A1 | 6/2005 | Mortier et al. |
| 2005/0288613 A1 | 12/2005 | Heil, Jr. |
| 2006/0135962 A1 | 6/2006 | Kick et al. |
| 2006/0161040 A1 | 7/2006 | McCarthy et al. |
| 2006/0161238 A1 | 7/2006 | Hall |
| 2006/0200002 A1 | 9/2006 | Guenst |
| 2006/0241340 A1 | 10/2006 | Schroeder et al. |
| 2006/0247672 A1 | 11/2006 | Vidlund et al. |
| 2006/0276684 A1* | 12/2006 | Speziali ................ A61F 2/2487 600/37 |
| 2007/0010876 A1 | 1/2007 | Salahieh et al. |
| 2007/0049971 A1 | 3/2007 | Chin et al. |
| 2007/0055303 A1 | 3/2007 | Vidlund et al. |
| 2007/0073274 A1 | 3/2007 | Chin et al. |
| 2007/0112244 A1 | 5/2007 | McCarthy et al. |
| 2007/0161846 A1 | 7/2007 | Nikotic et al. |
| 2007/0203503 A1 | 8/2007 | Salahieh et al. |
| 2008/0082132 A1 | 4/2008 | Annest et al. |
| 2008/0097148 A1 | 4/2008 | Chin et al. |
| 2008/0269551 A1 | 10/2008 | Annest et al. |
| 2008/0294251 A1 | 11/2008 | Annest et al. |
| 2009/0093670 A1 | 4/2009 | Annest et al. |
| 2009/0270980 A1 | 10/2009 | Schroeder et al. |
| 2010/0010538 A1 | 1/2010 | Juravic et al. |
| 2010/0016655 A1 | 1/2010 | Annest et al. |
| 2010/0057000 A1 | 3/2010 | Melsheimer et al. |
| 2010/0268020 A1 | 10/2010 | Chin et al. |
| 2011/0087261 A1 | 4/2011 | Wittkampf et al. |
| 2011/0160750 A1 | 6/2011 | Annest et al. |
| 2012/0190958 A1 | 7/2012 | Annest et al. |
| 2013/0090523 A1 | 4/2013 | Van Bladel et al. |
| 2013/0090672 A1 | 4/2013 | Butler et al. |
| 2013/0096579 A1 | 4/2013 | Annest et al. |
| 2013/0324787 A1 | 12/2013 | Chin et al. |
| 2013/0325041 A1 | 12/2013 | Annest et al. |
| 2014/0031613 A1 | 1/2014 | Annest et al. |
| 2014/0051916 A1 | 2/2014 | Chin et al. |

FOREIGN PATENT DOCUMENTS

| | | |
|---|---|---|
| WO | 00/06028 A1 | 2/2000 |
| WO | 02/30335 A2 | 4/2002 |
| WO | 03/032818 A3 | 4/2003 |
| WO | 2005/092203 A1 | 10/2005 |
| WO | 2006/044467 A2 | 4/2006 |
| WO | 2006/105008 A2 | 10/2006 |
| WO | 2007/022519 A2 | 2/2007 |

OTHER PUBLICATIONS

International Search Report and Written Opinion of PCT Application No. PCT/US06/32663, Jul. 31, 2007, 5 pages.

International Search Report and Written Opinion of PCT Application No. PCT/US2005/036690, mailed Jul. 9, 2007, 6 pages.

International Search Report and Written Opinion of PCT Application No. PCT/US09/51288, mailed Sep. 15, 2009, 9 pages.

International Search Report and Written Opinion of PCT Application No. PCT/US08/64255, mailed Sep. 29, 2008, 17 pages.

International Search Report and Written Opinion of PCT Application No. PCT/US06/22594, mailed Oct. 1, 2008, 9 pages.

International Search Report and Written Opinion of PCT/US2012/058106, mailed Nov. 26, 2012, 14 pages.

International Search Report and Written Opinion of PCT Application No. PCT/US08/78810, mailed Feb. 12, 2009, 11 pages.

International Search Report and Written Opinion of PCT/US2012/58176, mailed Jan. 8, 2013, 19 pages.

International Search Report and Written Opinion of PCT Application No. PCT/US12/58074, mailed Mar. 13, 2013, 18 pages.

(56) References Cited

OTHER PUBLICATIONS

Extended European Examination Report of EP Patent Application 06802038.7 dated Nov. 12, 2013, 13 pages.
International Search Report and Written Opinion of PCT/US2012/058182, mailed Mar. 1, 2013, 19 pages.
International Report on Patentability of PCT/US2012/058074 dated Apr. 10, 2014, 8 pages.
International Report on Patentability of PCT/US2012/058176 dated Apr. 10, 2014, 11 pages.
Supplementary European Search Report completed Oct. 29, 2015 for EPO Patent Application No. 12835954 filed Sep. 28, 2012.
International Search Report and Written Opinion mailed Jun. 9, 2014 for International Patent Application No. PCT/US2013/068814 filed Nov. 6, 2013, 18 pages.

* cited by examiner

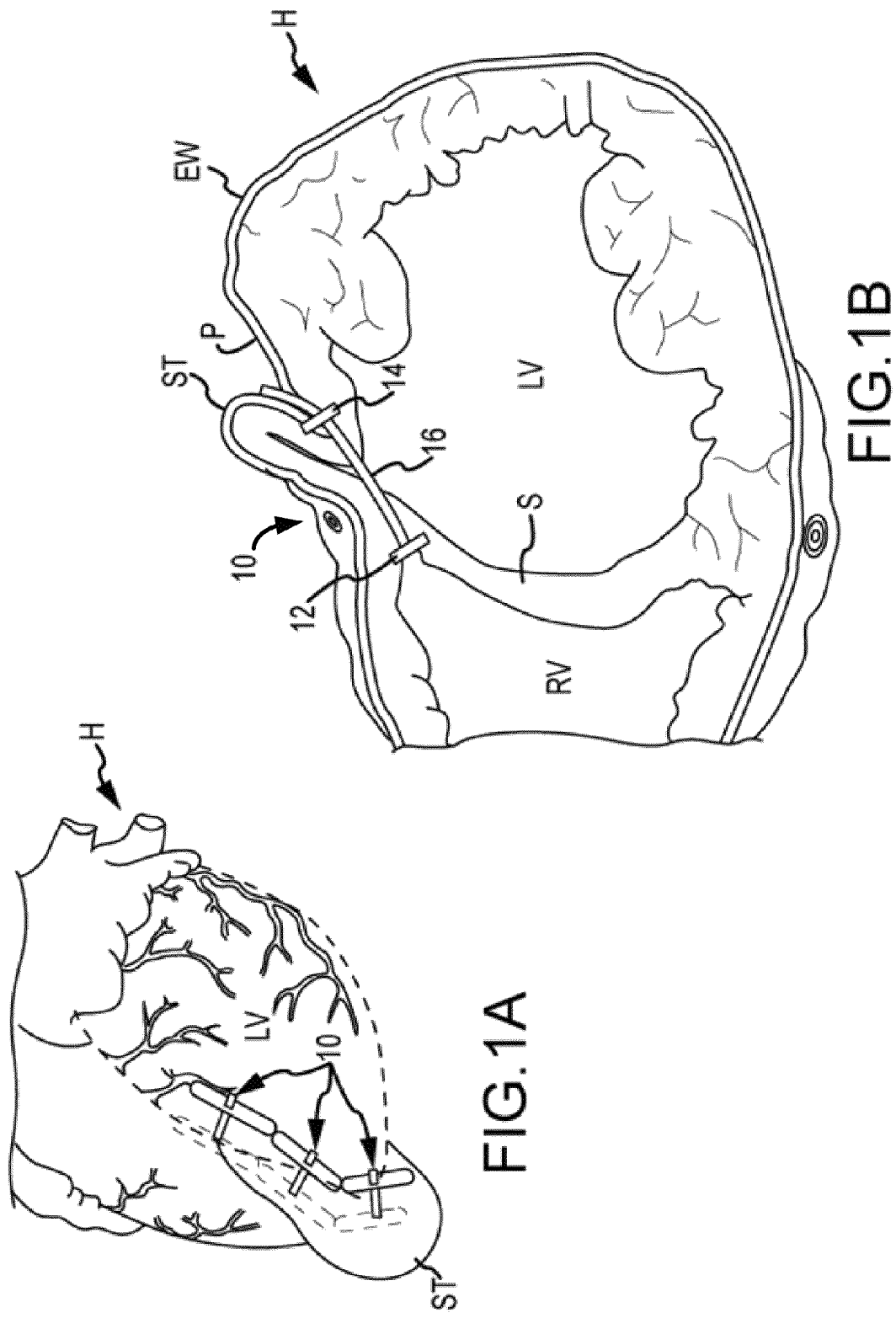

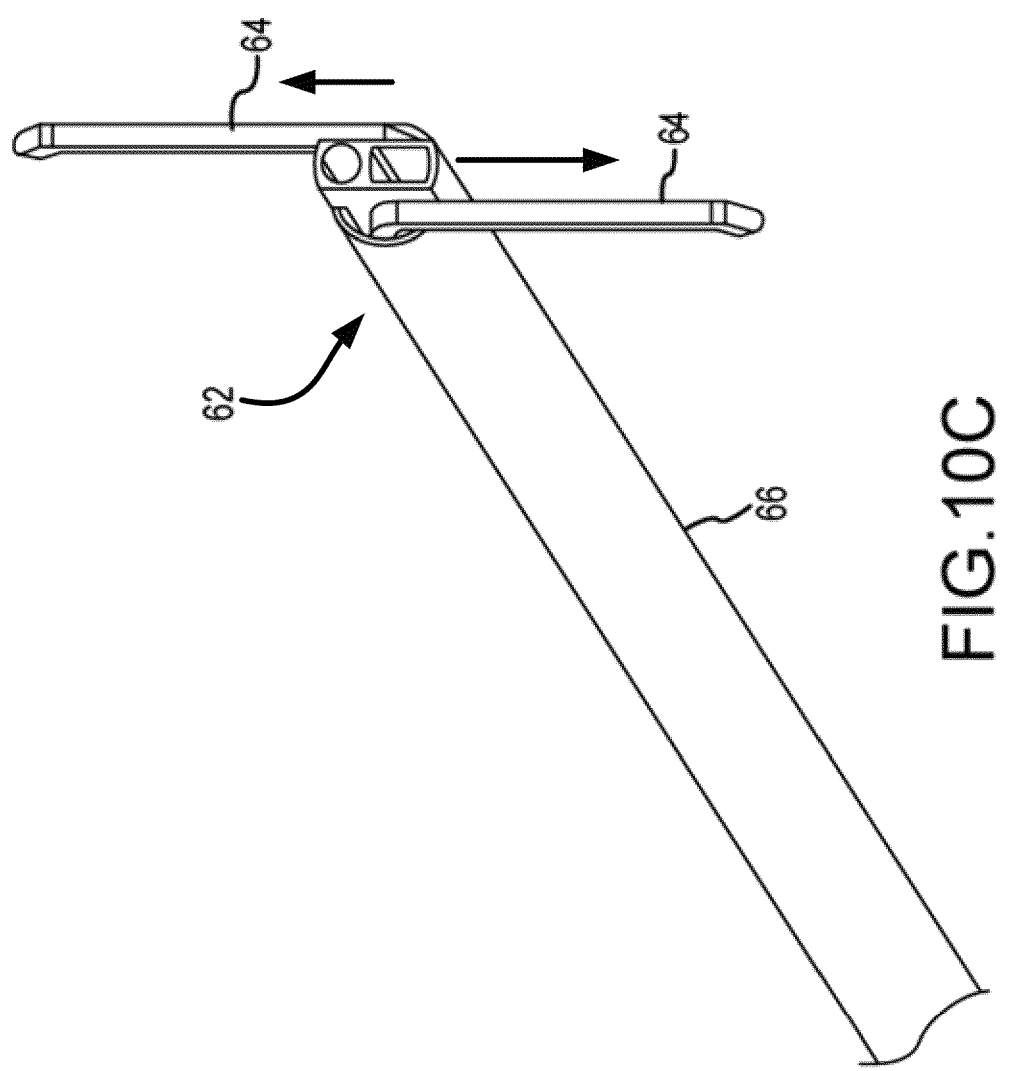

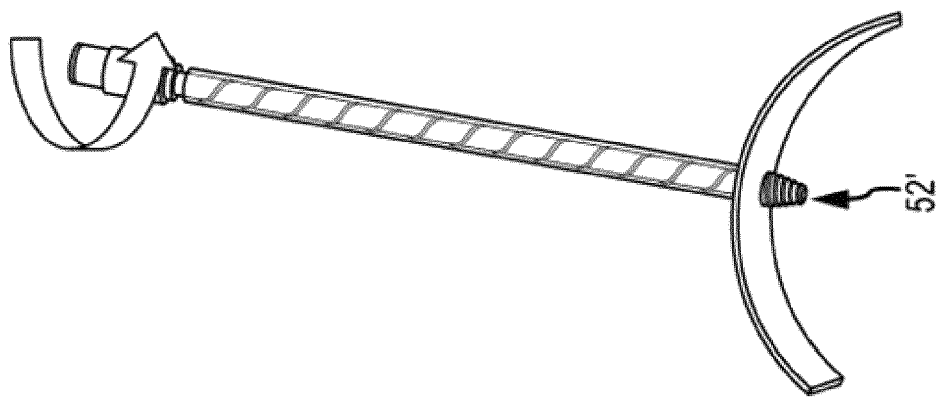
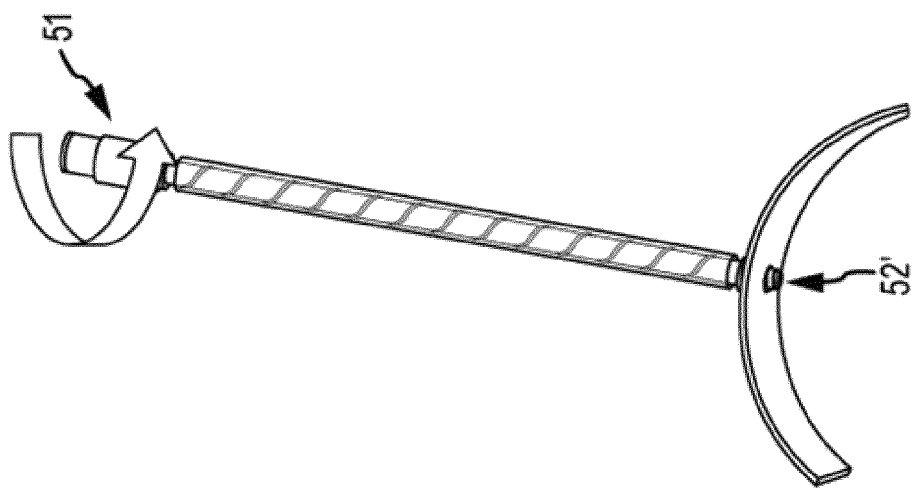
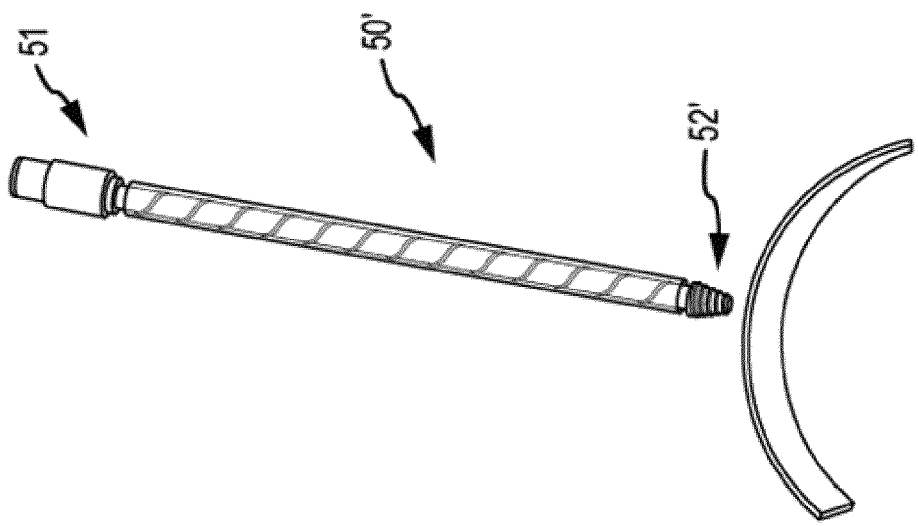

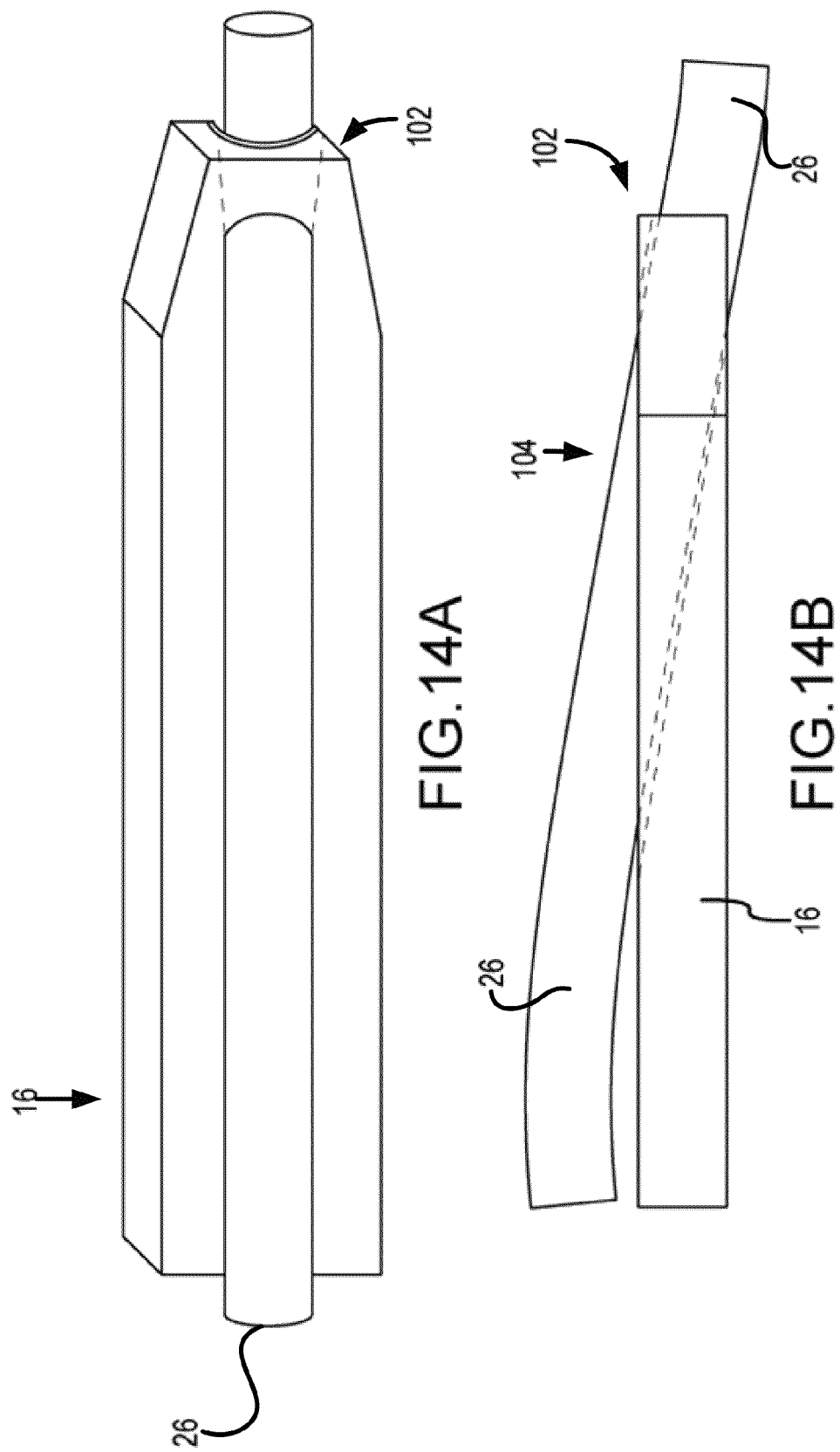

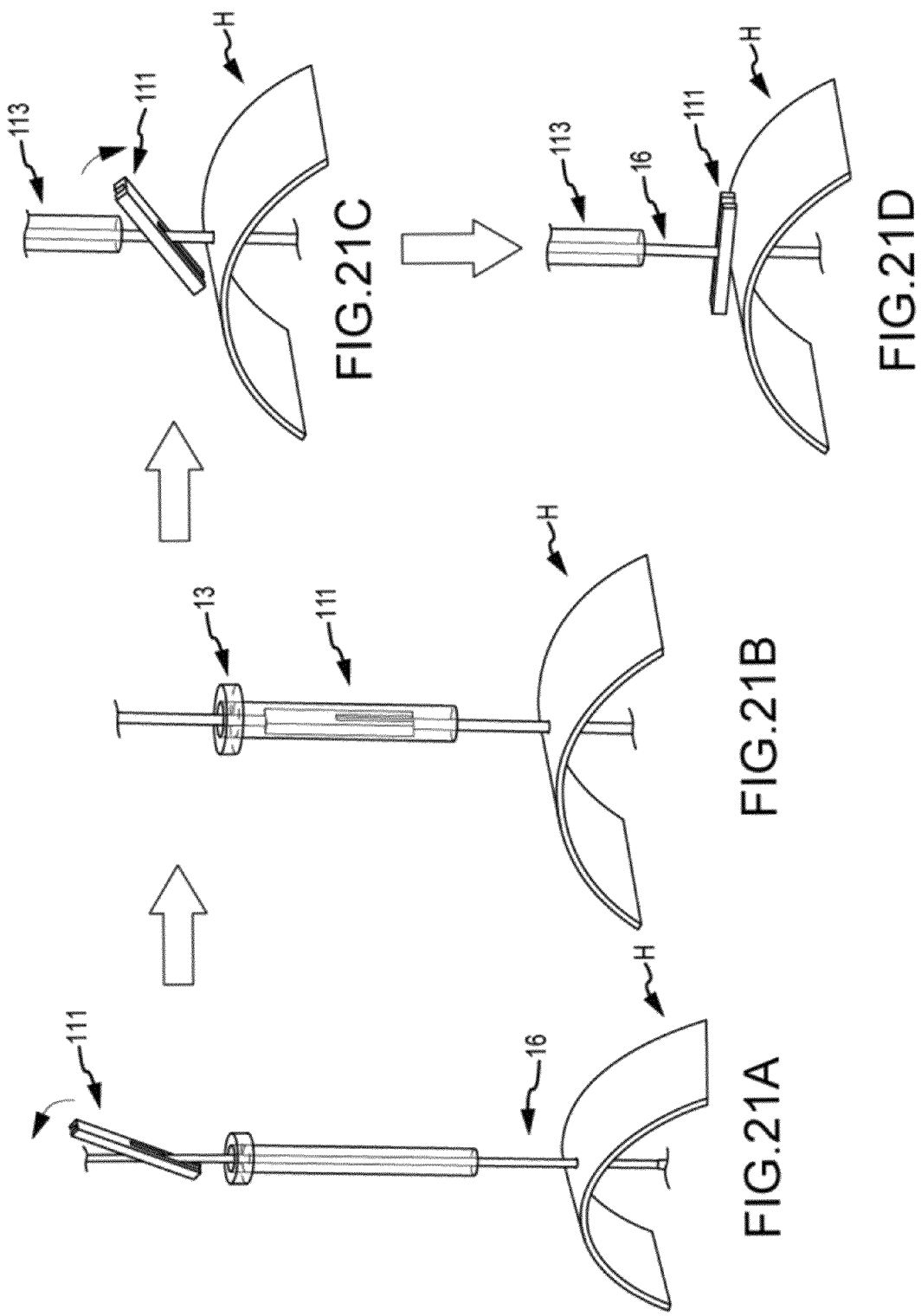

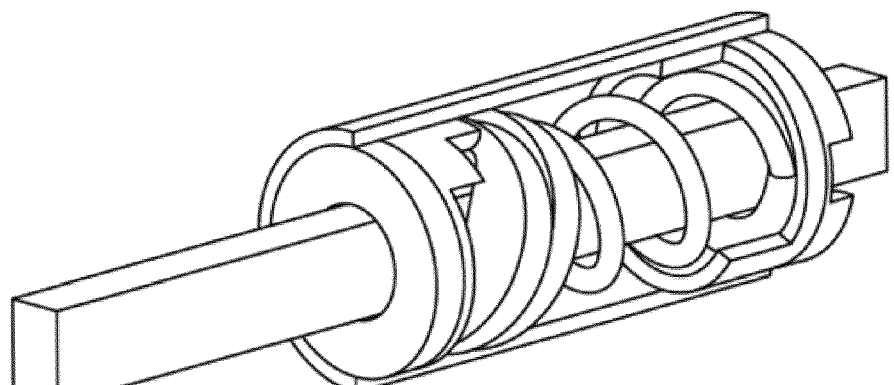
FIG.23
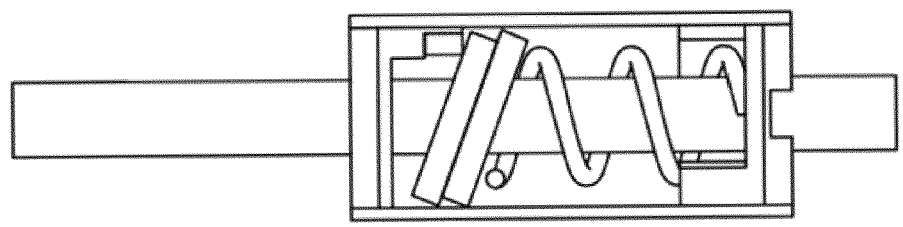
FIG.23A
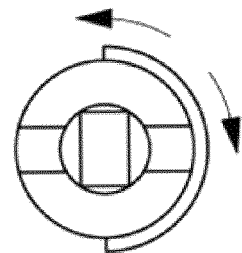 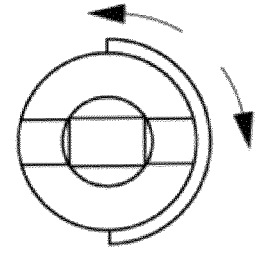
FIG.23B  FIG.23C

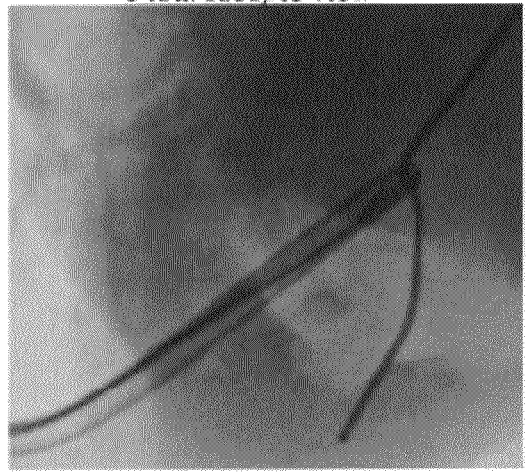
*Flouroscopic view*
FIG. 28f
*External view*
FIG. 28g
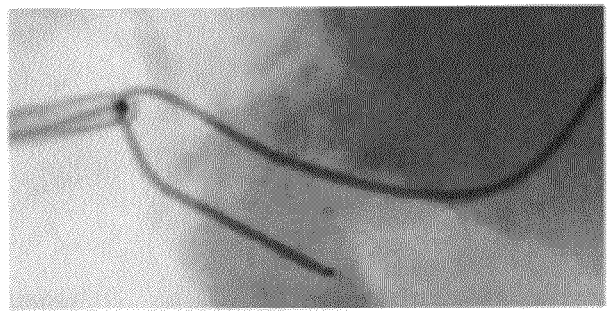
FIG. 28h
FIG. 28i
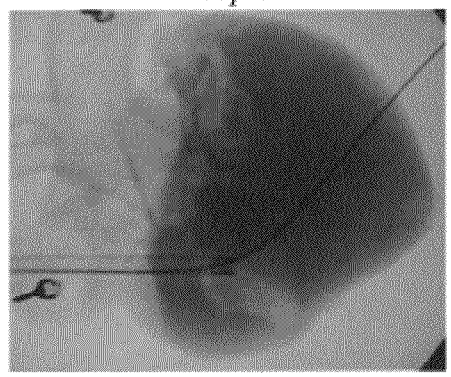
*Flouroscopic view*
FIG. 28j
*External view*
FIG. 28k

*Flouroscopic view*        *External views*
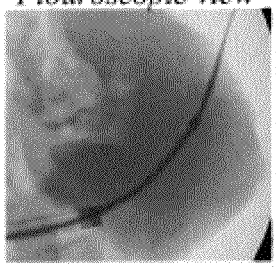
FIG. 28l
FIG. 28m
FIG. 28n
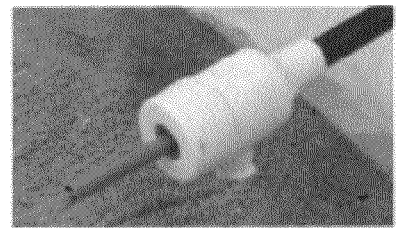
FIG. 28o
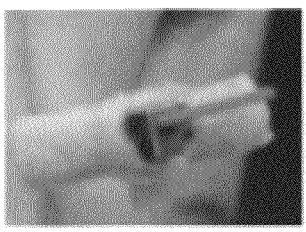
FIG. 28p
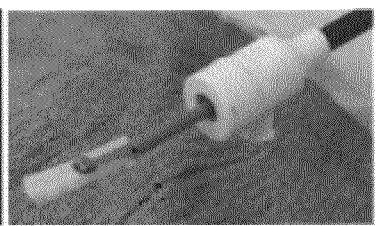
FIG. 28q
FIG. 28r
Anchor placed within hypotube
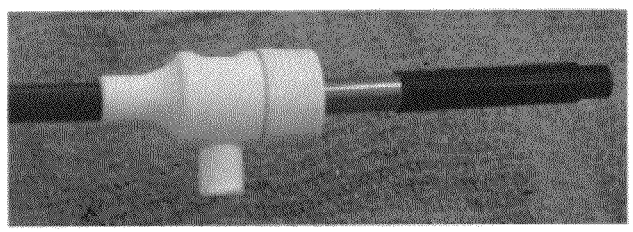
Hypotube placed within sheath
FIG. 28s

*Flouroscopic view*

*External view*

*Anchor has been released from the sheath, aligned and positioned along the RV septum*

FIG. 28x
*Flouroscopic view*
FIG. 28y
*External view*
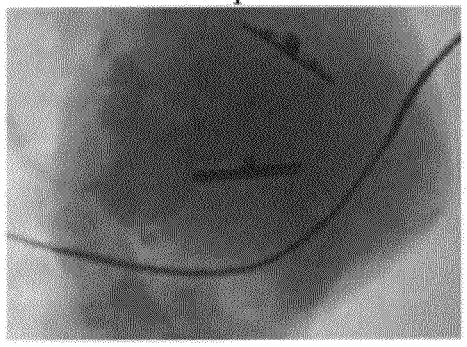
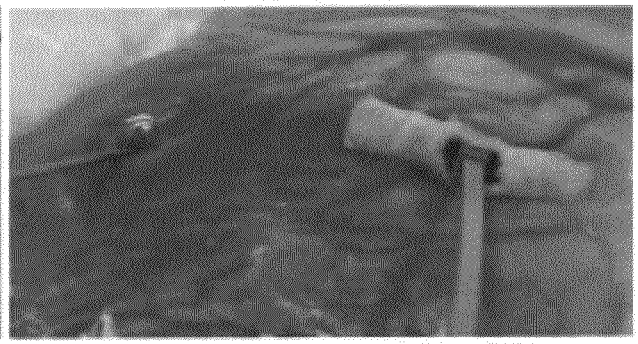
After sheath and dilator placements the anchor is placed in the RV septum and an external anchor secures the anchor pair in place. The final result is shown below:
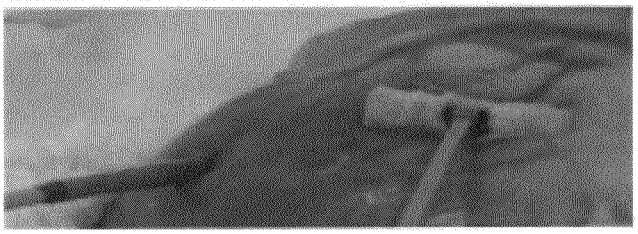
FIG. 28z
*Flouroscopic view*
*External view*
First Anchor Set
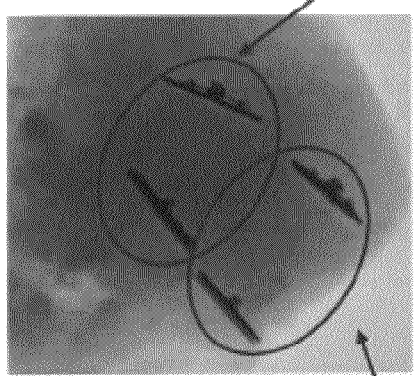
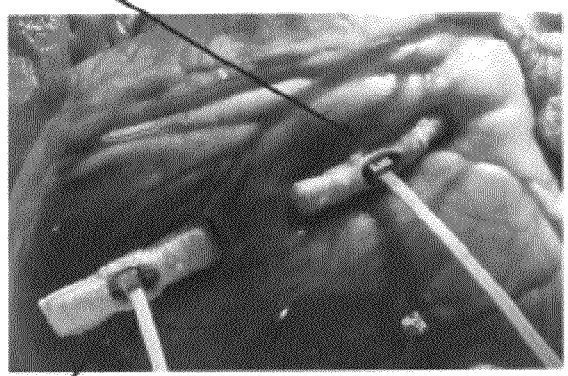
FIG. 28z1
Second Anchor Set
FIG. 28z2

*Internal view of the opened right ventricle*
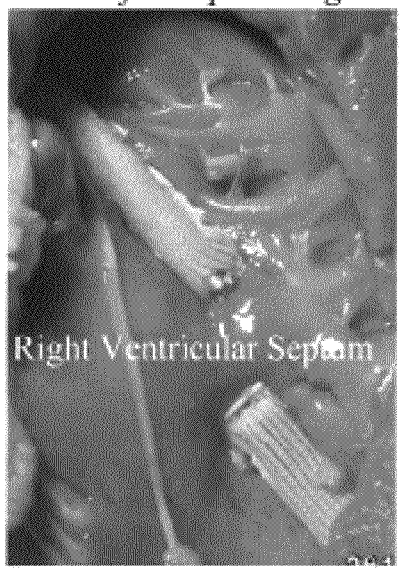
FIG. 28z3
First Anchor Set
Second Anchor Set
FIG. 33a
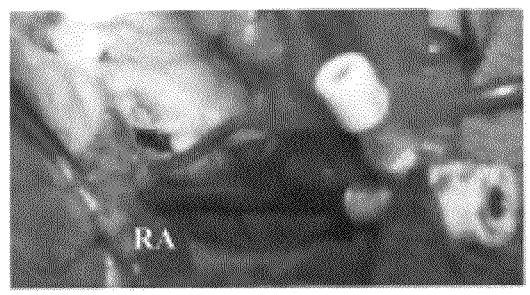
FIG. 33b
FIG. 33c

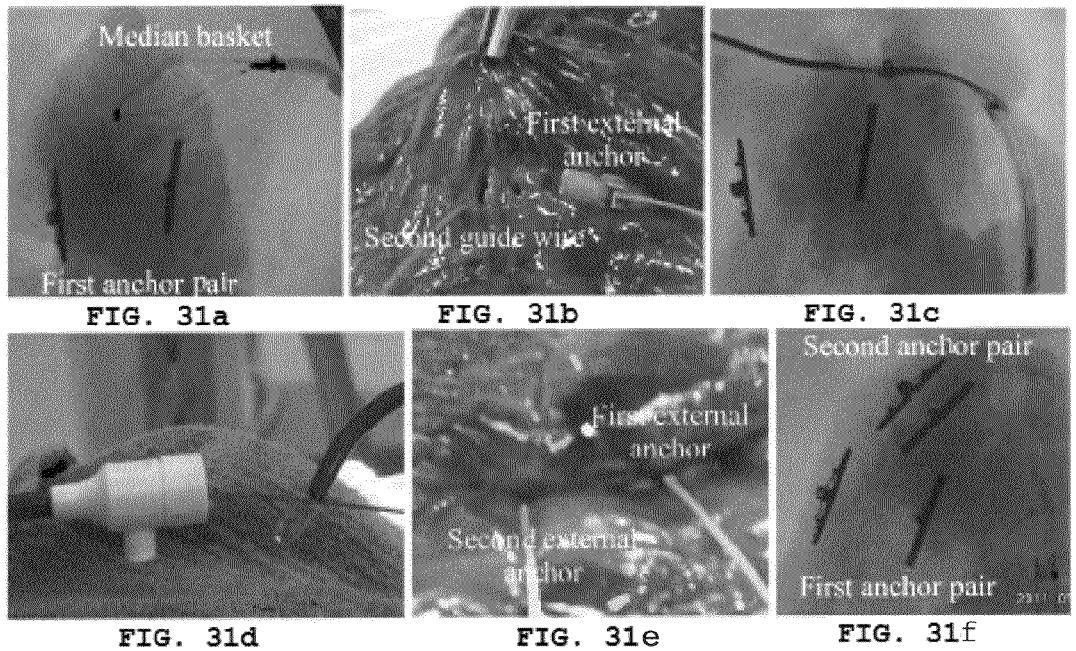
FIG. 31a  FIG. 31b  FIG. 31c
FIG. 31d  FIG. 31e  FIG. 31f
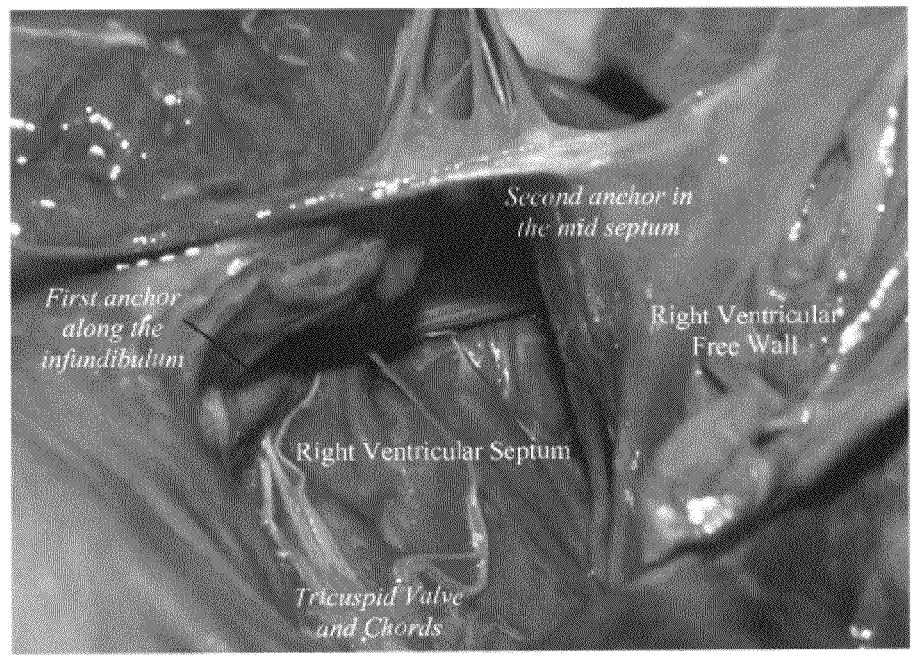
FIG. 32a

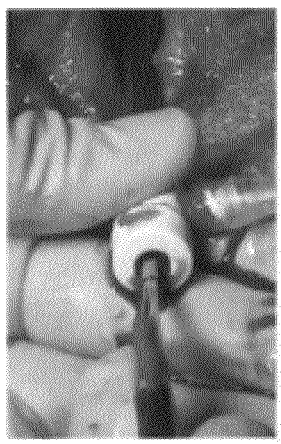 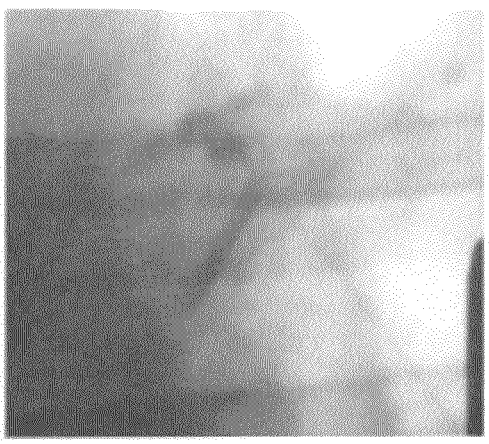 
FIG. 36a　　　　　　FIG. 36b　　　　　　FIG. 36c
  
FIG. 37a　　　　　　FIG. 37b　　　　　　FIG. 37c
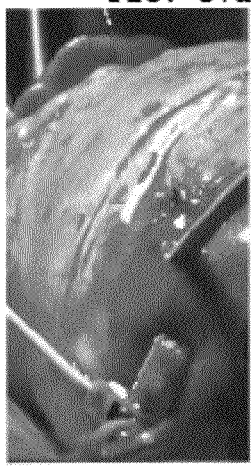  
FIG. 37d　　　　　　FIG. 37e　　　　　　FIG. 37f

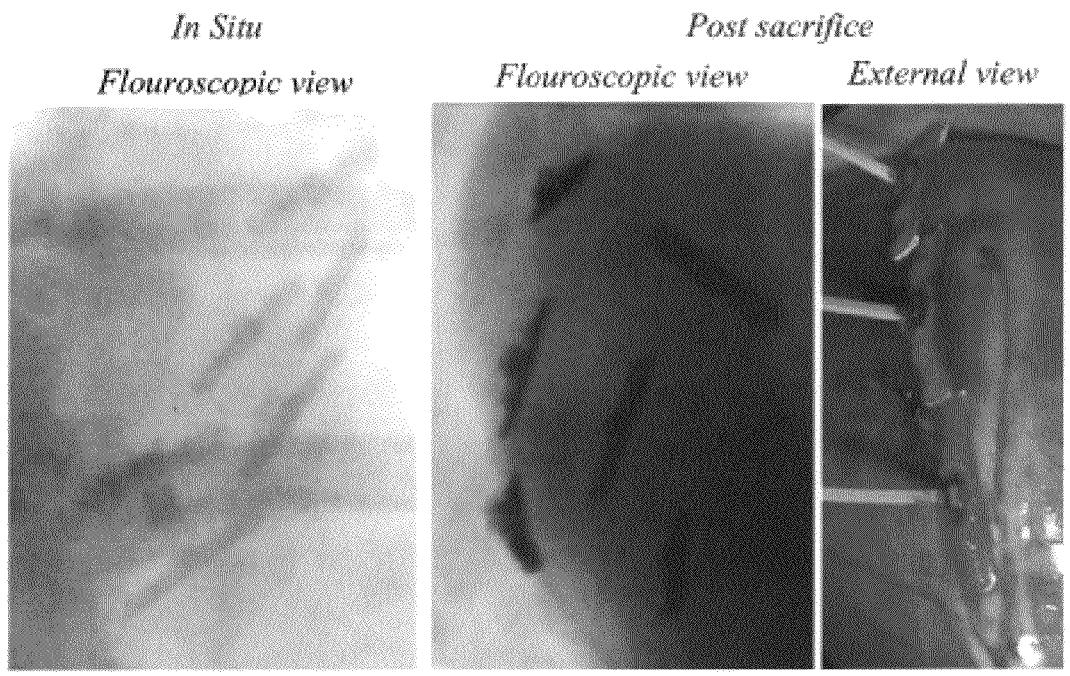
| *In Situ* | *Post sacrifice* | |
|---|---|---|
| *Flouroscopic view* | *Flouroscopic view* | *External view* |
| FIG. 38a | FIG. 38b | FIG. 38c |
*External view*
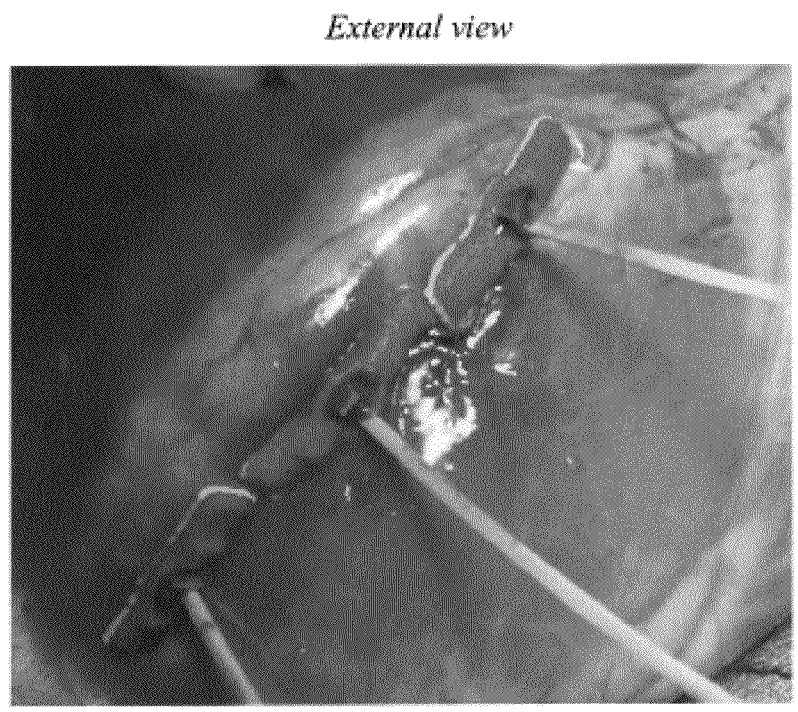
FIG. 38d

*Internal view of the opened right ventricle*

*Internal view of the opened left ventricle*

TRANS-CATHETER VENTRICULAR RECONSTRUCTION STRUCTURES, METHODS, AND SYSTEMS FOR TREATMENT OF CONGESTIVE HEART FAILURE AND OTHER CONDITIONS

CROSS-REFERENCES TO RELATED APPLICATIONS

This application is a division of U.S. Pat. No. 8,979,750 entitled "Trans-Catheter Ventricular Reconstruction Structures, Methods, and Systems for Treatment of Congestive Heart Failure and Other Conditions," filed Sep. 30, 2012, which is related to and claims the benefit of the following U.S. Provisional Patent Applications: Application No. 61/541,624 entitled "Trans-Catheter Ventricular Reconstruction Structures, Methods, and Systems for Treatment of Congestive Heart Failure and Other Conditions," filed Sep. 30, 2011, Application No. 61/541,975 entitled "Remote Pericardial Hemostasis for Ventricular Access and Reconstruction or Other Organ Therapies," filed Sep. 30, 2011; Application No. 61/541,980 entitled "Over-The-Wire Cardiac Implant Delivery System for Treatment of CHF and Other Conditions," filed Sep. 30, 2011; and U.S. Provisional Patent Application No. 61/541,978 entitled "Cardiac Implant Migration Inhibiting Systems," filed Sep. 30, 2011; the full disclosures of which are incorporated herein by reference in their entirety.

The subject matter of this application is related to that of US Patent Publication No. US2009/0093670, as published on Apr. 9, 2009 and entitled "Treating Dysfunctional Cardiac Tissue;" and to that of US Patent Publication No. US2010/0016655, as published on Jan. 21, 2010 and entitled "Cardiac Anchor Structures, Methods, and Systems for treatment of Congestive Heart Failure and Other Conditions;" the full disclosures of which are incorporated herein by reference in their entirety.

BACKGROUND OF THE INVENTION

The present invention is related to improved medical devices, systems, and methods, with many embodiments being particularly useful for reducing the distance between two points in tissue in a minimally or less invasive manner. Specific reference is made to the treatment of a failing heart, particularly the alleviation of congestive heart failure and other progressive heart diseases. The provided devices, systems, and methods will often be used so as to resize or alter the geometry of a ventricle in a failing heart, such as by reducing its radius of curvature through the process of excluding a portion of the circumference from contact with blood, and thereby reduce wall stress on the heart and improve the heart's pumping performance. Although specific reference is made to the treatment of congestive heart failure, embodiments of the present invention can also be used in other applications in which tissue geometry is altered.

Exemplary embodiments described herein provide implants and methods for alleviating congestive heart failure and other progressive diseases of the heart. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited. Implant locations and overall chamber remodeling achieved by placement of a series of implants may be determined so as to provide a beneficial volumetric decrease and chamber shape.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

An exemplary method and implant for closing off a lower portion of a heart ventricle is described in U.S. Pat. No. 6,776,754, the full disclosure of which is incorporated herein by reference. A variety of alternative implant structures and methods have also been proposed for treatment of the heart. U.S. Pat. No. 6,059,715 is directed to a heart wall tension reduction apparatus. U.S. Pat. No. 6,162,168 also describes a heart wall tension reduction apparatus, while U.S. Pat. No. 6,125,852 describes minimally-invasive devices and methods for treatment of congestive heart failure, at least some of which involve reshaping an outer wall of the patient's heart so as to reduce the transverse dimension of the left ventricle. U.S. Pat. No. 6,616,684 describes endovascular splinting devices and methods, while U.S. Pat. No. 6,808,488 describes external stress reduction devices and methods that may create a heart wall shape change. US Patent Publication No. US2009/0093670 describes structures and methods for treating dysfunctional cardiac tissue, while US Patent Publication No. US2010/0016655 describes cardiac anchor structures, methods, and systems for treatment of congestive heart failure and Other Conditions. The full disclosures of all of these references are incorporated herein by reference in their entirety.

While the proposed implants, systems, and methods may help surgically remedy the size of the ventricle as a treatment of congestive heart failure and appear to offer benefits for many patients, still further advances would be desirable. In general, it would be desirable to provide improved devices, systems, and methods for treatment of congestive heart failure. It would be particularly desirable if such devices and techniques could decrease the trauma imposed on collateral tissues when gaining access to the target tissues for treatment, when positioning implants and other therapeutic devices for use, and when treating the target tissue. It would be also be beneficial to enhance the accuracy of ventricular reconstruction while simplifying the overall procedure, ideally while decreasing the sensitivity of the therapy on unusual surgical skills. It would be advantageous if these improvements could be provided without overly complicating the structures of implants or implant deployment systems, and while significantly enhancing the benefits provided by the implanted devices.

BRIEF SUMMARY OF THE INVENTION

Embodiments of the present invention provide improved medical devices, systems, and methods, in many cases for reducing the distance between two locations in tissue, optionally in a less or minimally invasive manner. The present invention may find specific use in the treatment of a failing heart, particularly for the alleviation of congestive heart failure and other progressive heart diseases by reconfiguring abnormal heart geometry that may be contributing to heart dysfunction. In many embodiments, implant components will be positioned at least partially within a chamber of the heart. For example, an anchor of an implant system may, when the system is fully deployed, reside within the right ventricle in engagement with the ventricular septum. A tension member may extend from that anchor through the septum and an exterior wall of the left ventricle to a second anchor along an epicardial surface of the heart. Perforating both the exterior wall and the septum from an epicardial approach can provide beneficial control over the effective reshaping of the ventricular chamber. Despite this largely epicardial approach, there are surprising benefits to guiding deployment of the implant from along both the epicardial access path and another access path into and through the right ventricle. For example, controlling the movement of the anchor within the right ventricle from a joined epicardial pathway and right atrial access pathway can help avoid entangling the anchor with chordea supporting the tricuspid valve and the like. In fact, despite the epicardial formation of perforations through both the left ventricular exterior wall and the septum, by advancing the anchor into the heart via the right atrium (optionally via a femoral or jugular access) behind and axially affixed to the tension member, the tension member can then be pulled from the epicardial access site. Application of controlled pressure against an epicardial anchor and locking of the implant (ideally both through a working lumen of a minimally invasive epicardial access tool) allows the implant system to be safely, quickly, and accurately deployed without having to rely on complex catheter steering systems within a beating heart or the like.

In a first aspect, the invention provides a method for treating a heart within a patient. The heart has first and second chambers with a septum therebetween, the second chamber having an exterior wall. The method comprises advancing a first elongate shaft from outside the patient into the heart along a first path so that a distal end of the first shaft is disposed in the first chamber. A second elongate shaft is advanced along a second path from outside the heart, through the exterior wall and through the septum so that a distal end of the second shaft is disposed in the first chamber. The first path is joined to the second path by coupling the distal end of the first shaft with the distal end of the second shaft within the first chamber of the heart. A first anchor and an elongate tension member are advanced into the heart along the joined paths, with the tension member being advanced into the first chamber and the tension member being advanced so as to extend from the first anchor in the first chamber, through the septum, through the second chamber, and through the exterior, and so that an end portion of the tension member is disposed outside the heart. A second anchor of the implant is coupled to the tension member end portion outside the heart. Tension is applied between the anchors with the tension member so that the anchors urge the septum and the external wall to engage.

In another aspect, the invention provides a method for treating a heart within a patient having congestive heart failure. The heart has first and second chambers with a septum therebetween, and the second chamber has an exterior wall. The method comprises advancing a first elongate shaft from outside the patient into the heart along a first path so that a distal end of the first shaft is disposed in the first chamber. A second path is formed by advancing a second elongate shaft from outside the heart, through the exterior wall and through the septum so that a distal end of the second shaft is disposed in the first chamber. The distal end of the first elongate shaft is coupled with the distal end of the second elongate shaft within the first chamber of the heart so as to join the first path to the second path. A tension member and a first anchor of an implant are advanced distally into the first chamber of the heart along the first path. The tension member is advanced distally from the chamber by pulling a distal end of the tension member along the second path so that the tension member extends from the first anchor in the first chamber, through the septum, through the second chamber, and through the exterior wall to the distal end of the tension member outside the heart. A second anchor of the implant is coupled to the tension member outside the heart, and tension is applied between the anchors with the tension member so that the septum engages the wall such that the congestive heart failure is mitigated.

In another aspect, the invention provides a method for treating a heart within a patient having congestive heart failure. The heart has first and second chambers with a septum therebetween, the second chamber having an exterior wall. The method comprises advancing a first elongate shaft from outside the patient into the heart along a first path so that a distal end of the first shaft is disposed in the first chamber. A second path is formed by advancing a second elongate shaft from outside the heart, through the exterior wall and through the septum so that a distal end of the second shaft is disposed in the first chamber. The distal end of the first elongate shaft is coupled with the distal end of the second elongate shaft within the second chamber of the heart so as to join the first path to the second path. A first anchor is advanced distally into the first chamber of the heart along the second path and within the first chamber along the first path, wherein the tension member trails proximally from the anchor as the anchor is advanced distally so as to extend from the first anchor in the first chamber, through the septum, through the second chamber, and through the exterior wall to a proximal end of the tension member disposed outside the heart. A second anchor of the implant is coupled to the tension member outside the heart, and tension is applied between the anchors with the tension member so that the septum engages the wall.

In a device aspect, the invention provides a system for treating a heart within a patient. The heart has first and second chambers with a septum therebetween, the second chamber having an exterior wall. The system comprises a first elongate shaft having a proximal end and a distal end, the distal end of the first shaft being configured to be advanced from outside the patient into the heart along a first path so that the distal end of the first shaft is disposed in the first chamber. A second elongate shaft has a proximal end and a distal end, the distal end of the second shaft being configured to be advanced along a second path from outside the heart, through the exterior wall and through the septum so that the distal end of the second shaft is disposed in the first chamber. A first elongate flexible body is slidably coupled to one of the shafts. The first flexible body has a distal end portion configured for in situ coupling, within the first chamber of the heart, with a corresponding distal end portion extending from the other of the shafts so as to join the first path with the second path. An implant is configured to be advanced along the joined paths. The implant includes a first anchor having a low profile configuration for advancement of the first anchor along the joined paths. A second anchor is also included in the implant, along with an elongate tension member having a first end coupleable with the first anchor and a second end coupleable with the second anchor. The first anchor is configured to deploy laterally from the low-profile configuration within the first chamber. The tension member is configured to extend from the first anchor in the first chamber, through the septum, through the second chamber, and through the exterior wall such that applying tension between the anchors with the tension member urges the septum and the external wall to engage.

In many embodiments, the first anchor and the tension member are advanced into the heart while the heart is beating and with the first anchor axially affixed to the tension member. The first anchor may be deployed laterally relative to the tension member within the right ventricle, typically from a low profile configuration to a deployed configuration which inhibits axial movement of the anchor and tension member through the septum. The tension member and the first anchor may be advanced into the right ventricle of the heart along the first path, and the tension member will then preferably be advanced from the right ventricle along the second path by pulling an end of the tension member along the second path through the left ventricle so that the end of the tension member extends outside the heart. Alternatively, the tension member and the first anchor may be advanced into the heart along the second path, with the tension member trailing from the advancing first anchor so as to extend through the left ventricle when the first anchor is advanced into the right ventricle. Optionally, a distal portion of the tension member and the first anchor may be advanced along the second path within a dilating catheter having a dilating distal tip. The anchor can be laterally released from the dilating catheter by retracting a sheath of the dilating catheter proximally from the dilating tip. In exemplary embodiments the anchor comprises an elongate structure pivotably coupled to the tension member, and the anchor has a guidewire lumen. This allows the anchor to be advanced over a guidewire extending along one or both of the paths, thereby providing control over both the orientation and position of the anchor within the chambers of the heart. The guidewire can be withdrawn and the anchor repositioned by pulling a tether or the like so that the anchor extends laterally from the tension member.

The first path will typically comprise a right atrial path traversing the right atrium of the heart, with the right atrial path optionally being formed using a flexible vascular access device such as by advancing a catheter or the like through a femoral approach, a jugular approach, or the like. In some embodiments, an at least semi-rigid shaft may be used to form the right atrial path, such as by advancing a tissue penetrating trocar through an external wall of the right atrium into the right atrial appendage. The second path will typically be formed by an at least semi-rigid shaft such as a curved needle, though steerable tissue penetrating catheters such as transceptal access catheters or the like may alternatively be used. The curved needle may have a sharp tissue penetrating tip at the distal end of the second shaft and a lumen extending axially toward the tip.

A first flexible body (such as a guidewire or snare) may optionally be advanced through or over the first elongate shaft so that an end portion of the first flexible body is disposed in the first chamber. A second flexible body (such as a guidewire or snare) may also be advanced through or over the second elongate shaft so that an end portion of the second flexible body is disposed in the first chamber. The coupling of the distal end of the first elongate shaft with the distal end of the second elongate shaft may be performed by axially coupling the flexible bodies together within the first chamber of the heart. For example, the axial coupling of the flexible bodies may be effected by capturing one of the end portions of one of the flexible bodies within an opening in the end portion of the other flexible body. The end portion of the other flexible body may comprise a snare, so that advancing the end portion beyond a restraining lumen of the associated shaft expands the snare in the first chamber of the heart so as to expand the opening. An exemplary snare comprises a basket snare, which is configured to expand by releasing the basket snare from a lumen of the first elongate shaft so that the basket snare expands from a low profile insertion configuration to an expanded configuration encompassing a volume of the first chamber. The axial coupling of the flexible bodies may be performed by shrinking the opening, typically by withdrawing the opening into the first or second shaft. The end portion of the second flexible body can be pulled from the first chamber through the first elongate shaft and out of the patient, with the second flexible body comprising a guidewire having an opposed end. This can leave the guidewire extending from the end portion, into the right ventricle, through the septum, through the left ventricle, through the external wall, and out of the patient to the opposed end. In other embodiments, the other end portion comprises an end portion of the tension member.

When the first anchor is advanced, the first anchor may include an elongate shaft or arm having an axial lumen that is pivotably coupled to the tension member. The guidewire can help maintain an axial orientation of the anchor, preferably with the arm extending along the tension member while the anchor is advanced axially into and within the right ventricle of the heart. The anchor may optionally be advanced into and/or within the heart using a flexible compressive shaft, sometimes referred to as a pusher catheter or pushtube. The pusher catheter may have separate lumens configured for receiving the guidewire and tension member, with both lumens extending between a distal anchor-pushing end and a proximal end. The separate lumens enhance rotational control of the anchor about the axis of the tension member, and facilitates orienting the arms of the anchor by rotating of the pushtube from outside the patient. In some embodiments, the tether may have an elongate cross-section and the lumen of the pusher catheter which receives the tether may have a corresponding elongate cross-section so as to inhibit rotation of the tether within the lumen and enhance rotational control over the advanced anchor after the guidewire is pulled free of the anchor. In some embodiments a working lumen of an epicardial hemostasis tool may be used to help gain access to an epicardial surface region of the heart. The epicardial region may encompass the second path through the exterior wall, and the hemostasis tool may compress the exterior wall of the heart inwardly around the second path so as to inhibit bloodflow from the left ventricle along the second path. The second anchor may be advanced toward the epicardial region through the working lumen.

In many embodiments, post-deployment migration of the anchors may be inhibited by applying a desired anchor force between the tension member and the second anchor while the second anchor is in a variable force mode. The second anchor in the variable force mode can slide axially proximally and distally along the tension member, and is configured to be reconfigured from the variable force mode to a set force mode while the desired anchor force is applied. The second anchor in the set force mode inhibits movement of the second anchor along the tension member away from the first anchor. The desired anchor force may be applied to the second anchor by engaging the second anchor through a working lumen of a minimally invasive access tool with a compression shaft, and may be reconfigured from outside the patient body through the working lumen.

BRIEF DESCRIPTION OF THE DRAWINGS

FIG. 1A shows a reconstructed left ventricle using a series of implanted anchors so as to mitigate the deleterious effects of congestive heart failure, according to an embodiment of the invention;

FIG. 1B is a cross-sectional view of the heart of FIG. 1A, showing a reduction in the size of the left ventricle effected by one of the implants;

FIGS. 14A-14C schematically illustrate coupling of a tension member to a guidewire so as to facilitate guiding the tension member into and through the heart;

FIGS. 21A-D illustrate insertion of an epicardial-engagement portion of an anchor over a tension member and through a working lumen of a minimally-invasive access device so as to distribute an anchoring load of an anchor lock along a desired contour;

FIGS. 23-24B illustrate alternative epicardial anchors which are adapted to be advanced along and reconfigured between a variable-force mode and a set force mode via a working lumen of a minimally invasive epicardial access device;

FIGS. 25a-28z3 illustrate deployment of an embodiment of a remote ventricular reconstruction implant in a pig cadaver heart, as described in the Experimental section;

FIGS. 29a-32c illustrate deployment of an embodiment of a remote ventricular reconstruction implant in a human cadaver heart, as described in the Experimental section;

FIGS. 33a-39b illustrate deployment of an embodiment of a remote ventricular reconstruction implant in a live sheep heart, as described in the Experimental section;

DETAILED DESCRIPTION OF THE INVENTION

Figure 2A:
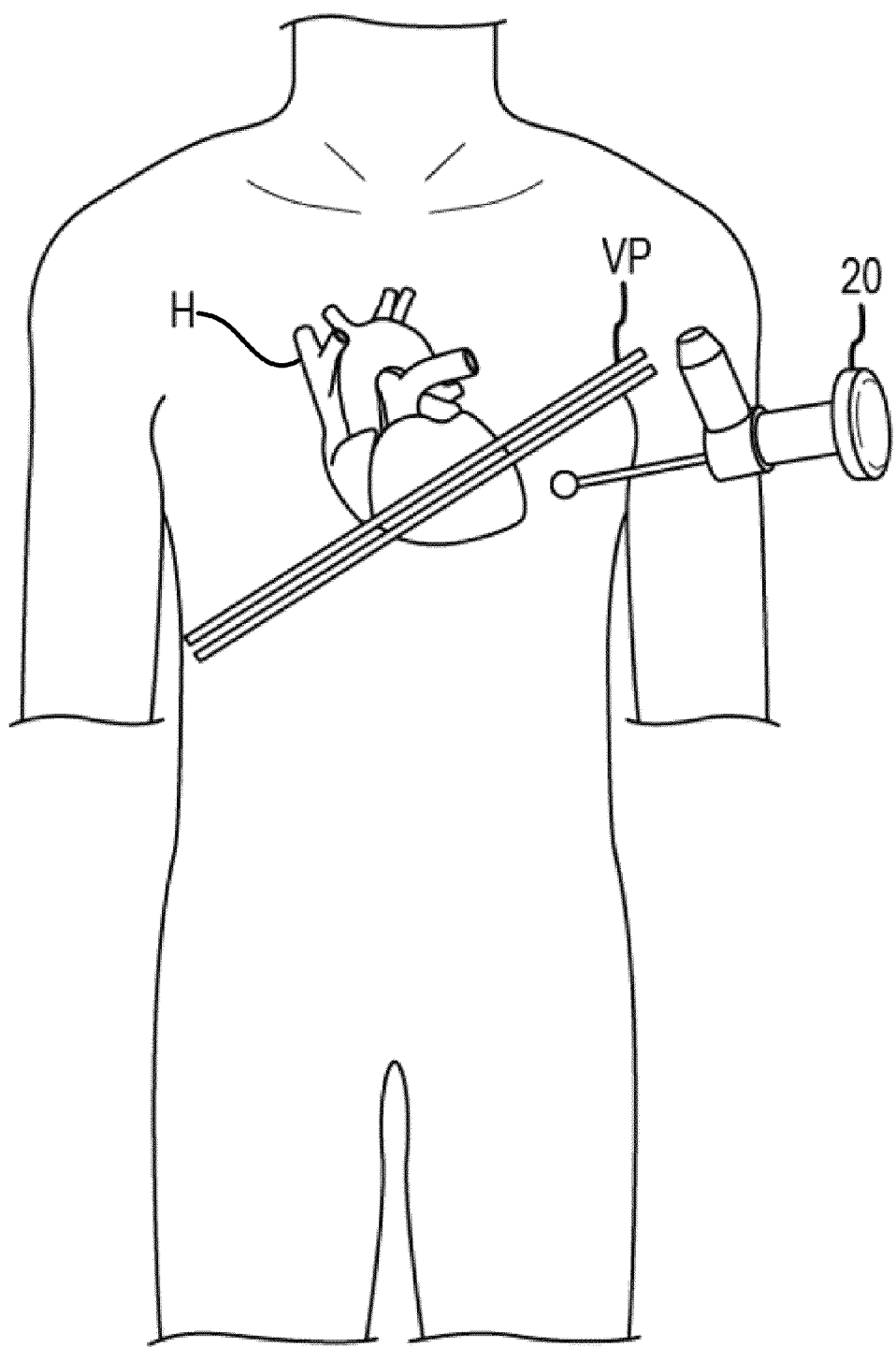
FIGS. 2A and 2B schematically illustrate minimally invasive access to and endoscopic imaging of a pericardium of the heart.

The present invention generally provides improved medical devices, systems, and methods. Exemplary embodiments of the devices are described for use in reducing the distance between a region along the septum and a region of an external wall of the left ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction. For congestive heart failure therapies, perforating both the exterior wall and the septum from an epicardial approach can provide significant benefits in control over the locations of implant deployments, thereby effectively enhancing the resulting reshaping of the ventricular chamber. Despite this largely epicardial approach, there are surprising benefits to guiding deployment of the implant from along both the epicardial access path and another access path into and via an access path through the right ventricle. This additional right atrial access path into the heart may be via the superior vena cava, the inferior vena cava, the right atrial appendage, or the like, and the pathways may be joined together by coupling of a snare to a guidewire or the like within the right ventricle, the right atrium, the right pulmonary artery, or the like. While a variety of tools will be described herein for providing access pathways, for joining pathways together within the heart, for deploying implants, for maintaining hemostasis, and the like, it should be recognized that alternative embodiments may employ additional or alternative structures, some of which may be off-the-shelf, and some of which may be new structures configured particularly for use in the advantageous therapies described herein. For example, embodiments of the systems, implants, and techniques described herein may employ components described in US2009/0093670, as published on Apr. 9, 2009 and entitled "Treating Dysfunctional Cardiac Tissue;" and/or in US Patent Publication No. US2010/0016655, as published on Jan. 21, 2010 and entitled "Cardiac Anchor Structures, Methods, and Systems for treatment of Congestive Heart Failure and Other Conditions;' the full disclosures of which are incorporated herein by reference in their entirety.

Referring now to FIGS. 1A and 1B, a series of implants 10 are shown implanted in a heart H so as to decrease a cross-section of a left ventricle LV. Each implant 10 generally includes a first anchor 12, a second anchor 14, and a tension member 16 coupling the anchors together. Tension in the tension member 16 is transferred from the anchors 12, 14 to the septum S and the external wall EW bordering the left ventricle LV so as to bring these structures into engagement, thereby effectively excluding a region of scar tissue ST from the left ventricle. In many embodiments described herein, implant 10 will be deployed by penetrating the external wall EW and septum S via a pericardium P of the heart H, and also by accessing a right ventricle RV via a right atrium. Anchors deployed within a right ventricle and/or in engagement with the septum S may sometimes be referred to herein as septal anchors, while anchors deployed along the external wall EW of the left ventricle LV may be referred to as epicardial anchors.

Figure 2B:
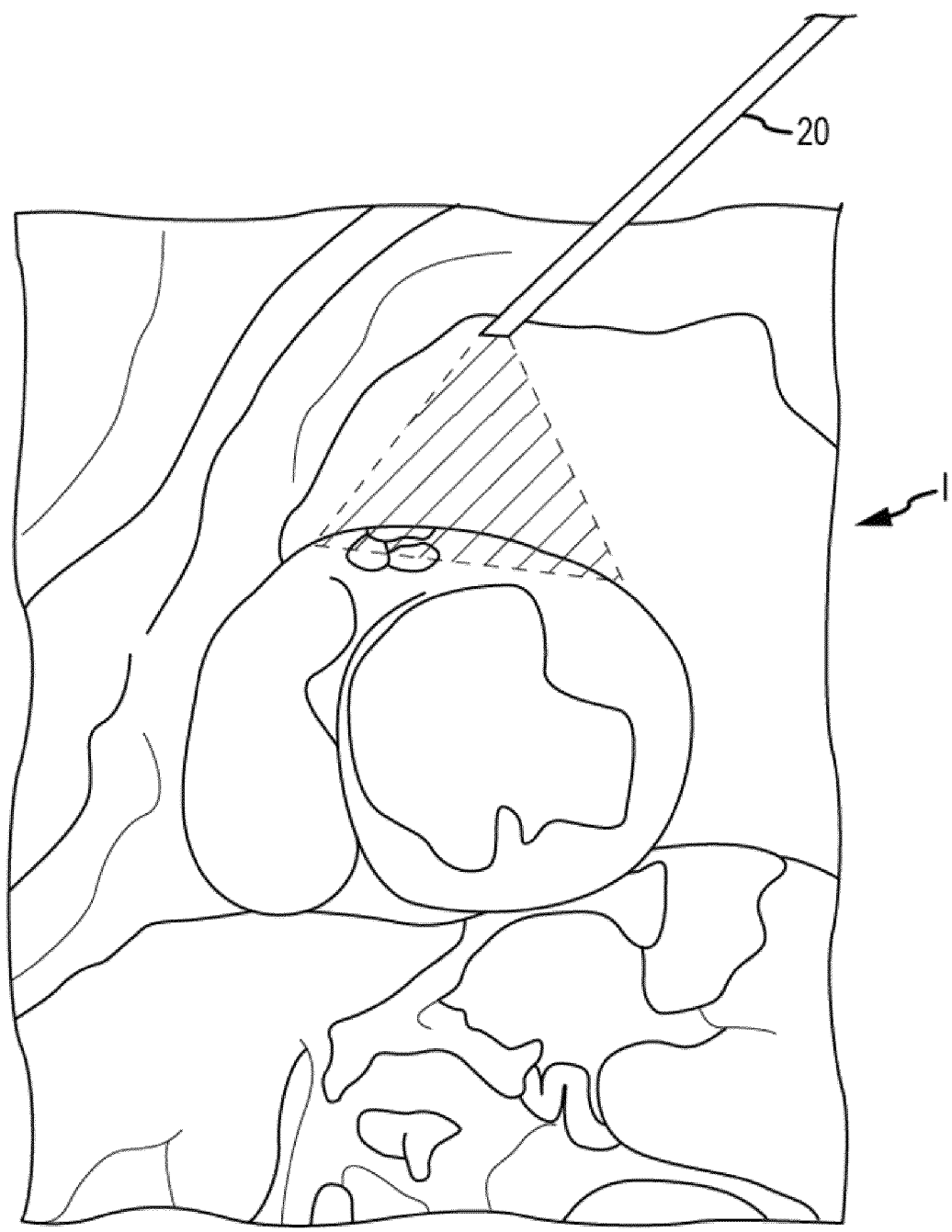

Referring now to FIGS. 2A and 2B an MRI image I taken along viewing plane VP schematically illustrates use of a thoracoscope 20 to provide a field of view encompassing a region of the pericardium of the heart, with the region including a target site for deployment of one or more epicardial anchors of the implant system.

Figure 3:
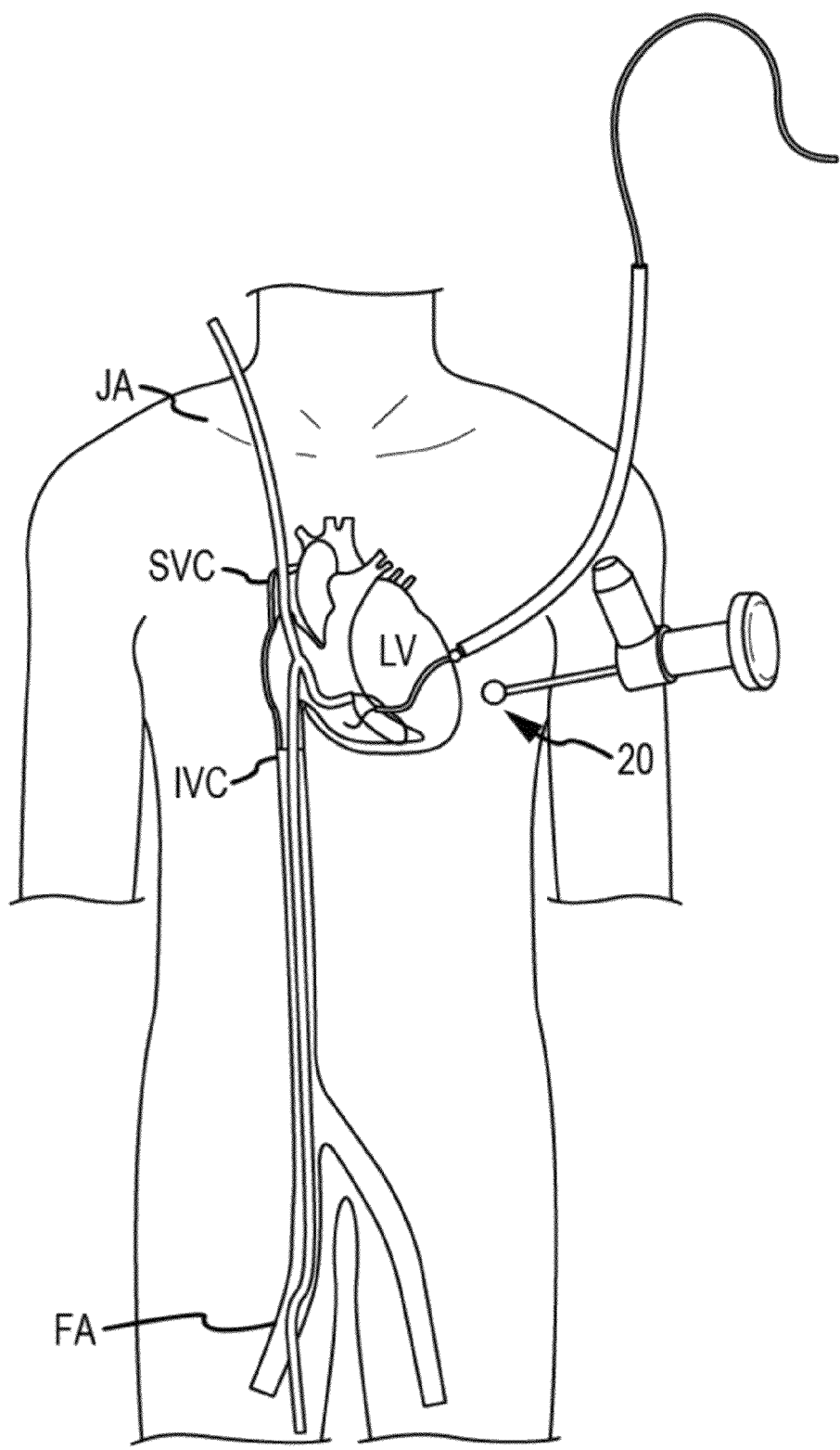
FIG. 3 schematically illustrates joining of a femoral access tool path through the right atrium and an endoscopic trans-epicardial access tool path by snaring a guidewire within the right ventricle of the heart.

Referring now to FIG. 3, joining of an access path through the right atrium to an access path through the pericardium and epicardium by snaring of a guidewire within the right ventricle under thoracoscopic guidance 20 is schematically illustrated. The right atrial access path may extend into the arterial vasculature via the femoral artery FA and inferior vena cava IVC, via the jugular artery JA via the superior vena cava, or the like. As can be understood with reference to FIG. 3A, a selected location for perforation of the external wall EW can be identified using an image from thoracoscope 20, optionally in combination with an image from another imaging modality (such as a prior or contemporaneous image from an ultrasound imaging system, an MRI imaging system, an X-ray or fluoroscopic imaging system, a CT imaging system, or the like. In exemplary embodiments, a rigid or semi-rigid shaft of an access tool 22 having a working lumen therethrough is advanced through the epicardium of the beating heart so that a distal end of the shaft is disposed within the left ventricle LV. Access tool 22 may comprise a relatively simple needle or trocar, an may have a proximal hemostasis valve at its proximal end so as to inhibit bloodflow through the lumen and facilitate insertion and/or removal of a guidewire and the like. In some embodiments, access tool 22 may have a tissue penetrating sharpened distal end to facilitate distal insertion, and/or a stylus may be removably disposed within the lumen. Optional embodiments of access tool 22 may have an energy delivery surface at or near the distal end so as to deliver radiofrequency energy, laser energy, or the like to facilitate penetrating the tissue of the external wall EW. Suitable RF penetrating structures may be commercially available from (or modified from those available from) Baylis Medical of Toronto Canada.

Figure 3A:
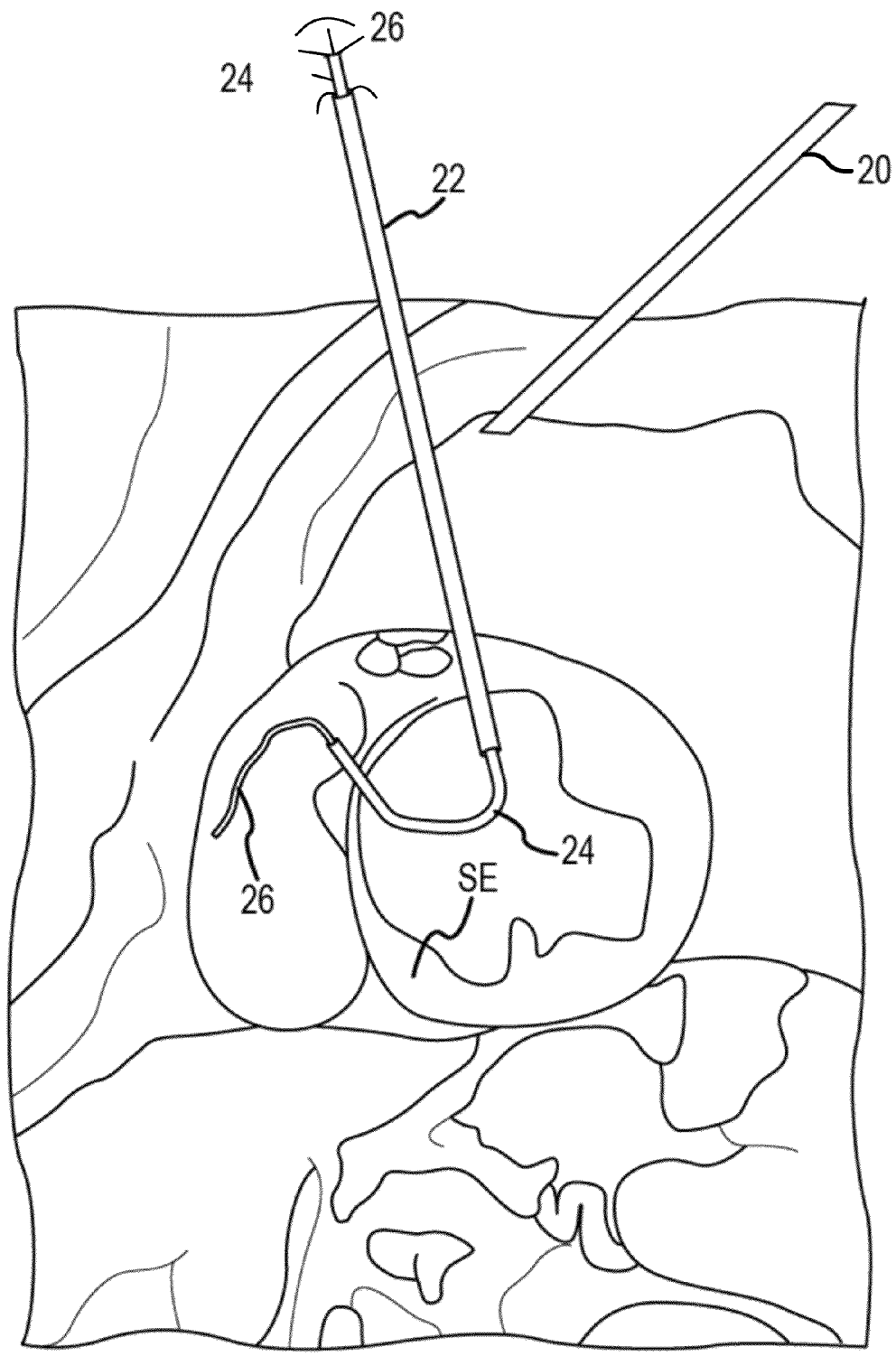
FIG. 3A schematically illustrates introducing a guidewire into a right ventricle of the heart through an external wall of the left ventricle and through the septum so as to form an epicardial access path.
Figure 10:
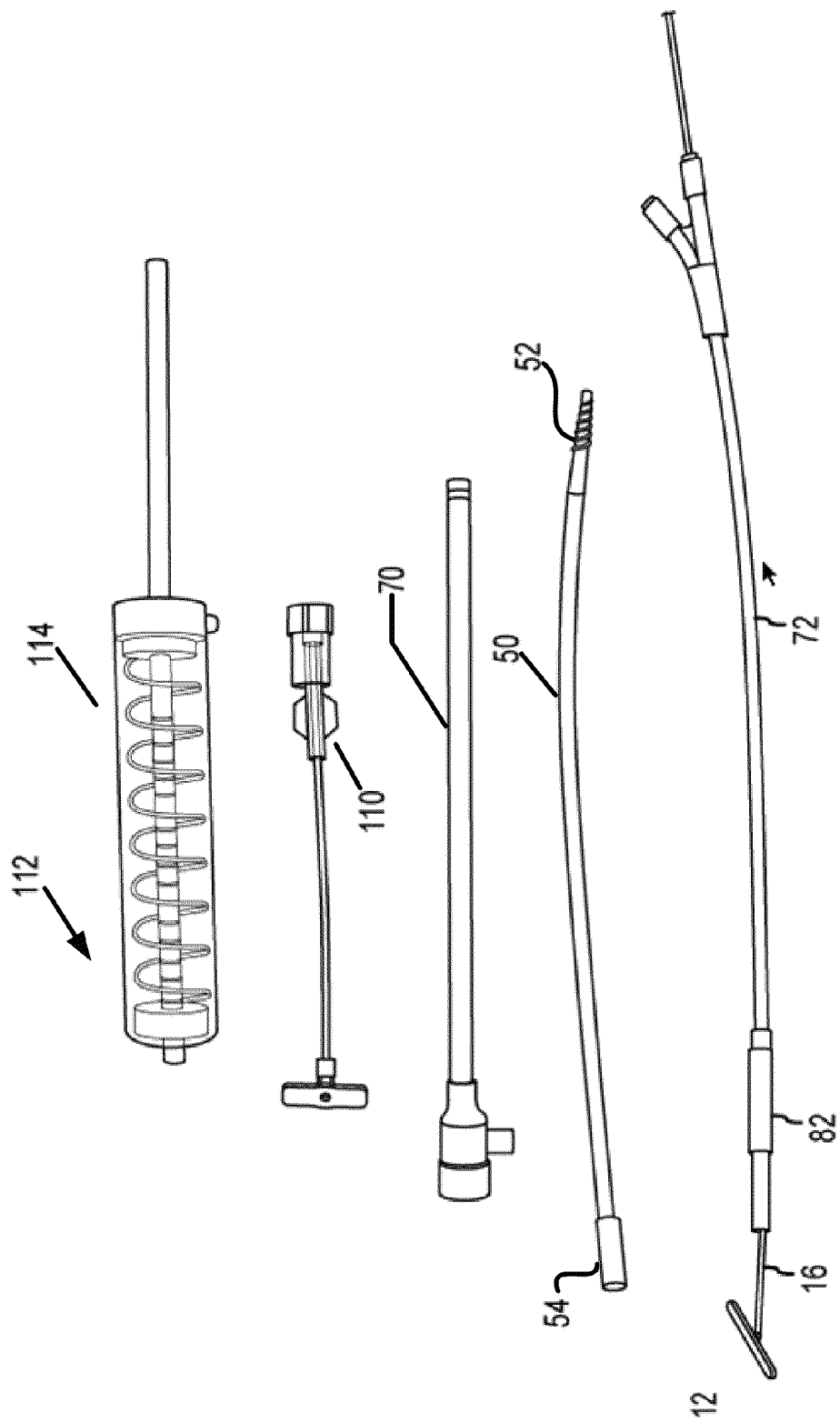
FIGS. 10-10F illustrate components of an over-the-wire implant delivery system and their use.
Figure 10A:
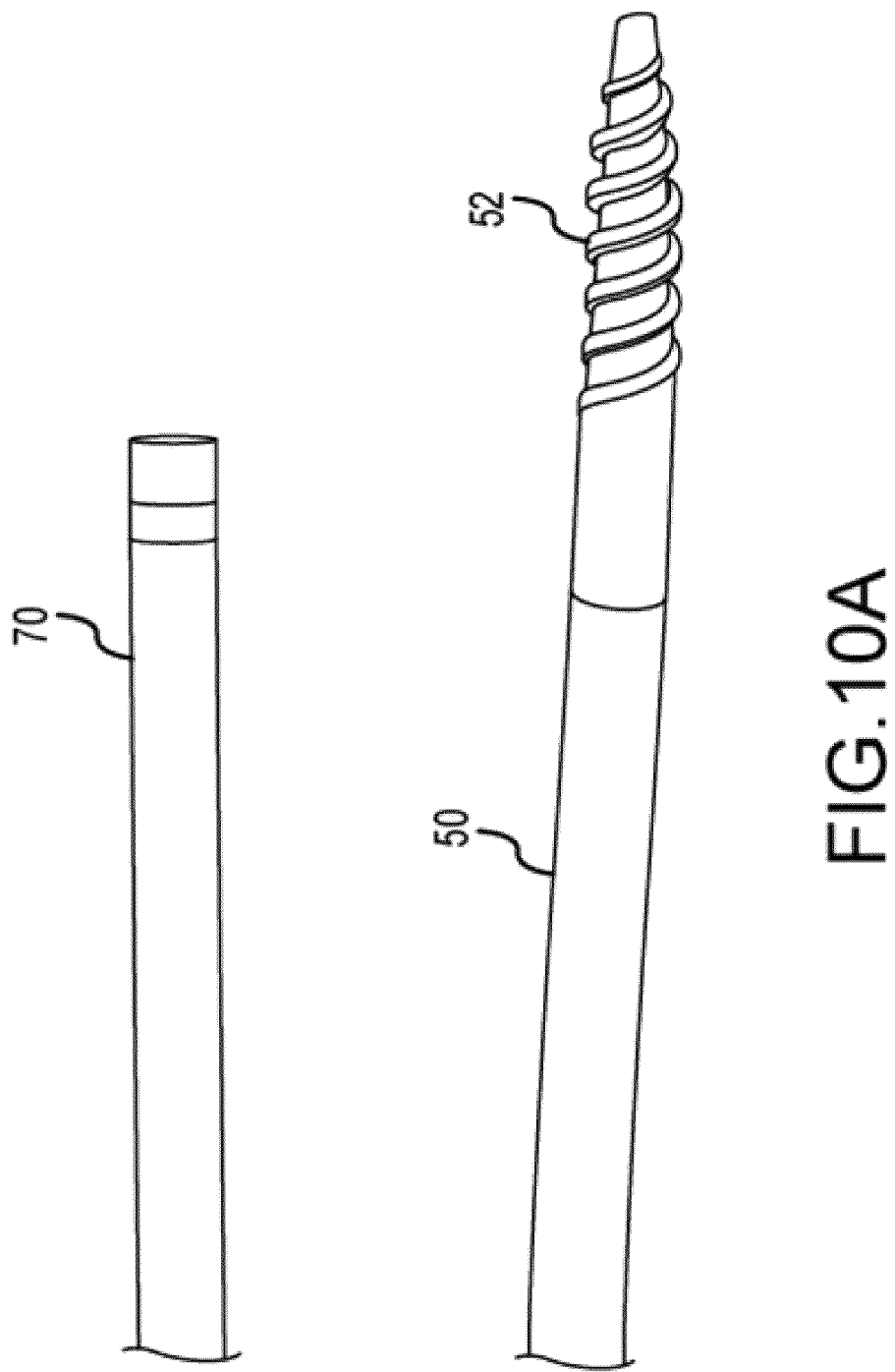
FIGS. 10G-10I illustrate an exemplary an axially flexible helical screw-tip dilator and its use for traversing a wall of the heart.
Figure 10B:
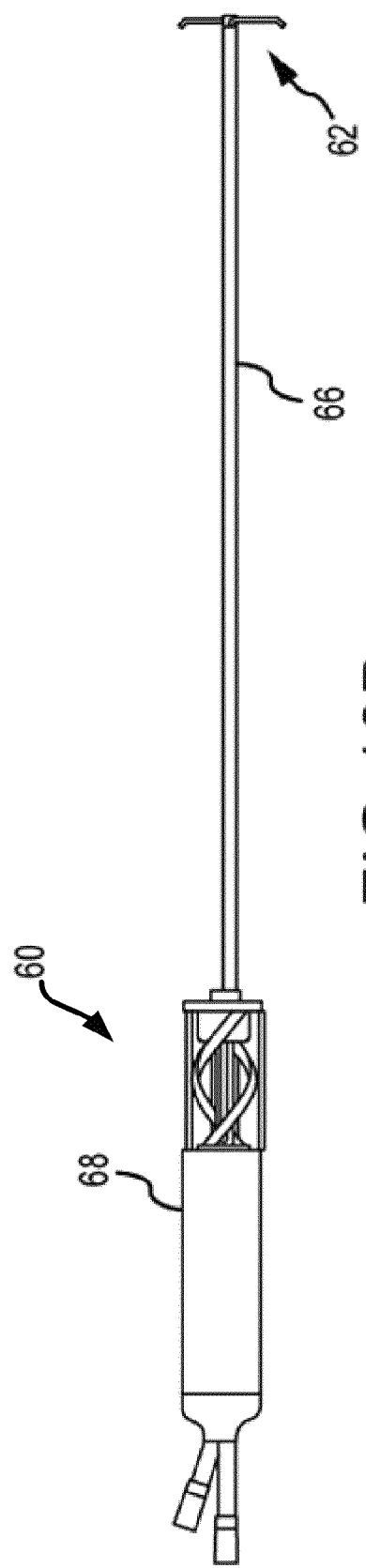
Figure 10D:
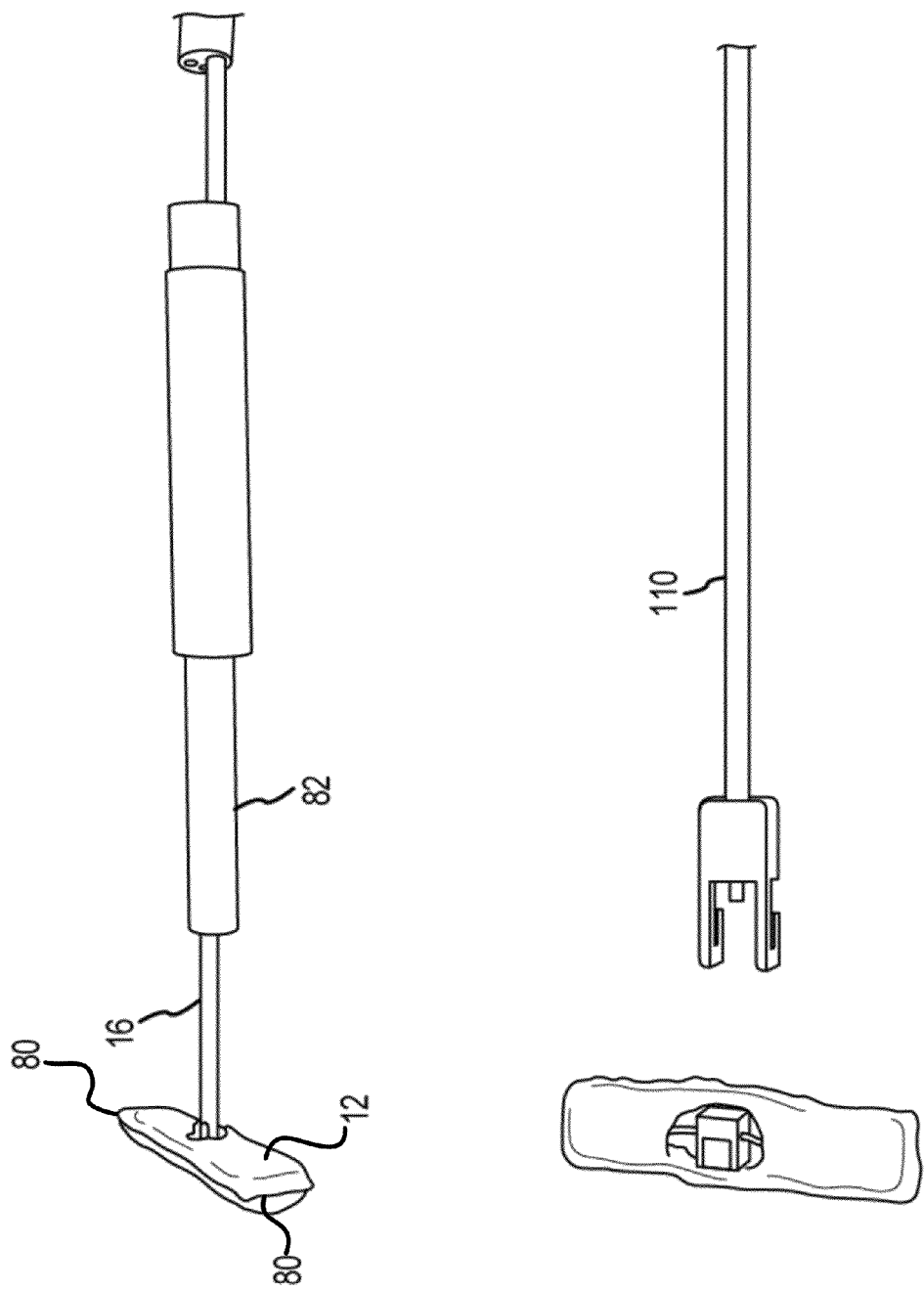
Figure 10E:
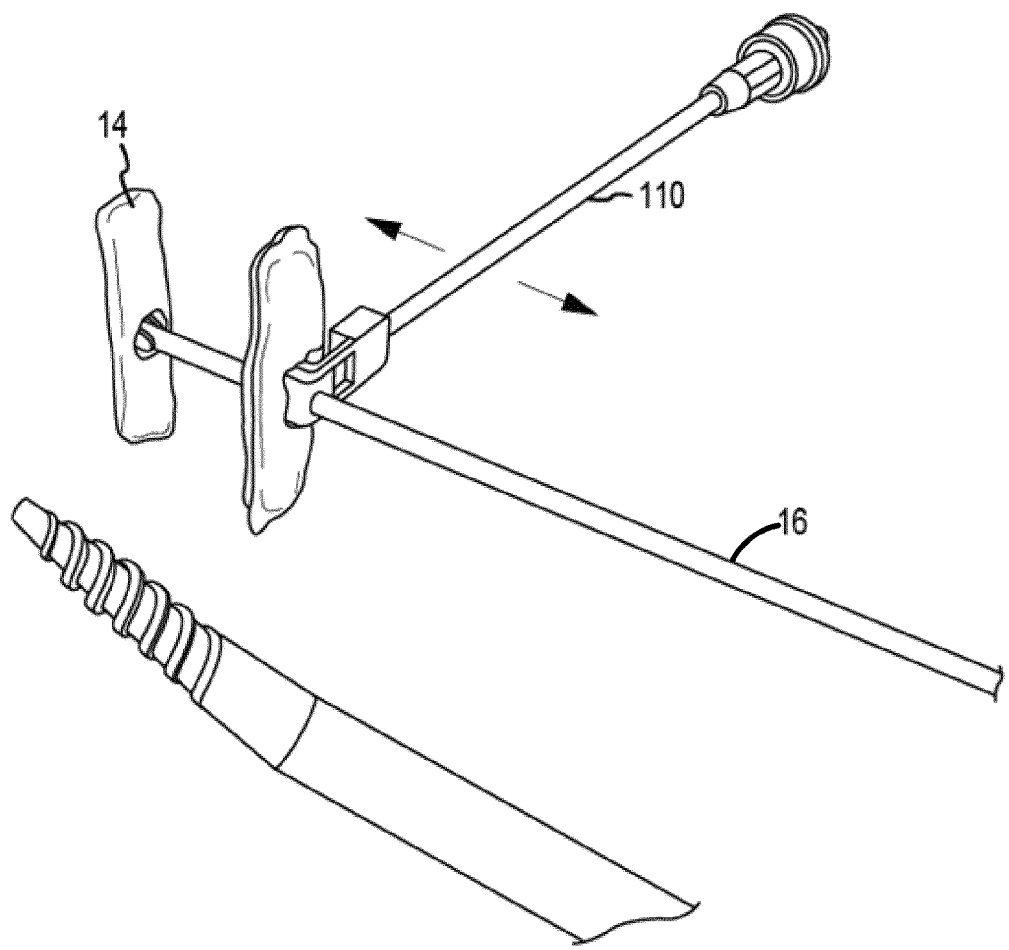
Figure 10F:
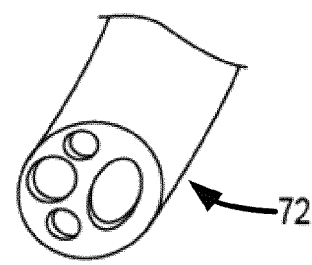

Still referring to FIG. 3A, access tool 22 may optionally include a laterally deployable structure near the distal end so as to stabilize the access tool relative to the beating heart tissue around the left ventricle. Suiitable deployable stabilizing structures may include a malecott, a pair of opposed deployable arms (optionally similar to those described below with reference to FIGS. 10B and 10C), or the like. The laterally deployable distal structure may be configured for engagement against an interior surface of the left ventricle LV or against the epicardial surface of the left ventricle (such as by having the deployable structure spaced proximally of the distal end). Regardless, once access tool 22 is disposed within the left ventricle, a catheter 24 may be advanced through the working lumen of access tool 22, into the left ventricle, and through a target location of the septum S. A guidewire 26 will also be inserted through the left ventricle and septum as shown. A variety of structures and techniques can be used for perforating the septum, with the catheter optionally being used to penetrate the septum in some embodiments, with the catheter optionally having a sharpened end, a removable stylus, an energy delivery surface, or the like. When catheter 24 perforates the septum, the catheter will often have steering capabilities so as to facilitate perforation at a target location, though in some embodiments catheter 24 may be steered using steering capabilities of the guidewire within the working lumen, a steering catheter extending around the catheter and through the working lumen of access tool 22, or the like. In other embodiments, guidewire 26 may be used to perforate through the septum, with the guidewire optionally having an energy delivery tip and/or steering capabilities, with the catheter being advanced through the septum over the guidewire. Exemplary steerable guidewires with RF penetrating tips include those commercially available from (or may be derived from those available from) Baylis Medical of Toronto Canada.

A wide variety of alternative septum perforation approaches might be employed, including using atrial septum perforation structures and techniques (or structures and techniques derived therefrom). For example, mechanical systems may employ a sharpened distal tip and axial penetration (such as using structures commercially available from—or structures derived from—the SafeSept™ transseptal guidewire commercially available from Adaptive Surgical, LLC; the ACross Transseptal Access System commercially available from St Jude, or the like), a rotatable angled blade, the transseptal puncturing structures and methods described by Wittkampf et al. in US2011/0087261, or the like. RF systems may employ a proprietary tissue penetrating structure or may energize an off-the-shelf transseptal needle with RF energy, as was described by Knecht et al. in an article entitled "Radiofrequency Puncture of the Fossa Ovalis for Resistant Transseptal Access," Circ Arrhythm Electrophysiol 1, 169 (2008). Laser-energy transseptal approaches may also be employed, including structures commercially available from (or derived from those commercially available from) Spectranetics and others.

Once catheter 24 is advanced through the septum, the working lumen of the catheter may be used to access the right ventricle from outside the patient, with the guidewire optionally being removed and replaced (particularly when the guidewire has been used to perforate the septum) with another guidewire, or remaining for use in joining the access paths. To facilitate use of catheter 24 as a right ventricle access tool and swapping guidewires or the like, a hemostasis valve may be provided at a proximal end of the catheter.

Figure 3B:
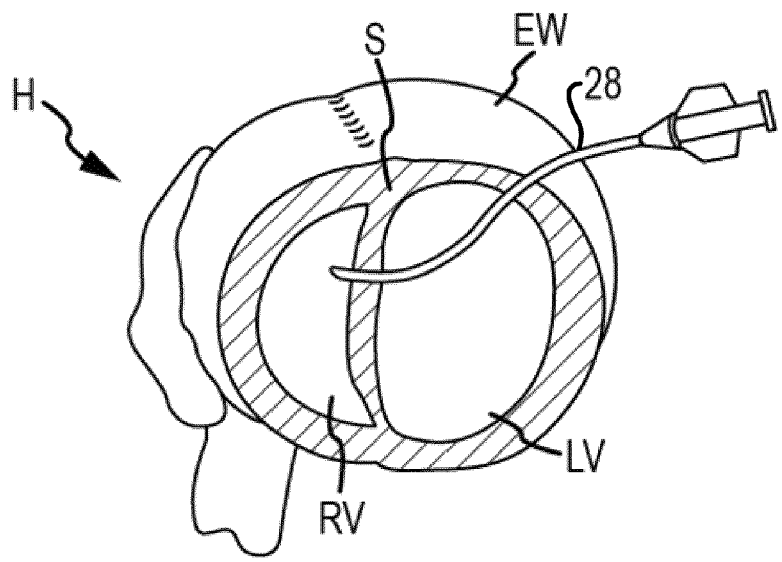
FIGS. 3B and 3C schematically illustrate a needle and guidewire crossing one chamber of a heart and being inserted into another chamber.
Figure 3C:
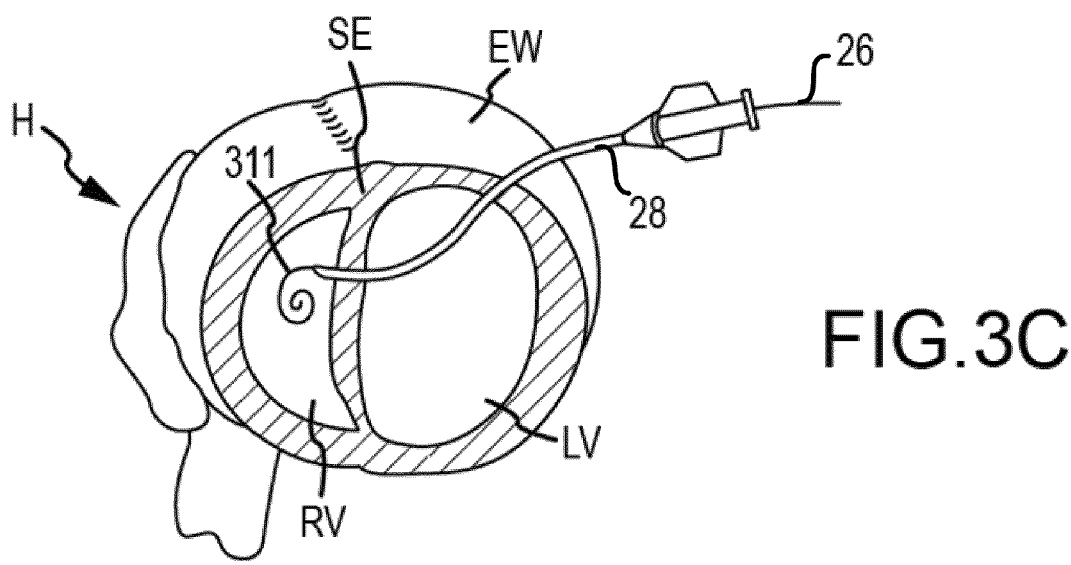

Referring now to FIGS. 3B and 3C, still further alternative approaches can be used for perforating the external wall EW and septum S of heart H via an epicardial approach so as to form an epicardial access path. In this embodiment, a rigid or semi-rigid curved needle 28 is advanced through the left ventricle external wall and septum, and guidewire 26 is advanced through the working lumen of needle 28. A plurality of needles of different curvatures may be used to form the access pathways associated with the different implants of an implant system, optionally through an open surgical approach, a mini-thoracotomy, or the like. Still further alternatives may be employed, including robotic insertion and/or steering of a heart tissue penetrating tool.

Figure 4C:
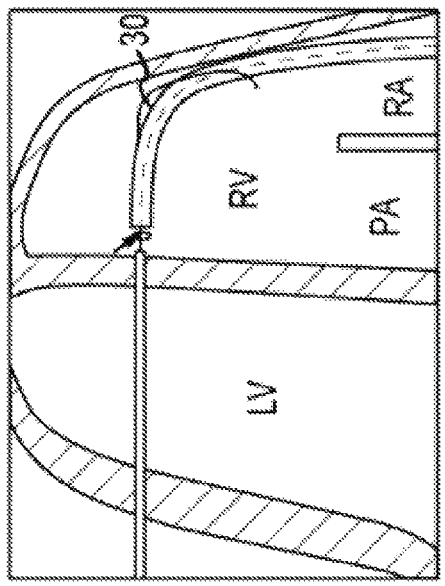
FIGS. 4A-4C schematically illustrate joining a right atrial access tool shaft with an endoscopic trans-epicardial access tool shaft within the right ventricle by coupling a guidewire and snare advanced along the shafts and into the right ventricle.
Figure 4A:
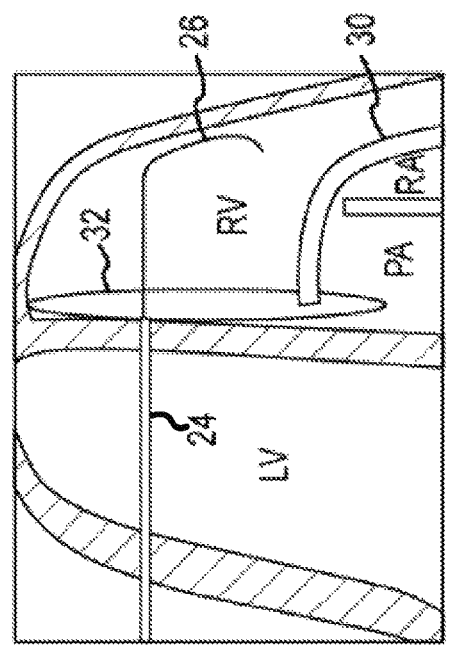
Figure 4B:
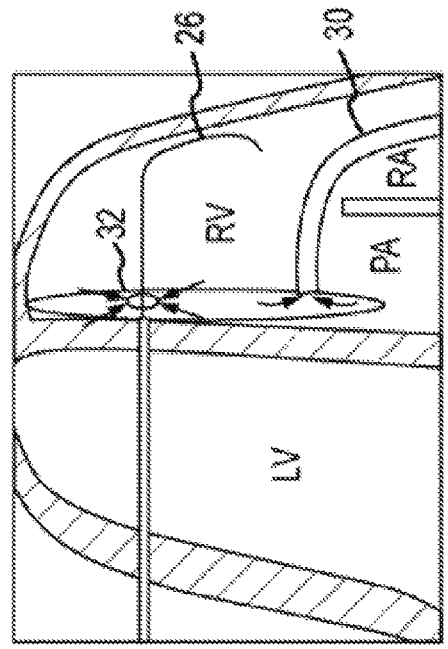

Referring now to FIGS. 4A-4C, a distal end of catheter 30 may be advanced to the right ventricle RV through the right atrium RA and associated vasculature using known techniques, so that catheter 30 provides a right ventricle access tool. Optionally, a snare tool has a distal portion configured to engage a distal portion of the guidewire. For example, distal snare 32 may be separated from a proximal end of a snare body by sufficient length of the snare body to allow the snare to be manipulated within the right ventricle from the proximal end of catheter 30. Snare 32 may be biased to open when advanced beyond catheter 30, allowing the catheter to be positioned near the septum around the epicardial path of catheter 24. Advancing guidewire 26 through the opening of snare 30 and withdrawing snare 32 into catheter 32 so that the guidewire is bent as it enters the distal end of catheter 30 axially couples the guidewire to the snare.

Figure 5A:
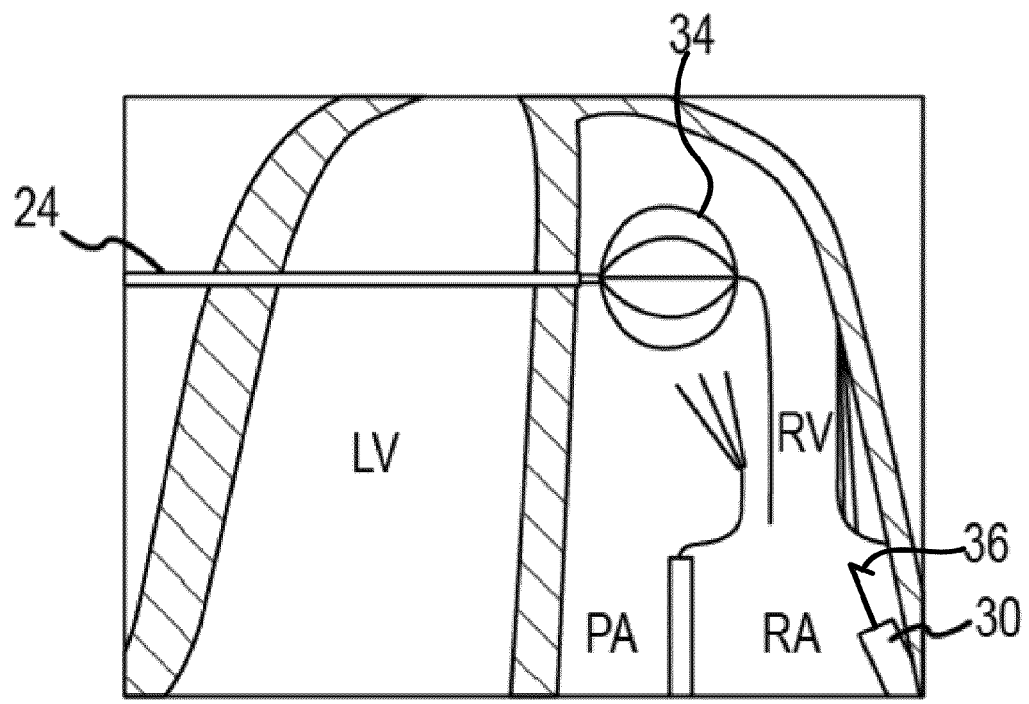
FIGS. 5A and 5B schematically illustrate alternative techniques for joining a right atrial access tool shaft and an endoscopic epicardial access tool by snaring a guidewire within the right ventricle or right atrium of the heart using a basket snare.
Figure 5B:
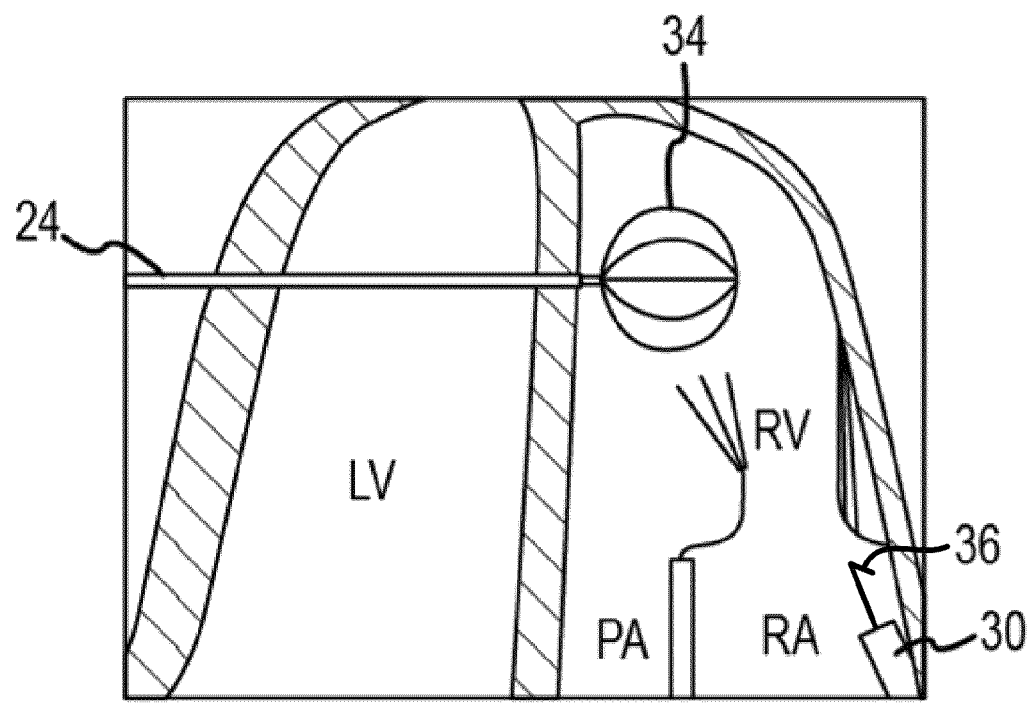
Figure 6:
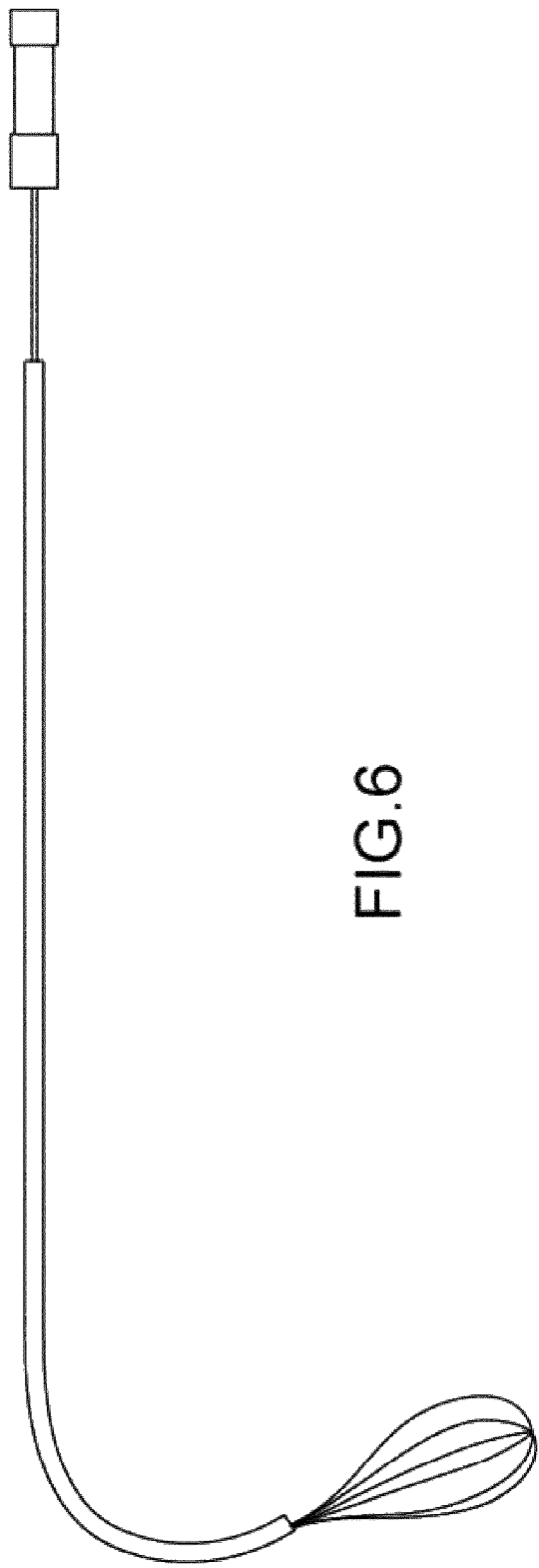
FIG. 6 illustrates a basket snare and associated access catheter configured for use in the right ventricle.

Referring now to FIGS. 5A and 5B, there may be advantages to employing alternative elongate flexible bodies to couple the access paths within the heart. For example, a guidewire-like elongate body with a proximal end and a distal portion formed as a basket 34 may be expanded in the right ventricle so that the basket encompasses a volume within the right ventricle. In some embodiments, the basket may be withdrawn back into catheter 24 or 30 so as to capture a guidewire extending from the other, thereby joining the paths. In other embodiments, a guidewire-like elongate flexible body 36 having short lateral distal protrusion or barb can be advanced a relatively short distance into a target portion of the basket and withdrawn back into the catheter so as to capture a member of basket 34, with the target portion of the basket being separated from sensitive heart tissues (such as valve leaflets or chordae) by the expansion of the basket. Optionally, the basket 34 may be advanced toward or into the right atrium before engaging the basket with the distal portion of flexible body 36. An exemplary basket structure and associated access catheter are shown in FIG. 6.

Figure 7:
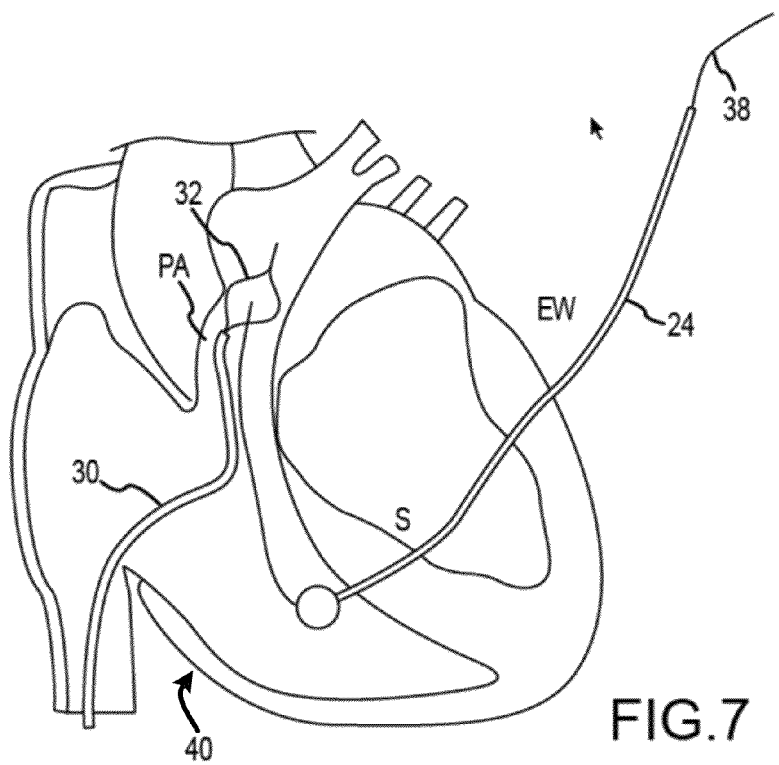
FIG. 7 schematically illustrates joining a right-atrial access tool path with a trans-epicardial access tool using a snare and associated guidewire configured for coupling within the pulmonary artery.
Figure 8:
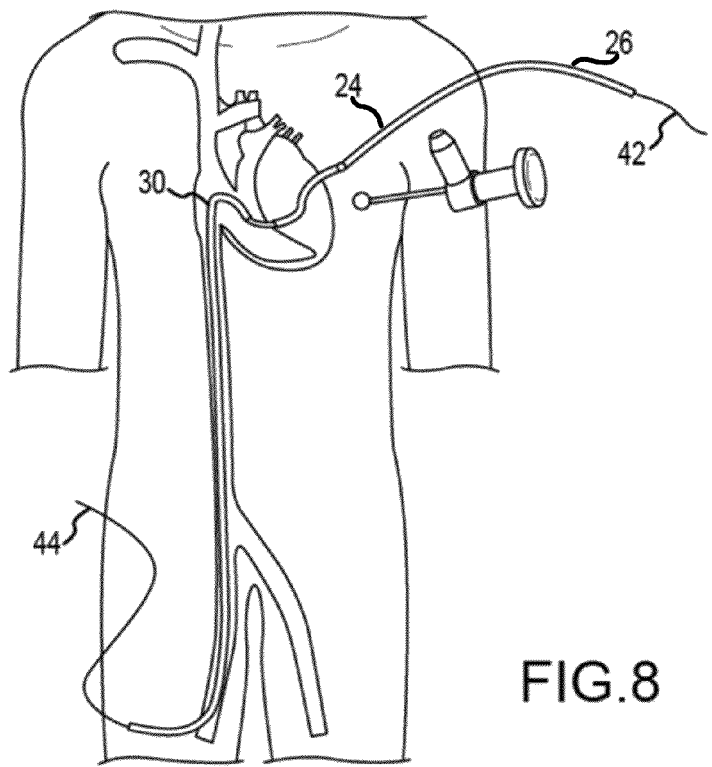
FIG. 8 schematically illustrates a guidewire that has been pulled along paths joined within the right ventricle so as to extend from outside the patient, through the right atrium, through the right ventricle, through the septum, through the left ventricle, through an exterior wall of the heart, and back outside the patient.
Figure 9A:
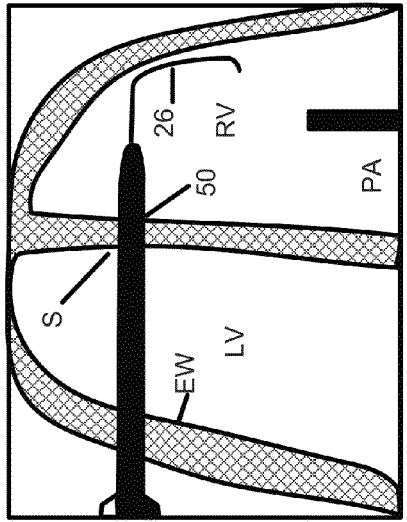
FIGS. 9A-9C schematically illustrates expansion of a path through the left ventricle over a guidewire, delivery of an anchor and adjacent tension member through the expanded path and over the guidewire, and controlling movement and orientation of the anchor within the right ventricle using a guidewire extending along a joined path.
Figure 9B:
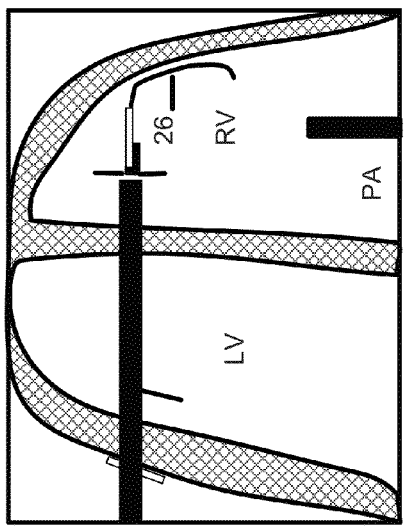
Figure 9C:
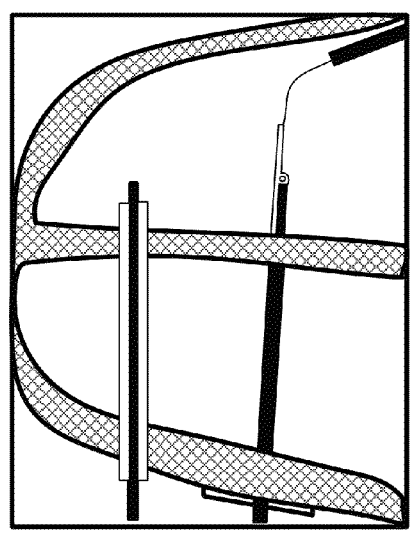

Referring now to FIG. 7, still alternative distal end portions may be used to help couple the flexible bodies advanced into the heart via the right atrial and epicardial access paths. In this embodiment, catheter 30 is advanced through the right atrium and the right ventricle to the pulmonary artery PA. Snare 32 is expanded in the pulmonary artery PA. A distal balloon 40 mounted to a flexible tubular body 38 is advanced through catheter 24 into the right ventricle. Balloon 40 is inflated from a distal end of the flexible body 38 via an inflation lumen of the flexible body, and the balloon is allowed to flow with the blood of the heart into a pulmonary artery PA. The balloon is captured by the snare. Note that the access catheter 24, 30 associated with the various flexible bodies described above may be switched, so that (for example) balloon 40 may be advanced through catheter 30 along the right atrial access path, while snare 32 may be advanced along catheter 24 along the epicardial approach. Regardless of the specific end portions of the flexible bodies employed to axially couple the flexible bodies, coupling of the pathways allows guidewire 26 to be inserted into the body along one of the paths and withdrawn out of the body from along the other path so that both a first end 42 and a second end 44 of the guidewire are disposed outside the heart and the patient. The result is the guidewire extending from a first end disposed outside the patient, into the right ventricle of the heart along the epicardial access path, and back out of the heart and the patient through the left ventricle along the epicardial access path, as shown in FIG. 8.

Referring now to FIGS. 9A-10F, deployment of the implant over guidewire 26 may optionally include advancing an anchor through external wall EW and/or septum S. While guidewire 26 is shown terminating in right ventricle RV in FIGS. 9A and 9B for simplicity, many or all of the steps described below may be performed after joining of the access paths so that the guidewire extends out of the heart through the right atrium. A dilation catheter 50 with a tapered helical distal end 52 can be advanced over guidewire 26 along the epicardial path, and can be rotated from a proximal end 54 to screw the distal end into and through the septum from outside the patient, with rotation of catheter 50 optionally being transmitted axially over guidewire 26 around a curve. Rotation of helical end 52 may help advance catheter 50 with less axial force than would be used to axially advance a tapered catheter, and may limit axial force to the septum sufficiently to inhibit arrhythmia of the heart. Once the path through the septum has been dilated, dilation catheter 50 can be withdrawn over guidewire 26 and a distal end 62 of a grasping catheter 60 can be advanced along the epicardial path over guidewire 26. Grasping catheter 60 has deployable arms 64 which can be withdrawn into a body 66 of the catheter during insertion, and can be extended axially and laterally out of the end of catheter body 66 to a deployed configuration (as shown) by actuation of a proximal handle 68 from outside the patient. A variety of alternative axial grasping structures might also be used, including malecot structures, torroidal balloons, or the like. Regardless, once distal end 62 of grasping catheter is disposed within the right ventricle, arms 64 are deployed and the catheter can be pulled proximally to engage the arms against the septum and facilitate deployment of the septal anchor.

Referring now to FIGS. 10G-10I, and alternative dilation catheter 50' may have a tapered helical distal end 52' that is configured to rotationally advance or screw into and through tissue. Inner and outer concentric shafts extend proximally of distal end 52 toward a proximal hub 51. The shafts are laterally flexible to accommodate curvature of the axis of the dilation catheter, and the hub and tip may be axially coupled to the inner shaft and the inner shaft may be sufficiently axially stiff so that rotation of the hub outside the body induces controlled rotation of the tip into and through the tissue while the outer shaft remains rotationally stationary.

Referring now to FIGS. 9B, 10, 10A, 10F, and 12A, the end of the guidewire extending out from the epicardial access path is threaded through a lumen of an anchor delivery 70 from a distal end of the delivery catheter and out the proximal end. The same guidewire end can then be inserted through an axial anchor lumen 80 through anchor 12 and with the anchor aligned along tether 16, the anchor 12 can be loaded into the proximal end of an anchor delivery catheter 70 over guidewire 26 with tether 16 trailing behind the anchor. A pusher catheter 72 can be positioned proximally of the anchor within delivery catheter 70 to push the anchor distally. The delivery catheter can be advanced along the epicardial access path over guidewire 26 so that the distal end of the delivery catheter extends into the right ventricle. Optionally, a loading cartridge 82 may facilitate insertion of anchor 12 into delivery catheter 70. Anchor 12 can then be advanced out of the distal end of delivery catheter 70 by pushing the anchor distally with pusher 72. Guidewire 26 helps maintain a position and orientation of the anchor within the right ventricle, particularly when the guidewire extends along the coupled access paths.

The anchor may optionally be advanced into and/or within the heart by pushing the anchor distally using a flexible compressive shaft of pusher catheter 70 (shown in FIG. 10F), grasping catheter 60 (shown in FIGS. 10B and 10C), or the like. In either case, the compressive shaft being used as a pusher catheter may have separate lumens for the guidewire and tension member as shown, with both lumens extending between the distal anchor-pushing end and the proximal end of the catheter body. More than 2 lumens may also be provided, and the multi-lumen structure can enhance rotational control over the anchor about the axis of the tension member, and/or may facilitate orienting the arms of the anchor by rotating of the pushtube (optionally along with the tension member and guidewire therein) from outside the patient. In some embodiments, the tether may have an elongate cross-section and the pusher catheter which receives the tether may have a corresponding elongate cross-section so as to enhance rotational control over the advanced anchor after the guidewire is pulled free of the anchor, as can be understood with reference to the distal end of grasper catheter 60 shown in FIG. 10C, and with reference to the elongate cross-section of the large tether lumen of pusher catheter 70 in FIG. 10F. One or more of the smaller lumens may be sized to receive the guidewire.

Figure 11A:
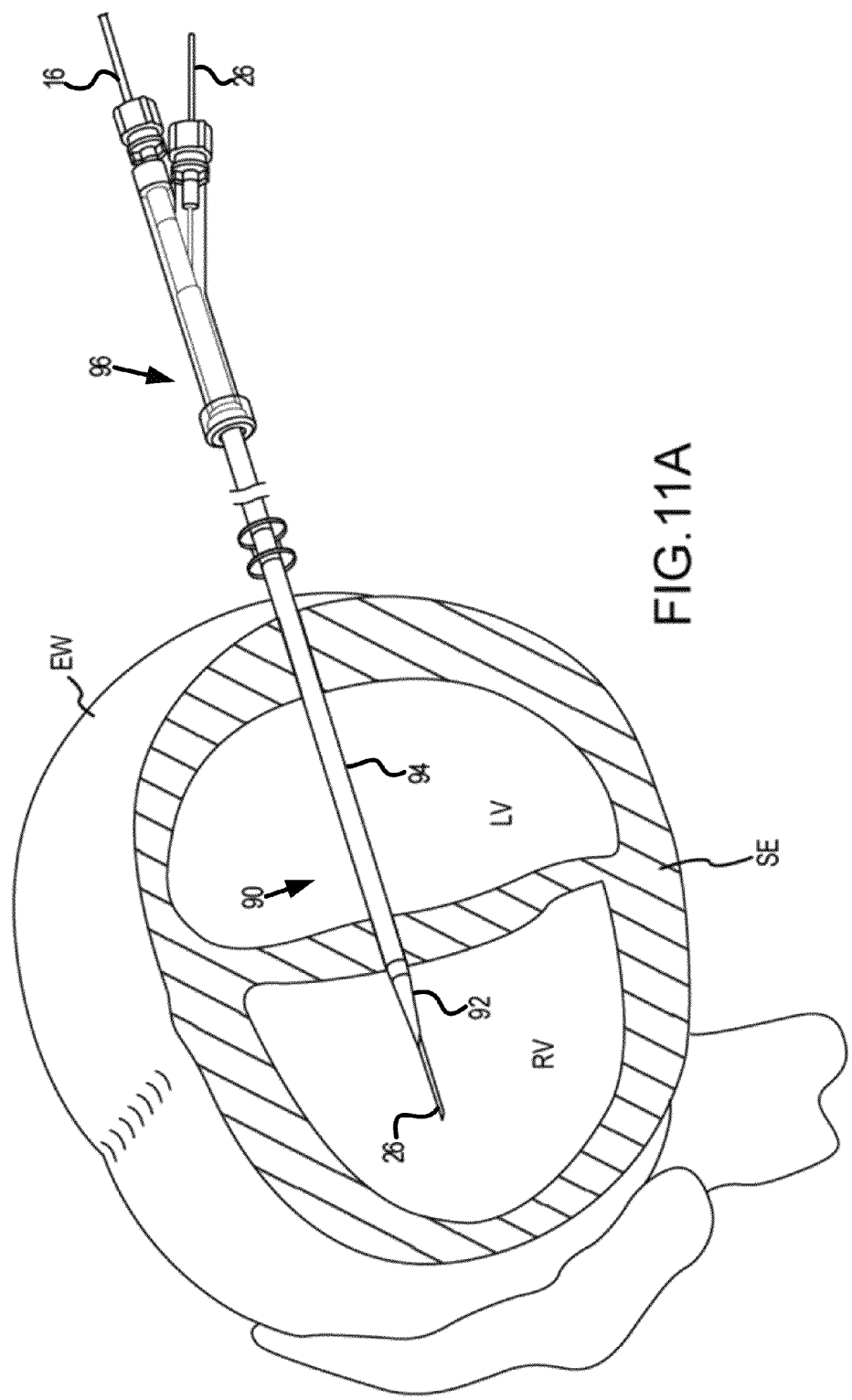
FIGS. 11A-11C illustrate an alternative over-the-wire dilating catheter
Figure 11B:
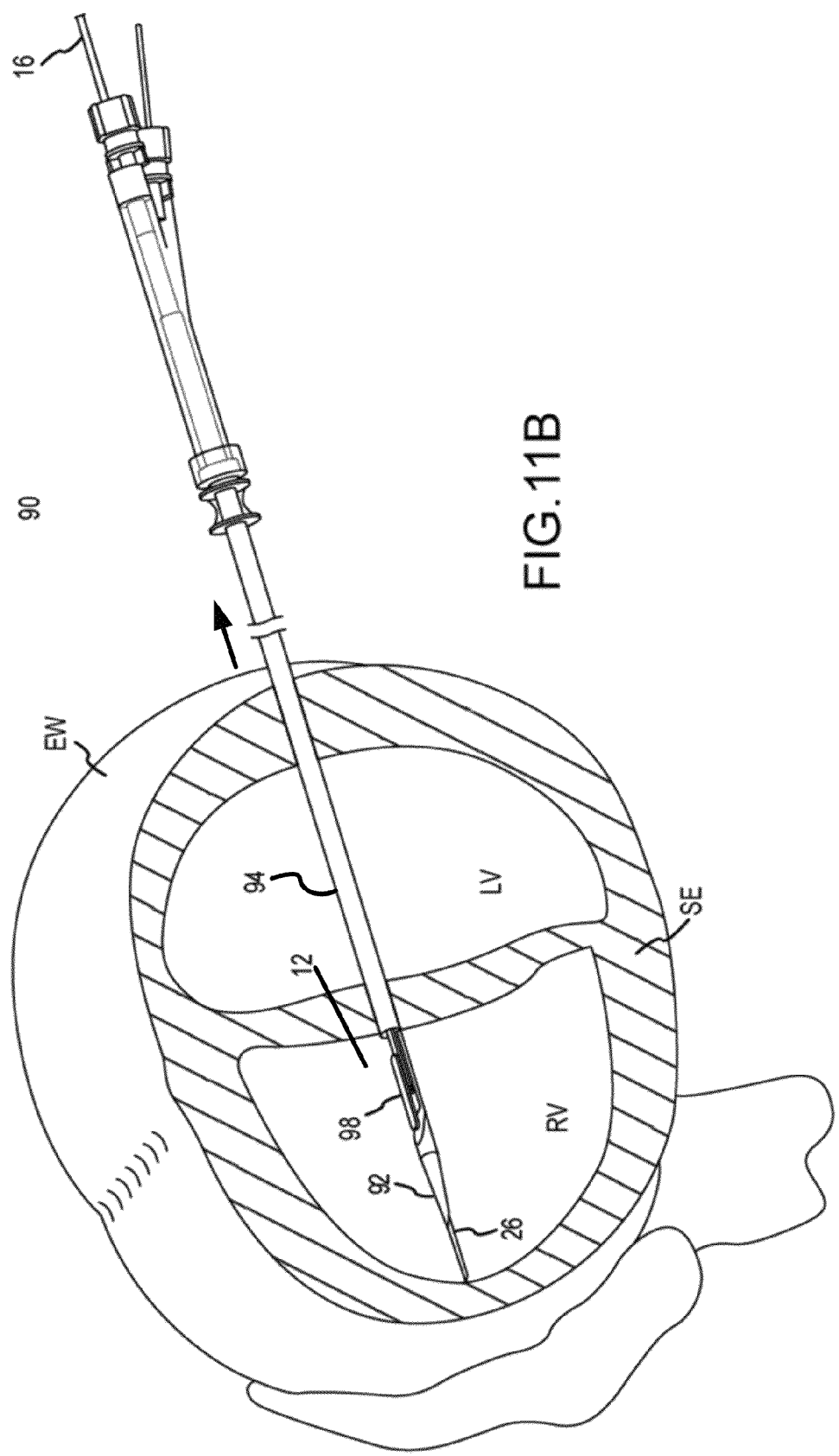
Figure 11C:
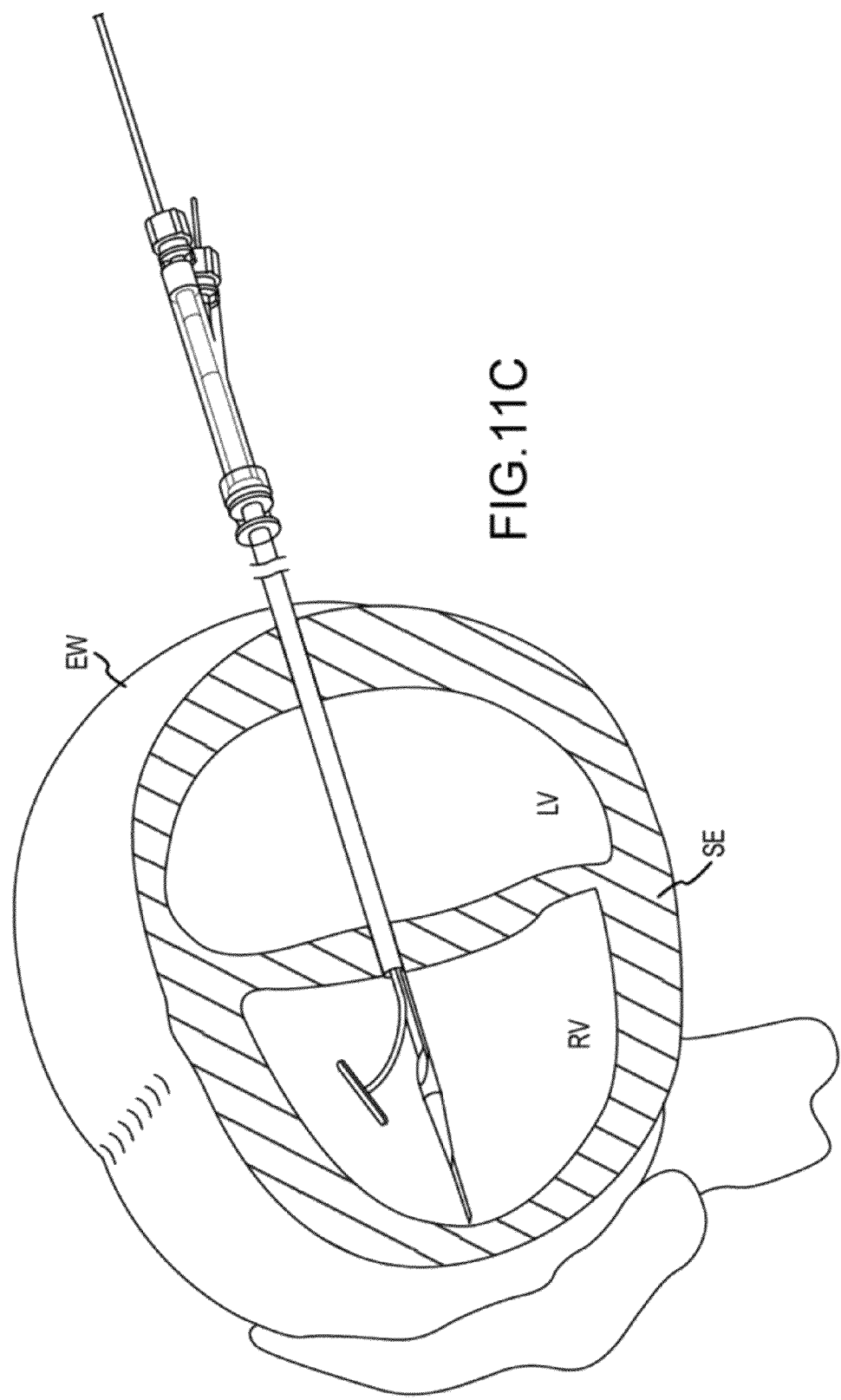
Figure 12A:
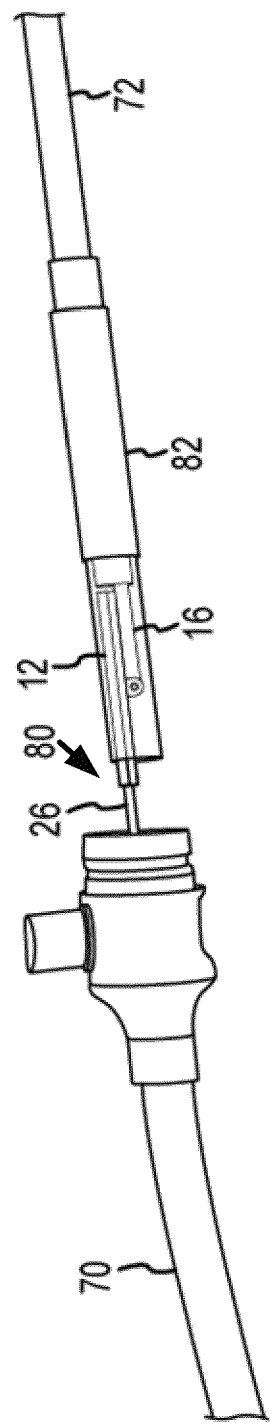
FIGS. 12A-12D schematically illustrate introducing an implant into an over-the-wire delivery catheter, advancing the implant into the heart along the epicardial access path, and deploying the implant within the right ventricle.
Figure 12B:
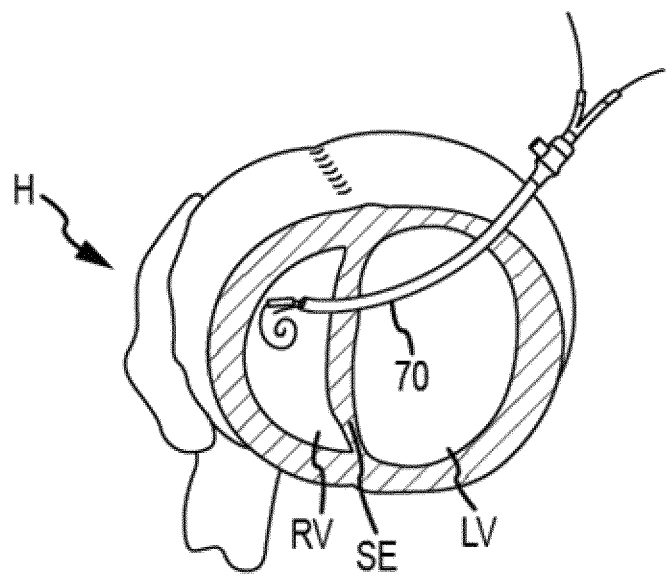
Figure 12C:
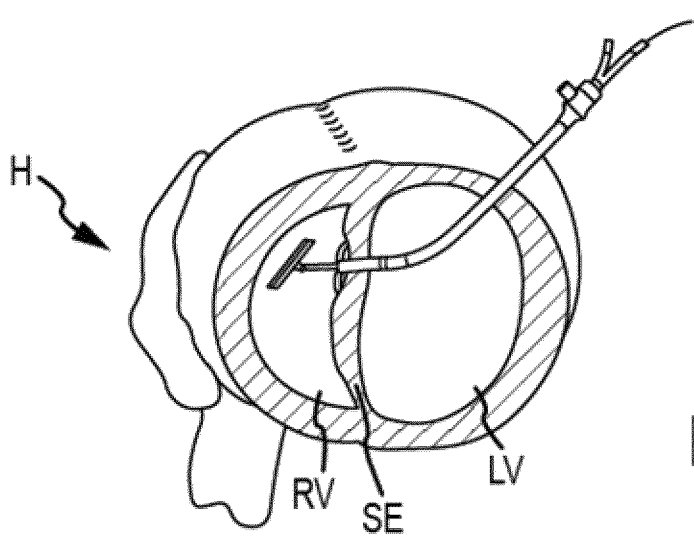
Figure 12D:
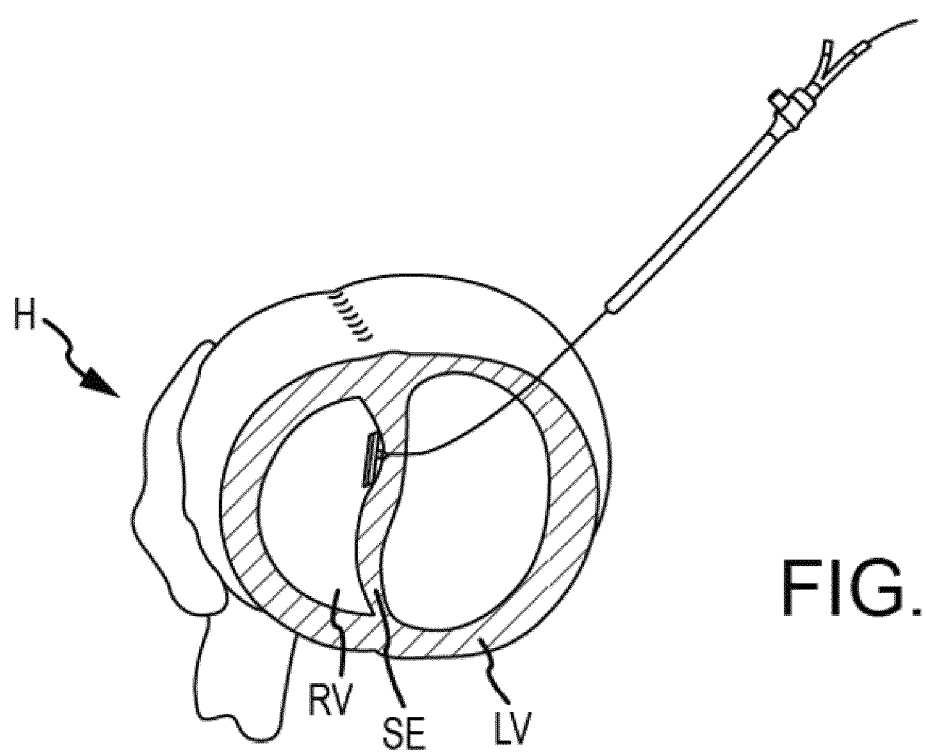
Figure 13A:
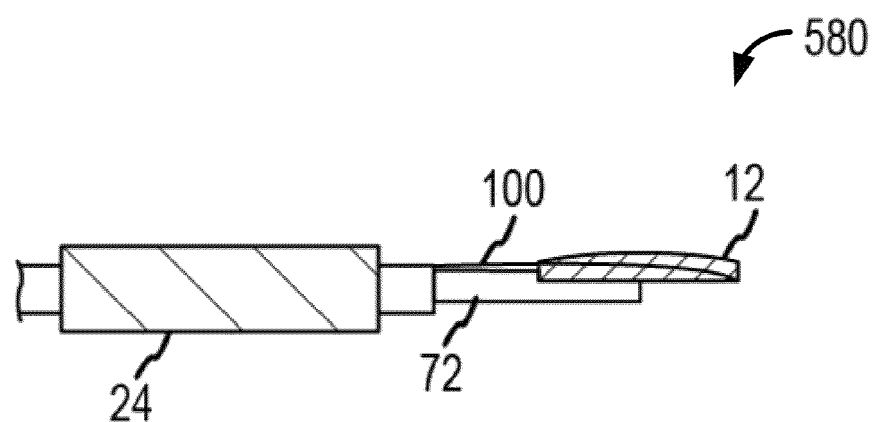
FIGS. 13A and 13B schematically illustrate an anchor repositioning leash and its use.
Figure 13B:
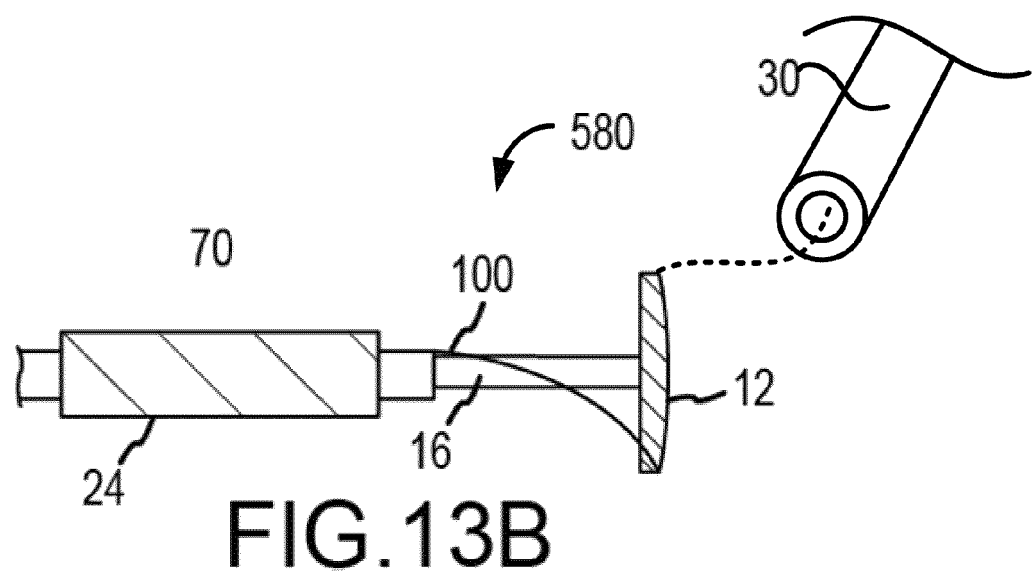
Figure 14C:
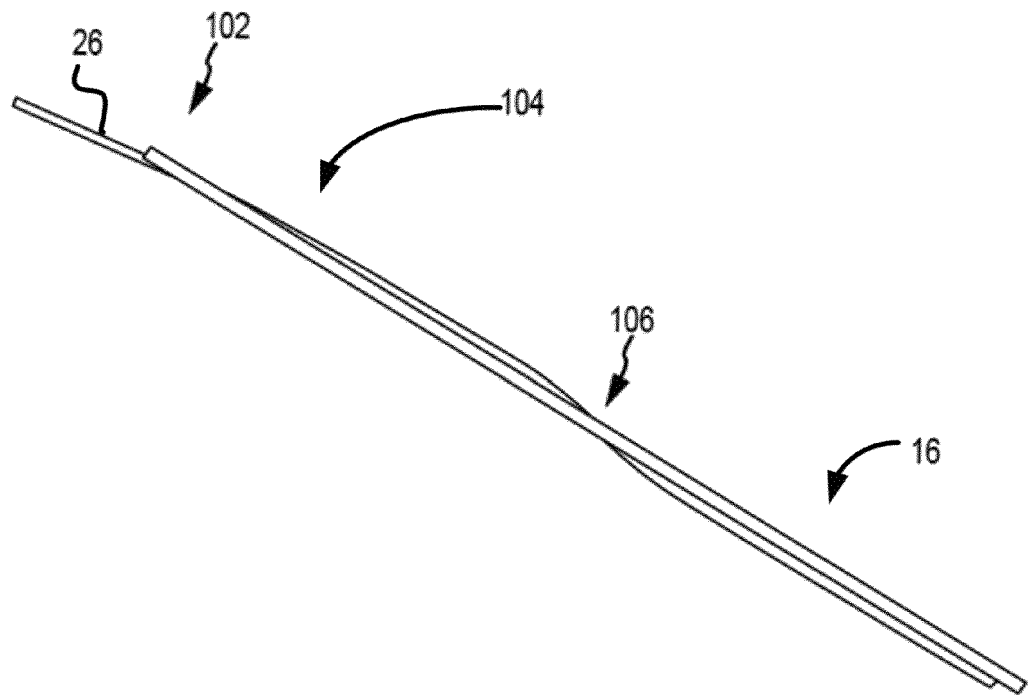
Figure 15A:
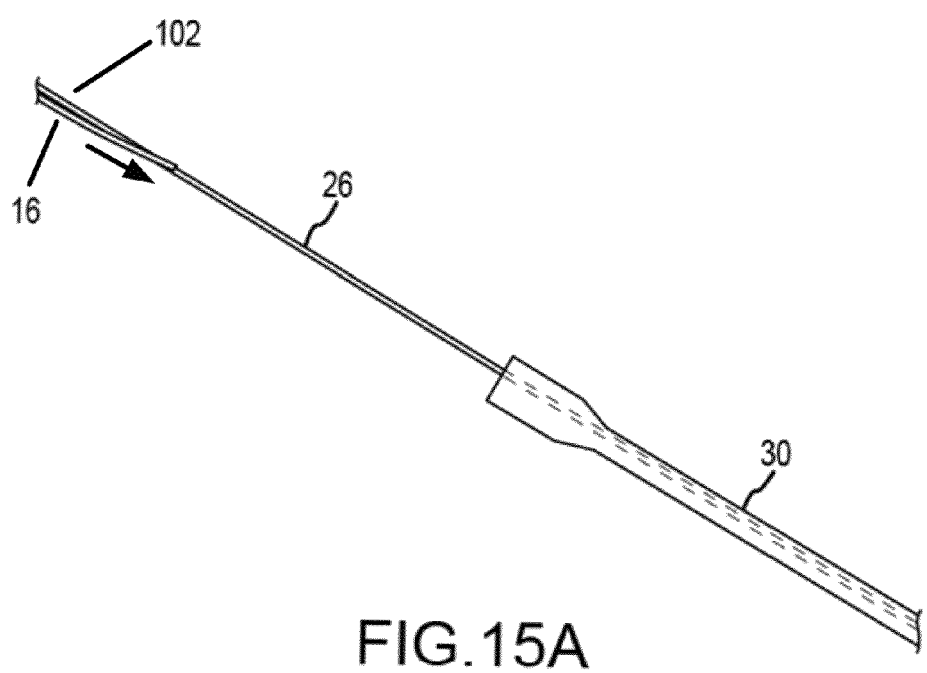
FIGS. 15A-15C schematically illustrate advancing the tension member and anchor along a right ventricle access tool over a guidewire, and out from the access tool and through the septum and an external wall of the left ventricle.
Figure 15B:
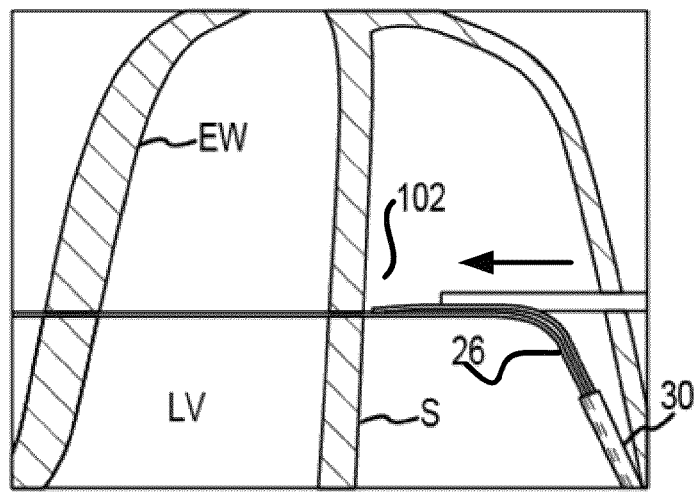
Figure 15C:
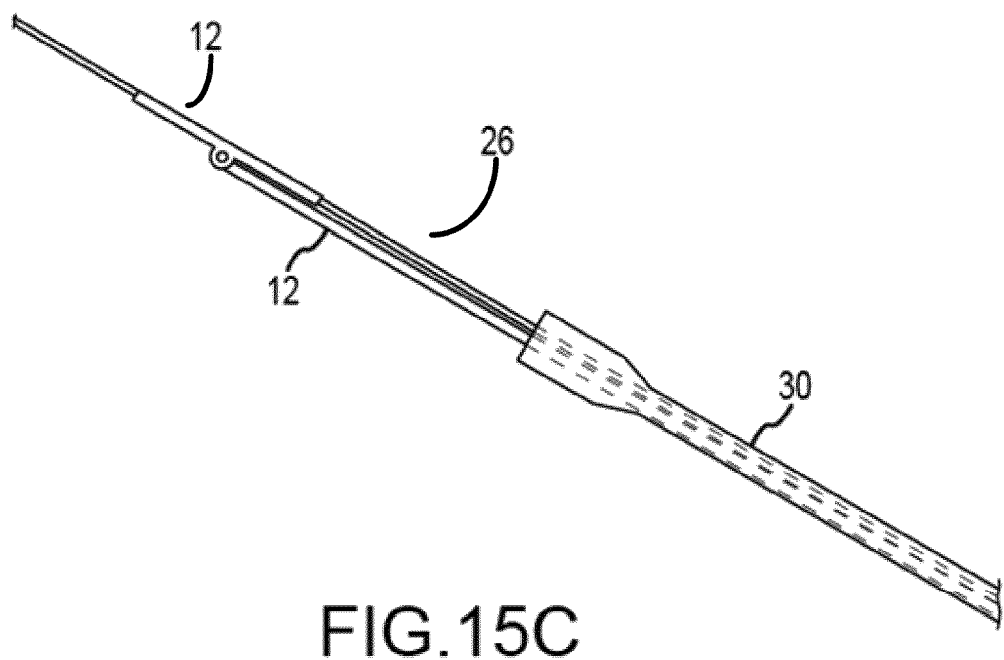
Figure 16B:
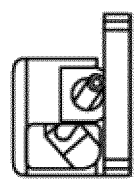
FIGS. 16A-16D illustrate an epicardial anchor.
Figure 16A:
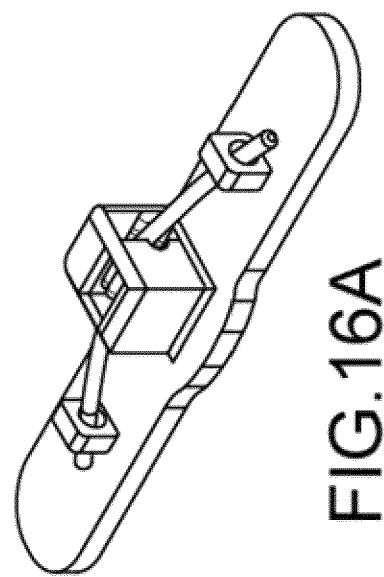
Figure 16C:
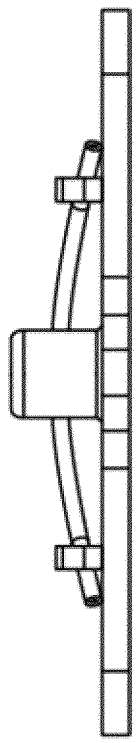
Figure 16D:
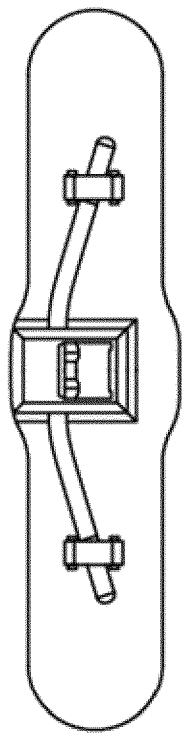
Figure 17:
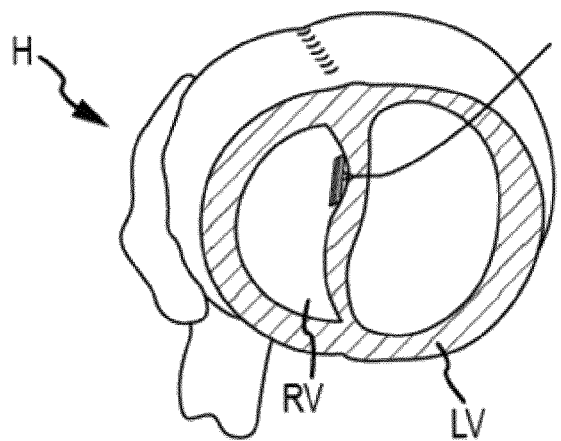
FIGS. 17-21 schematically illustrate imposing a desired anchoring force while an epicardial anchor is in a variable-force mode, and reconfiguring the epicardial anchor to a set force mode so as to maintain engagement between the septum and the external wall of the beating heart within a desired range.
Figure 18:
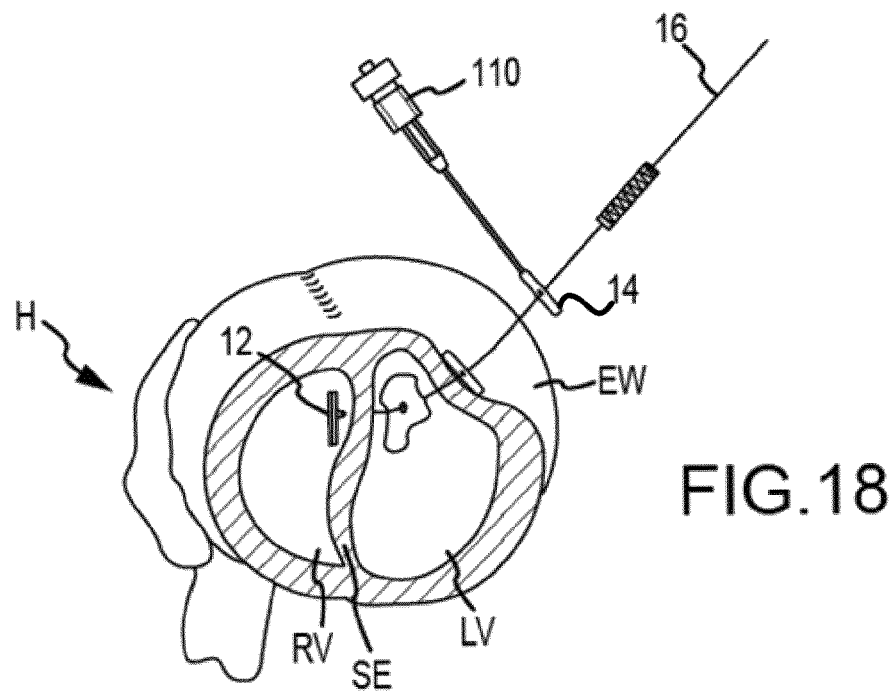
Figure 19:
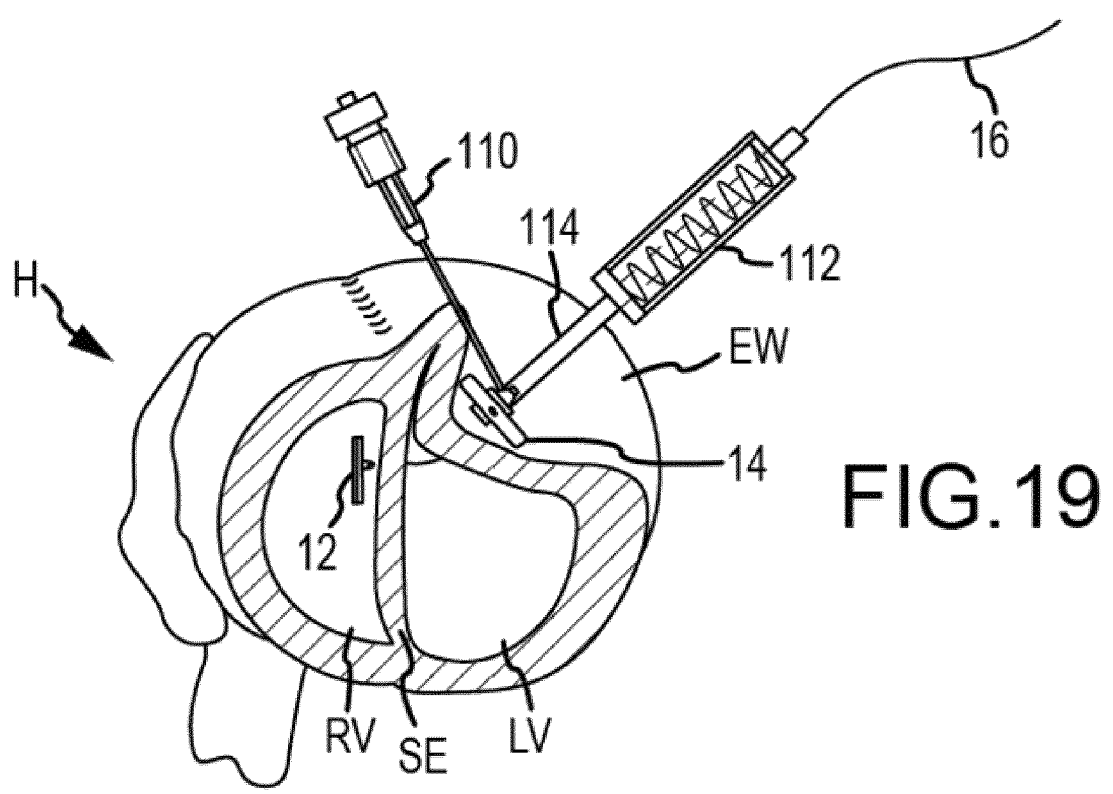
Figure 20:
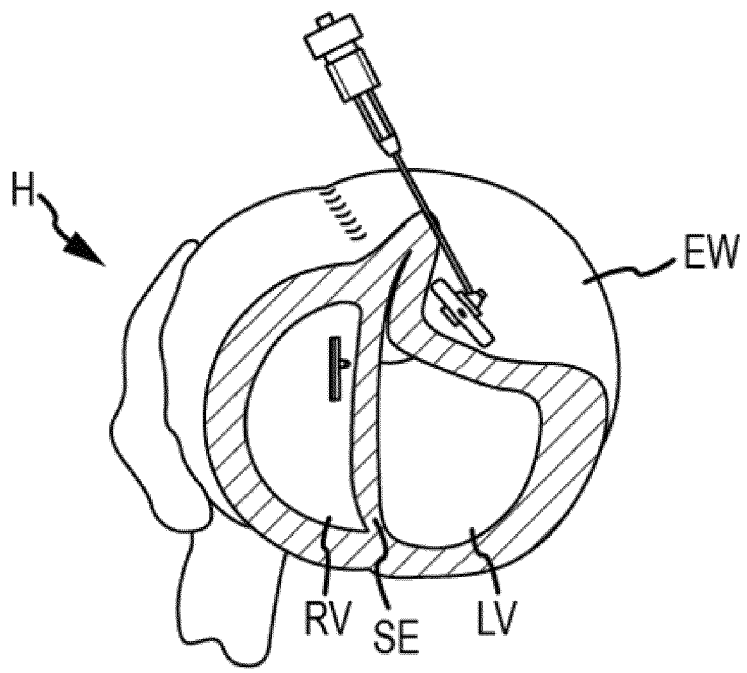
Figure 21:
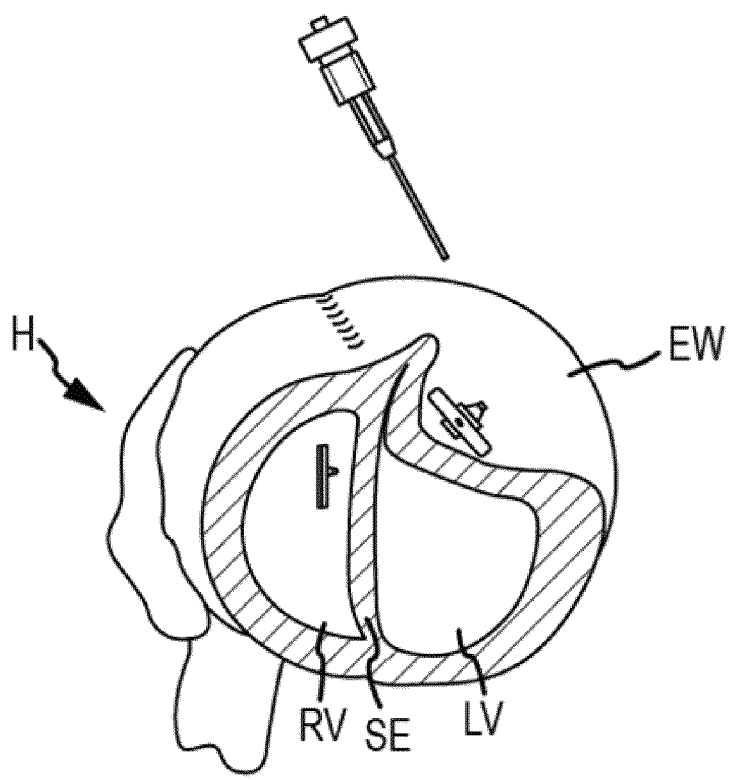
Figure 22A:
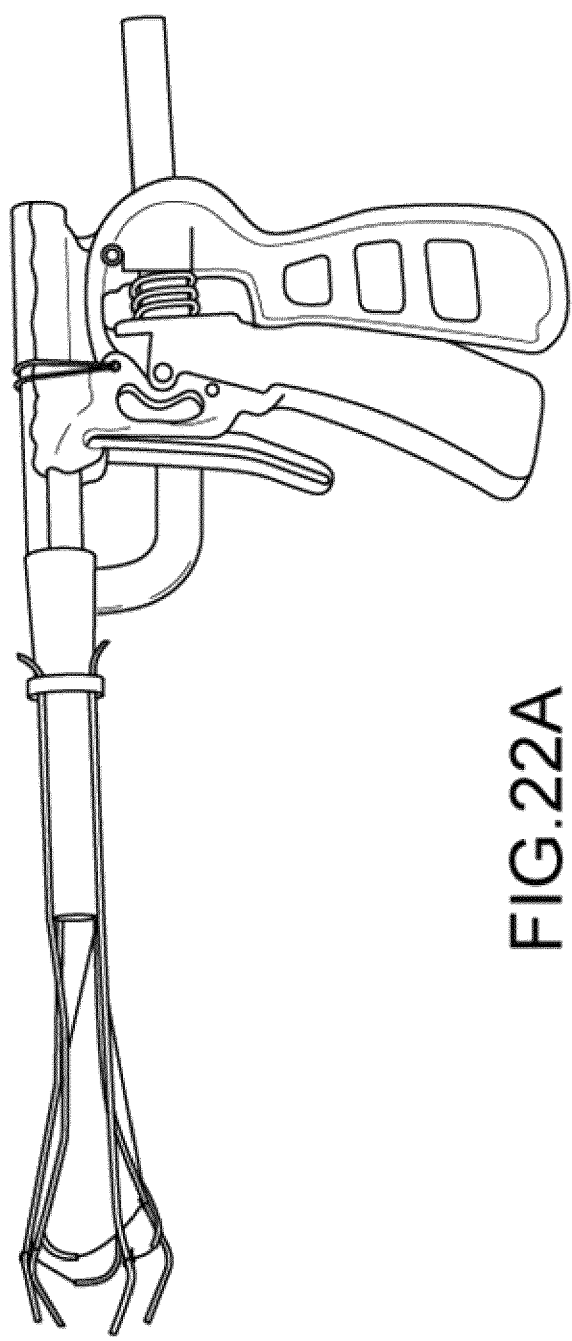
FIGS. 22A-22D illustrate an epicardial hemostasis tool having a working lumen to provide access through a tissue tract to a epicardium about an epicardial access path, wherein the tool is configured to compress the external wall of the heart toward the access path so as to provide hemostasis.
Figure 22B:
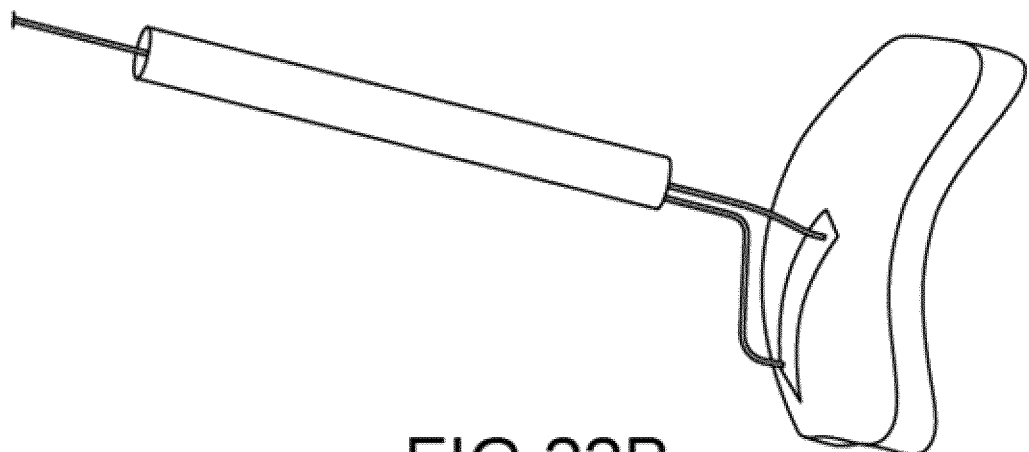
Figure 22C:
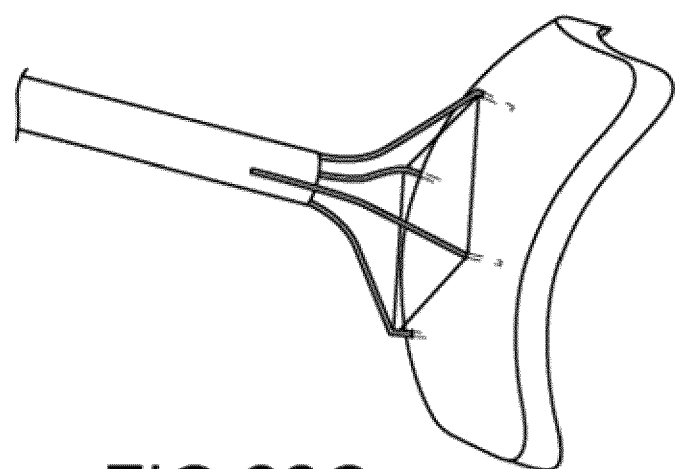
Figure 22D:
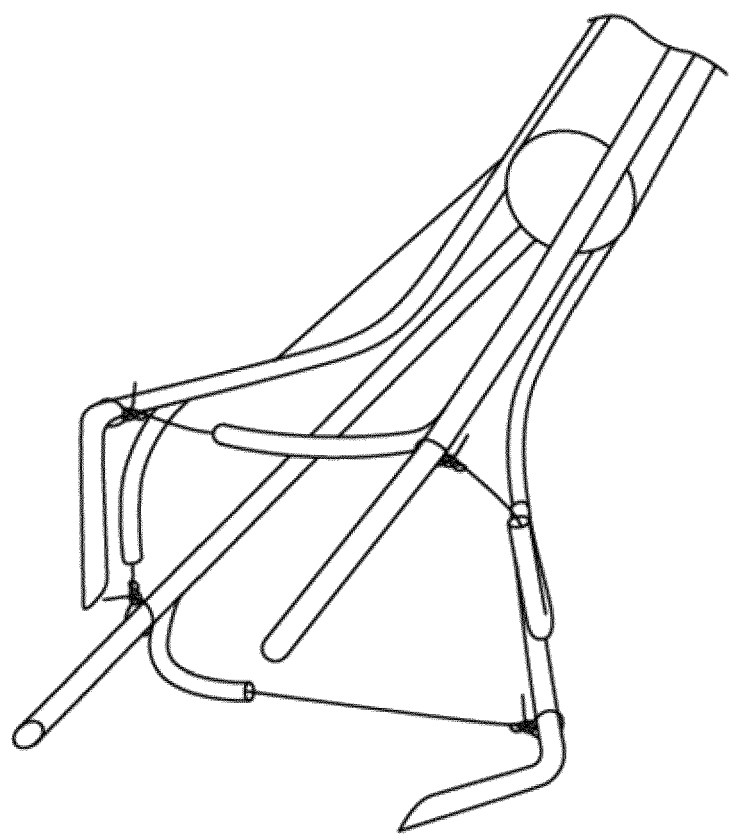

Referring now to FIGS. 11A-11C, an alternative over-the-wire delivery catheter 90 has a dilating distal tip 92 and a sheath 94 that can be withdrawn from the distal tip from a proximal handle. When sheath 94 is retracted proximally, anchor 12 is laterally released from a receptacle 98 of delivery catheter, allowing catheter to be withdrawn from the access path once guidewire 26 has been removed.

Referring now to FIGS. 12D-13B, once anchor 12 is disposed within right ventricle RV and beyond delivery catheter 70, guidewire 26 can be removed and the anchor can be positioned transverse to tether 16 by engagement between the anchor and the surface of the septum, or by pulling on a leash 100 extending through catheter 24 or catheter 30. Radial positioning of anchor 12 can be provided by rotating the end of tether 16, which remains outside the patient.

Referring now to FIGS. 14A-15C, alternative embodiments of the systems may be configured to deliver septal anchor 12 to the right atrium along the right atrial path, typically with the anchor trailing behind tether 16. An end 102 of tether 16 is generally disposed opposite of anchor 12, and may include features to maintain the tether in alignment along the guidewire, and may also axially couple the tether to the guidewire. For example, a channel such as angled channel 104 may receive the guidewire therein, allowing the tether to be pushed axially over the guidewire. One or more additional channels 106 through tether 16 toward anchor 12 from end 102 may help limit bowing of the tether away from guidewire 26 when the tether is pushed axially over the guidewire. As can be understood with reference to FIGS. 15A-15C, end 102 of tether is advanced over guidewire 26 and into a proximal hemostasis valve of catheter 30. By continuing to push tether 16 into catheter 30, and/or by pulling guidewire 26 from the end extending from the epicardial path, end 102 of the tether may be advanced into and through the septum S and external wall EW so that end 102 is disposed outside the heart and the patient. Optionally, the tether may be advanced along the epicardial path alongside guidewire 26. In other embodiments, catheter 30 or another catheter body may be advanced over the guidewire with the tether disposed in a lumen.

Referring now to FIGS. 10, 10D, 10E, and 16A-21, epicardial anchor 14 has a spring cam structure as more fully described in US Patent Publication No. US2010/0016655, as published on Jan. 21, 2010 and entitled "Cardiac Anchor Structures, Methods, and Systems for treatment of Congestive Heart Failure and Other Conditions;" the full disclosures of which are incorporated herein by reference. The spring cam allows anchor 14 to slide along tether 16 toward anchor 12, but inhibits sliding of anchor 14 away from anchor 12, so that the spring cam can effective maintains a tissue engagement force between the anchors. This set-force interaction between the tether and anchor 14 is advantageous once the proper force is applied, but it can be challenging to apply the desired force when the heart is beating. To more accurately apply septal/external wall engagement forces within a desired range, an anchor set tool 110 can engage the cam spring mechanism of anchor 14 so as to allow the anchor to slide both axial directions along tether 16, thereby configuring anchor 14 into a variable force mode. This allows a controlled force to be applied between the tether 16 and epicardial anchor 14 despite beating of the heart, with the force preferably being applied by a force application tool 112 having an elongate shaft 114. Force application tool 14 may be a relatively simple structure similar to a scale, typically having a force spring and an indicator showing when a force in a desired range is being applied such as by showing deflection of the spring to a position within a desired range. By sliding the shaft of the force application tool over tether 16, engaging the surface of anchor 14 with a compression surface of the shaft, and applying force between the tether and the force application tool till the desired deflection is identified the desired force may be applied between anchors 12 and 14. While that force is applied, anchor set tool 110 may disengage the cam lock of epicardial anchor 14, thereby reconfiguring the anchor from the variable-force mode to the set-force mode. The force application tool 112 and anchor set tool 112 can then be removed, the tether 16 extending away from the heart from epicardial anchor can be cut and removed. Pressure by epicardial anchor 14 against external wall 14 inhibits blood flow out of the left ventricle along the epicardial access path, while pressure of septal anchor 12 against the septum inhibits blood flow from the left ventricle to the right ventricle. Known techniques can be used for closure of the vascular access of catheter 30 and the minimally invasive access to the epicardium.

Referring now to FIGS. 21A-21D, a variety of minimally alternative anchor locking structures and access methods may be employed to decrease collateral tissue trauma when applying the controlled anchoring force, some of which will be described below. Such minimally invasive anchor locks may benefit from a tissue-engagement component that distributes anchoring loads laterally between anchors so as to promote apposition of the walls of the heart along a desired contour and help provide the desired ventricular shape after implantation of a multi-anchor implant system. Toward that end, a folding anchor component 111 may comprise an at least substantially rigid elongate body having a passage traversing therethrough, with a channel extending along opposing surfaces of the body from the aperture. One of the channels may optionally extend through the body, allowing the body to be advanced laterally over tether 111 so that the tether extends through the body at the passage. Other embodiments may employ passages in the form of apertures, so that the tether is passed axially through the passage. Regardless, the channels receive the tension member so that the anchor component 111 can pivot toward axial alignment with tension member 16, along the anchor component to be advanced over tether 16 through a working lumen of an access tool or sheath 113, as shown in FIG. 21B. Once anchor component 111 is distal of sheath 113 and proximal of the epicardial surface of the heart, the anchor component 111 can be pivoted relative to the tension member and slid distally along the tension member into engagement with the epicardial surface, as shown in FIGS. 21C and 21D. A relatively small profile (as compared to the pivoted component 111) locking anchor component can then be advanced axially over the tension member through the sheath and into engagement with the anchor component 111 so as to provide the desired anchoring force. Anchor component 111 may comprise a metal or high-strength polymer structure, such as a stainless steel, a Nitinol shape memory alloy, PEEK, or the like.

Referring now to FIGS. 22A-22D, an epicardial access tool may facilitate both access to the epicardium and hemostasis of the epicardial access path. A shaft of the epicardial access tool extends from a proximal handle to a circumferatial series of distal radial compression features. A working lumen of the access tool shaft allows the various access tools to be advanced along a tissue tract from outside the patient to an epicardial surface region encompassing the epicardial access path. The compression features are oriented to engage tissue of the external wall and urge the engaged tissue radially inwardly when the handle is actuated. In the exemplary embodiment, filaments extend axially from the handle along the shaft to each compression feature, and then turn laterally from that compression feature to another compression feature. Actuation of the handle pulls the filaments, thereby pulling the compression features radially inwardly. Alternative epicardial access tools may employ suction to grip and stabilize the epicardial surface of the heart, somewhat analogous to the engagement between known heart stabilization tools and the heart as used for beating-heart coronary arterial bypass grafting and the like.

Figure 24:
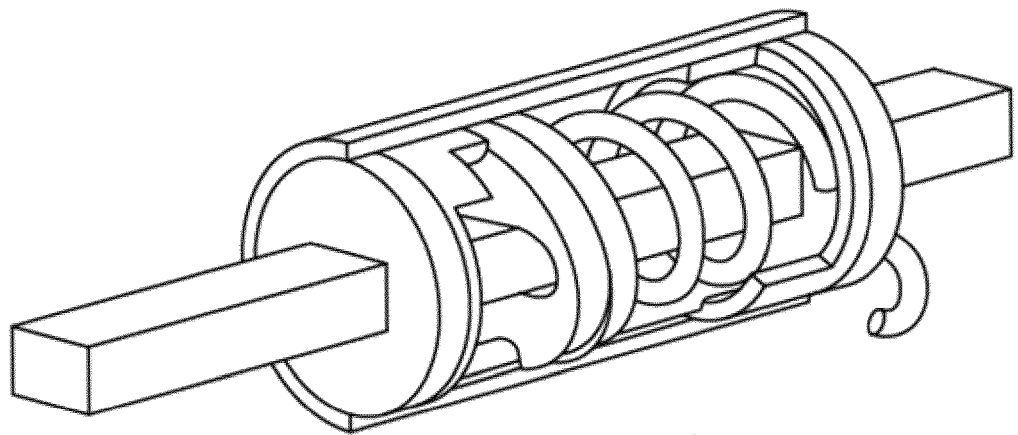
Figure 24A:
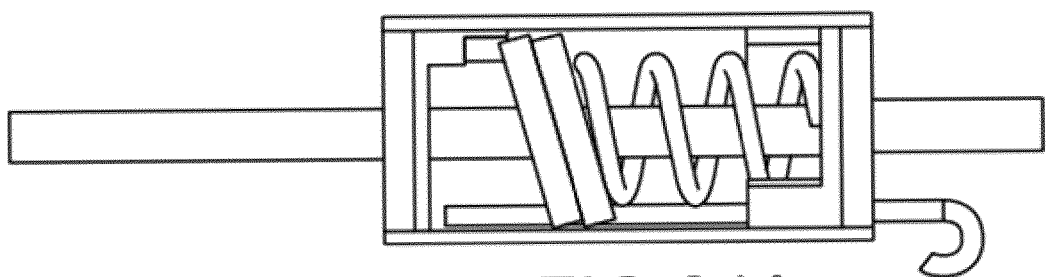
Figure 24B:
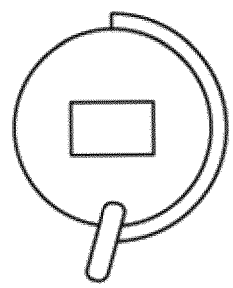

Referring now to FIGS. 23-24B, alternative epicardial anchor structures can be advanced axially through a working lumen (optionally through working lumen of the epicardial hemostasis device described above) and can also be reconfigured between a set-force mode and a variable-force mode through the access lumen. Optionally, reconfiguring of the epicardial anchors may be effected by axial rotation of a rotatable feature with a corresponding feature of a tool extending around the tether (such as the force applying tool described above). Alternatively, a movable actuator may be articulated from along the working lumen.

EXPERIMENTAL

Experiment 1

Implantation in a Pig Cadaver Heart #1

A frozen heart was thawed and placed into expanding foam in a position representative of that in the body seen via a median sternotomy. A variety of baskets were provided for grasping a guide wire passed into the right ventricle across the septum from the left ventricle. The shape of the catheters and baskets varied with target locations along the right ventricular septum that the guide wire would be was to enter.

Figure 25A:
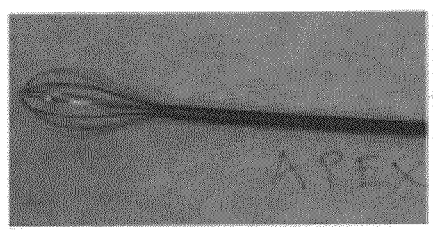
Figure 25B:
Figure 25C:
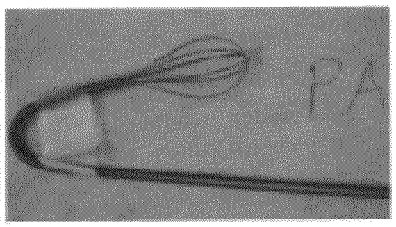

As shown in FIGS. 25a-c, basket configured to retrieve a wire from the apex of the right ventricular septum, from the mid-portion of the right ventricular septum, and from the infundibulum (pulmonary outflow tract) of the right ventricular septum were provided, respectively.

The apex basket was placed into the right ventricle through the opened right atrium and imaged via fluoroscopy. A curved needle was passed through the eipcardial surface of the left ventricle (LV) lateral to the LAD, through the LV cavity, across the ventricular septum and into the right ventricle (RV) in the vicinity of the apical basket.

Figure 26A:
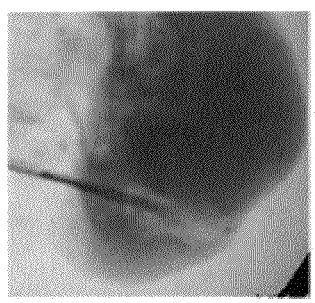
Figure 26B:
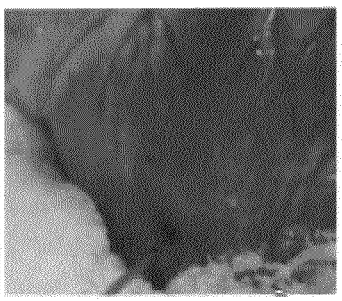
Figure 26C:
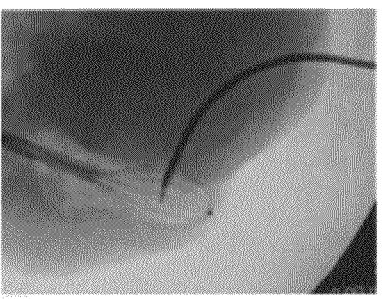
Figure 27A:
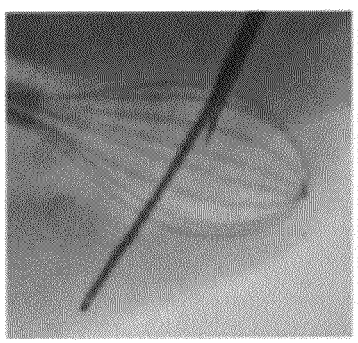
Figure 27B:
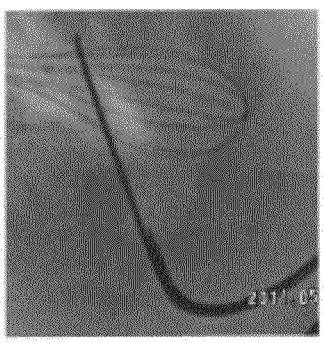
Figure 27C:
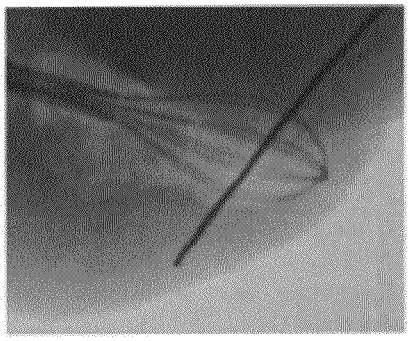

As shown in FIG. 26a the apical basket is placed in the apex of the RV and visualized via fluoroscopy. In FIG. 26b, a needle is passed into the epicardial surface of the L V and in FIG. 26c is aimed toward the basket. Following positioning of the needle, a guide wire is passed through the needle and into the basket via fluoroscopic control. The wire position is confirmed in bi-planar views and the needle is withdrawn. In FIGS. 27a and 27b, the guide wire has been passed through the needle and appeared to be within the basket in bi-planar fluoroscopic views, and in 27c the needle is withdrawn leaving the guide wire in the basket. The guide wire is then grasped by closing the basket into the guiding catheter and pulling, the guide wire along with the catheter and closed basket out of the right atrium (see FIGS. 28a-28c).

Figure 28A:
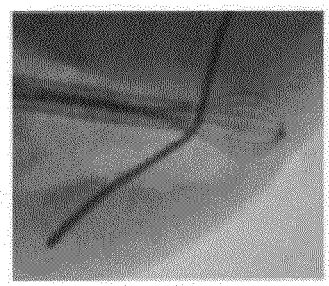
Figure 28B:
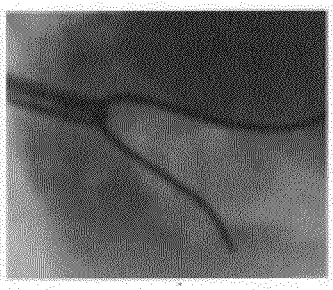
Figure 28C:
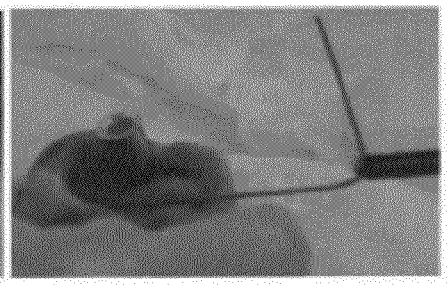

In FIGS. 28a and b, as the guiding sheath is pushed over the basket, the basket grasps the guide wire and pulls it into the catheter. In FIG. 28c the catheter is withdrawn from the right atrium with the attached guide wire.

Figure 28D:
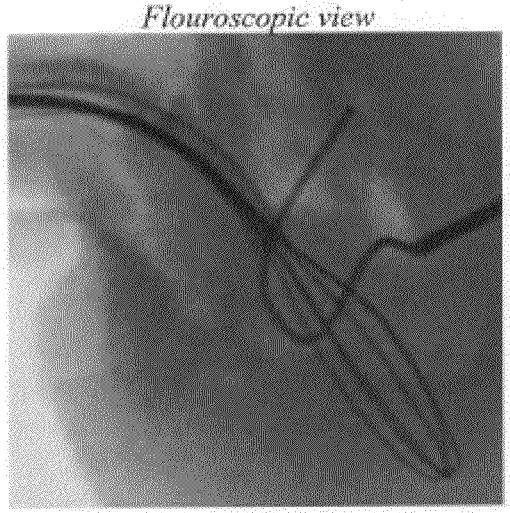
Figure 28E:

This same procedure was then repeated using different baskets and needles to pass and retrieve guide wires from the mid-portion and the infundibular portion of the RV septum. Passing and retrieving a guidewire at the mid-RV septal level is shown in FIGS. 28d and 28e, and passing a retrieving a guide wire at the distal-RV septal (infundibular) level is shown in FIGS. 28f and 28g.

Positioning Anchors

A tethered anchor was passed over a guide wire to position an anchor on the RV septal wall; and passing the tether out the LV epicardial surface to accept an external anchor. The steps were as follows:

A new guide wire is passed through the LV, septum and RV. It was grasped by a basket within a catheter and is withdrawn out of the RA as shown in FIGS. 28h and 28i.

A new, wider support sheath was placed over the guide wire under fluoroscopic control and was seen on the epicardial surface (See FIGS. 28j and 28k).

Through that supporting sheath a dilating catheter is passed through the ventricular septum and following the guide wire out the epicardial surface of the heart. See FIGS. 28i-28n.

While retaining the guide wire within the catheter, the dilator was removed and was replaced by an anchor tether passed retrograde by the tether into the catheter, crossing the septum and exiting the LV epicardium. As the anchor approached the sheath, the guide wire was passed through the alignment hole in the anchor thus aligning the anchor to fit within the hypotube loading cartridge and the sheath. See FIGS. 28o-28s.

Figure 28T:
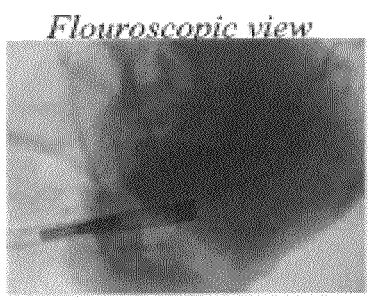
Figure 28U:
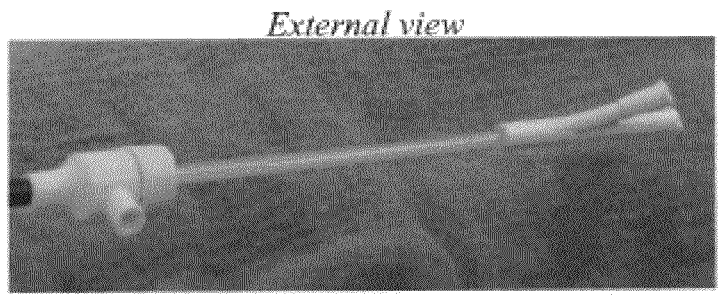
Figure 28V:
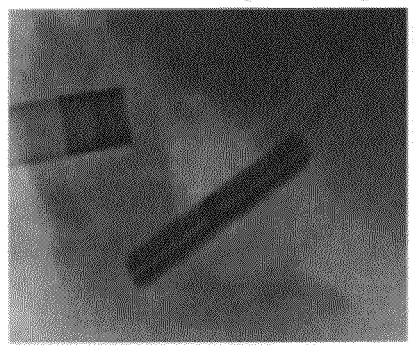
Figure 28W:
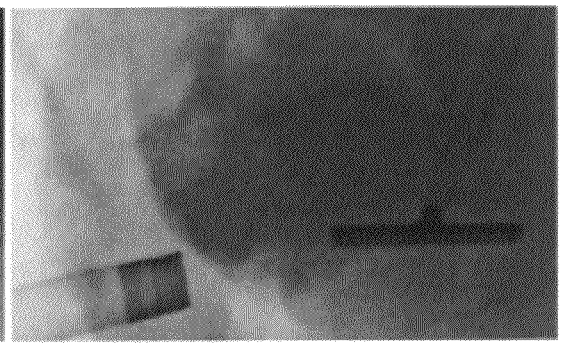

The guide wire and tether are then passed into the pusher. While monitoring the progression of the anchor under fluoroscopy the sheath is maintained near the septum as the anchor is released from the sheath, At this point, the tether is manipulated to refine the anchor alignment. An external anchor is than placed over the tether and slid to the epicardial surface and secured in place. Fluoroscopy confirms correct positioning of the anchor pair. See FIGS. 28t and 28u. In FIGS. 28v and 28w, the anchor has been released from the sheath, aligned and positioned along the RV septum.

A second anchor pair was then placed more apically than the initial pair. The needle was again passed from a more apical position in relation to the first anchor. See FIGS. 28x and 28y. As shown in FIG. 28z, after sheath and dilator placements the anchor was placed in the RV septum and an external anchor secured the anchor pair in place. The final result is shown in FIGS. 28z-28z2.

The heart was opened along the right lateral surface beginning in the right atrium and proceeding across the tricuspid valve with care being taken to preserve the papillary muscles, moderator band, valve tissue and chordai tendini. The position and deployment of the internal anchors were inspected and is shown in FIG. 28z3.

Experiment 2

Implantation in a Human Cadaver Heart 67-year-old male. Cause of death: Heart failure
Serology: NEG
Height: 71 inches; Weight: 237 lbs A frozen heart was thawed, placed into expanding foam in a position representative of that in the body seen via a median sternotomy. A variety of baskets were provided for grasping a guide wire passed into the right ventricle across the septum from the left ventricle, as described above.

The surgical approach was from the right atrium (RA). The basket was placed into the right ventricle through the opened right atrium and imaged via fluoroscopy. A curved needle was then passed through the epicardial surface of the left ventricle (LV) lateral to the LAD, through the LV cavity, across the ventricular septum and into the right ventricle (RV) in the vicinity of the basket. Following positioning of the needle, a guide wire is passed through the needle and into the basket via fluoroscopic control. The wire position is confirmed in bi-planar views and the needle is withdrawn. The guide wire is then grasped by closing the basket into the guiding catheter and pulling the guide wire along with the catheter and closed basket out of the right atrium.

Figure 29A:
Figure 29B:
Figure 29C:

As shown in FIG. 29a, a needle is passed into the epicardial surface of the LV and a guide wire is aimed toward the basket. As shown in FIG. 29b, the basket grasps the guide wire and pulls it into the catheter. As shown in FIG. 29c the catheter is withdrawn from the right atrium with the attached guide wire.

A new 14 Fr. supporting sheath is placed over the guide wire under fluoroscopic control into the RV. Through that supporting sheath a dilating catheter is passed through the ventricular septum and following the guide wire out the epicardial surface of the heart.

While retaining the guide wire within the catheter, the dilator is then removed and is replaced by an anchor tether passed retrograde by the tether into the catheter crossing the septum and exiting the LV epicardium. As the anchor approaches the sheath, the guide wire is passed through the alignment hole in the anchor thus aligning the anchor to fit within the hypotube and the sheath.

The guide wire and tether are then passed into the pusher. While monitoring the progression of the anchor under fluoroscopy the sheath is maintained near the septum as the anchor is released from the sheath. At this point, the guide wire is removed allowing the tether to manipulate and to refine the anchor alignment. An external anchor is then placed over the tether and slid to the epicardial surface and secured in place. Fluoroscopy confirms correct positioning of the anchor pair.

Figure 30A:
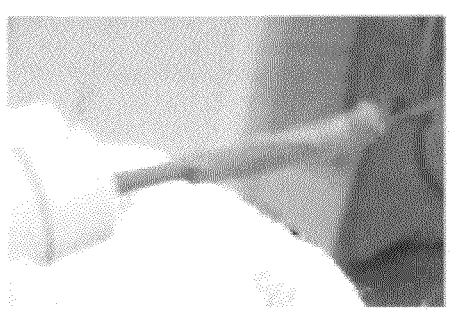
Figure 30B:
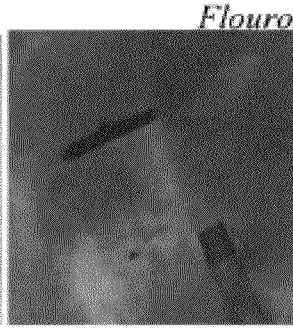
Figure 30C:
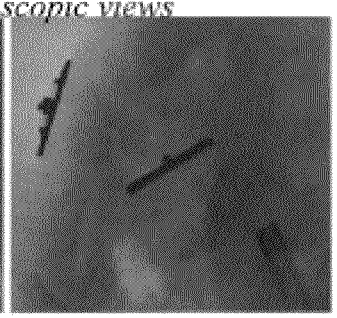

As shown in FIG. 30a, the tether has been passed through the sheath, the guide wire has been passed through the anchor and the anchor is pushed through the sheath into the RV. As shown in FIG. 30b, the anchor has been released from the sheath in the RV. Upon removing the guide wire, the anchor can pivot and is properly aligned along the septum with the tether. As shown in FIG. 30c, the first anchor pair is deployed.

A second anchor pair was then placed more apically than the initial pair. A median basket was passed from the RA into the RV. A needle was passed from a more apical position in relation to the first anchor and a guide wire was passed through the LV, septum and aimed toward the basket in the RV. After bi-planar fluoroscopy confirmed the wire within the basket, it is grasped by the basket within a catheter and is withdrawn out of the RA (see photos below).

As shown in FIG. 31a, the median basket is placed more apical than the first anchor pair. As shown in FIG. 31b, a second guide wire is passed through the LV, across the septum and is (see FIG. 31c) grasped by the basket. As shown in FIG. 31d, the guide wire is brought through the sheath. As shown in FIG. 31e, after the tether is 3 passed retrograde through the sheath and the septal anchor released, (see FIG. 31f) and external anchor is placed. The final view shows alignment of the two anchor pairs.

After sheath and dilator placements the anchor is placed in the RV septum and an external anchor secures the anchor pair in place.

The heart was opened along the right lateral surface beginning in the right atrium and proceeding across the tricuspid valve with care being taken to preserve the papillary muscles, moderator band, valve tissue and chordai tendini. The position and deployment of the two internal anchors were inspected and are shown in FIG. 32a.

Figure 32B:
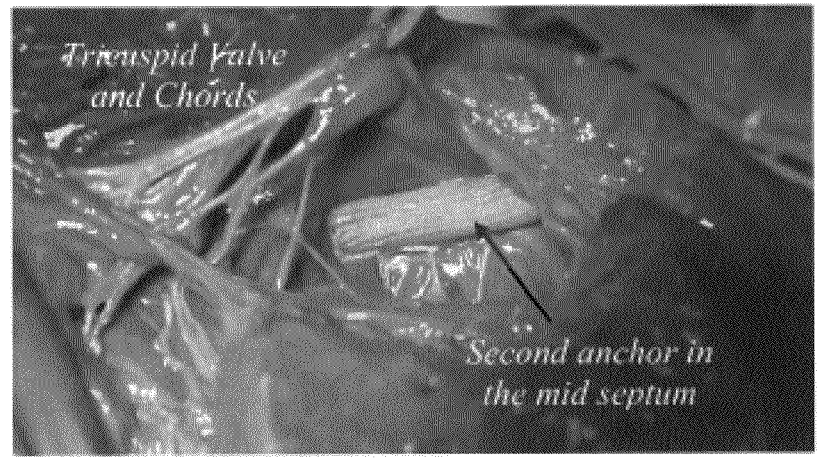
Figure 32C:
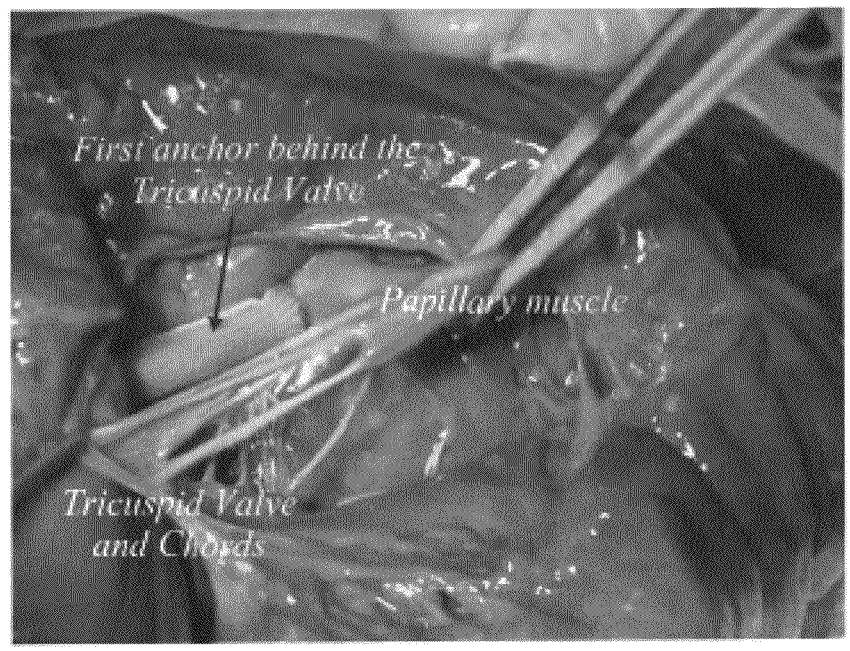

Each right ventricular internal anchor is shown in FIG. 32b or 32c.

Experiment 3

Implantation in a Live Sheep Heart

Weight: 84.7 kg
Age: adult
Sex: male

With the animal under general anesthesia, arterial and venous lines were placed. The chest was opened through a median sternotomy and the pericardium was opened in the midline. A pericardial cradle was created and the right atrial (RA) appendage was exposed. A purse-string suture (4-0 Prolene) was placed on the RA and a 14 Fr. sheath was passed into the right ventricle (RV) through the RA under fluoroscopic guidance.

In FIG. 33a, the heart is exposed through a mid-sternotomy and pericardiotomy. The LAD and apex are labeled, and (see FIG. 33b) a tourniquet is place on the RA. A sheath (blue) is passed and under fluoroscopy and (see FIG. 33c) positioned in the RV (in circle).

An apical basket was passed through the sheath in the RA into the RV, and a needle was passed through the LV epicardium near the apex and aimed toward the basket under fluoroscopic control. A guide wire was passed through the LV and septum and aimed toward the basket in the RV, After bi-planar fluoroacopy confirmed the wire within the basket, it was grasped by the basket within its catheter and was withdrawn out of the RA. A 14 Fr. support sheath was then placed over the guide wire.

Figures 34A, 34B, 34C:
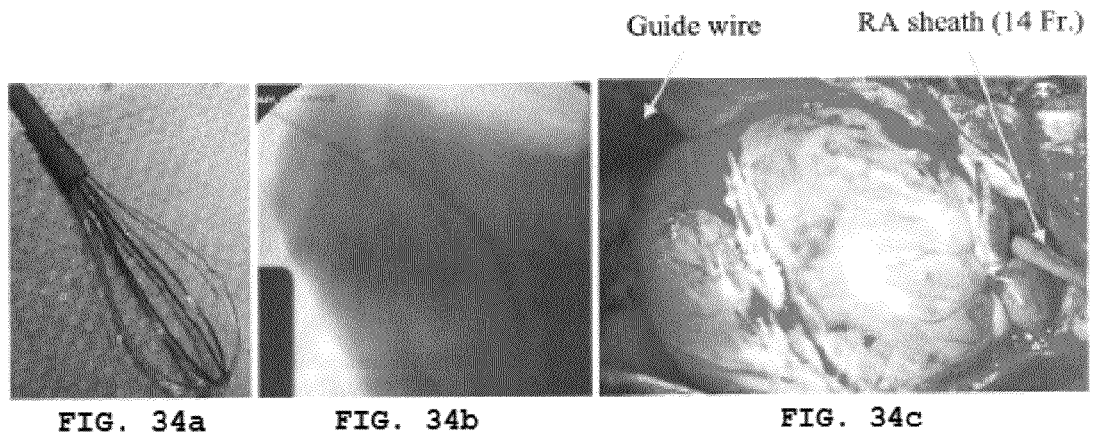

In FIG. 34a, an apical basket was used to place lowest anchor. In FIG. 34b, the guide wire was grasped by the basket and drawn through the RA sheath. In FIG. 34c, the external appearance of the RA sheath with the guide wire exiting the L V epicardium is shown.

Under fluoroscopic control, through the sheath, a dilating catheter was passed through the ventricular septum and, following the guide wire, out the epicardial surface of LV of the heart, No bleeding was noted from either the entry or exit points of the catheter and no blood entered the catheter.

While retaining the guide wire within the catheter, the dilator was then removed and replaced by an anchor tether passed retrograde at the tether end into the catheter, crossing the septum and exiting the LV epicardium. As the anchor approached the sheath, the guide wire was passed through the alignment hole in the anchor thus aligning the anchor to fit within the hypotube and the sheath.

Figures 35A, 35B, 35C:
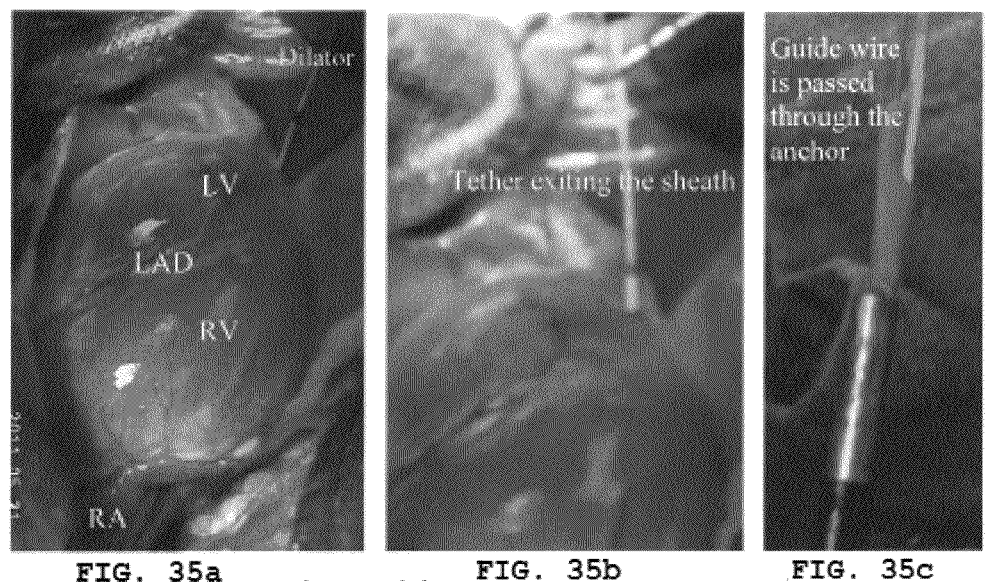

In FIG. 35a, the dilating catheter was passed through the sheath and follows the guide wire across the ventricular septum and exits on the epicardial surface of LV. In FIG. 35b, the dilator was removed and an anchor tether was passed through the sheath, The end of the tether exits on the epicardial surface. In FIG. 35c, as the anchor approaches the sheath, the guide wire is placed through the hole in the anchor for alignment and entry into the sheath.

The guide wire and tether were passed into the pusher. While monitoring the progression of the anchor under fluoroscopy the sheath was maintained near the septum as the anchor was released from the sheath. At this point, the tether was manipulated to refine the anchor alignment. An external anchor was then placed over the tether and slid to the epicardial surface and secured in place. Fluoroscopy confirmed correct positioning of the anchor pair, In FIG. 36a, the anchor within the hypotube is being placed into the sheath. In FIG. 36b, after the guide wire was removed, the anchor was released and manipulated into proper alignment. In FIG. 36c, an external anchor was placed on the tether and secured in place on the epicardium.

Following placement of the first anchor pair, the process was repeated for placing a second anchor pair in the midportion of the septum. A lasso type basket snare was used to capture the guidewire. Following this the second wire was captured as it was passed into the RV. FIGS. 37a-37f show the sequence of events for placement of the second anchor pair: (a) the guide wire is captured by the "lasso' snare and (b) brought out the RA sheath. (c) Shows the guide wire entry site into the LV. (d) A dilator was passed through the sheath over the guide wire and exits the LV (note the absence of bleeding). The anchor tether was passed through the sheath and with the pusher, the anchor was pushed through the sheath. (e) After removing the guide wire, the tether was manipulated to refine the anchor alignment under fluoroscopy. (f) An external anchor was then placed over the tether and slid to the epicardial surface and secured in place.

A third set of anchor pairs was then placed more toward the heart base (RV infundibulum). The same "lasso" snare was used for the second anchor pair and grasped the guide wire near the pulmonary outflow tract. The animal was then sacrificed. FIGS. 38a-39b show the final anchor positions in situ and following sacrifice and heart explantation.

Figure 39A:
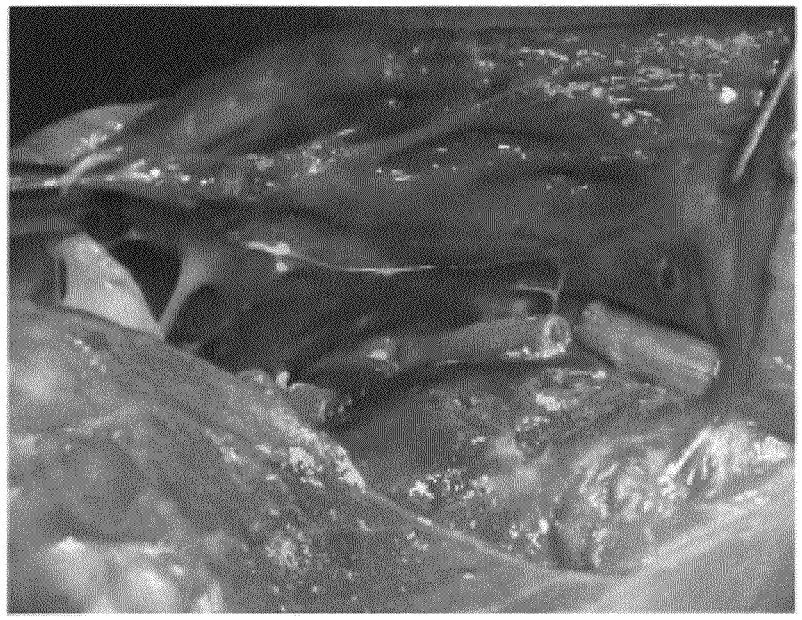

Following sacrifice, The heart was then opened along the right lateral surface beginning in the right atrium and proceeding across the tricuspid valve with care being taken to preserve the papillary muscles, moderator band, valve tissue and chordai tendini, The position and deployment of the internal anchors were inspected and are shown in FIG. 39a.

Figure 39B:

The left ventricle was opened to expose the septal surface, The line of tissue exclusion can be seen between the dashed lines of FIG. 39b. The exclusion line is smooth and complete.

While the exemplary embodiments have been described in some detail for clarity of understanding and by way of example, a variety of modification, adaptations, and changes will be obvious to those of skill in the art. Hence, the scope of the present invention is limited solely by the appended claims.

What is claimed is:

1. A system for treating a heart within a patient, the heart having first and second chambers with a septum therebetween, the second chamber having an exterior wall, the system comprising:
   a first elongate shaft having a proximal end and a distal end, the distal end of the first shaft being configured to be advanced from outside the patient into the heart along a first path so that the distal end of the first shaft is disposed in the first chamber;

a second elongate shaft having a proximal end and a distal end, the distal end of the second shaft being configured to be advanced along a second path from outside the heart, through the exterior wall and through the septum so that the distal end of the second shaft is disposed in the first chamber;

a first elongate flexible body slidably coupled to one of the shafts, the first flexible body having a distal end portion configured for in situ coupling, within the first chamber of the heart, with a corresponding distal end portion extending from the other of the shafts so as to join the first path with the second path;

an implant configured to be advanced along the joined paths, the implant including:
- a first anchor having a low profile configuration for advancement of the first anchor along the joined paths;
- a second anchor; and
- an elongate tension member having a first end couplable with the first anchor and a second end couplable with the second anchor, the first anchor configured to deploy laterally from the low-profile configuration within the first chamber, the tension member configured to extend from the first anchor in the first chamber, through the septum, through the second chamber, and through the exterior wall such that applying tension between the anchors with the tension member urges the septum and the external wall to engage.

2. The system of claim 1, wherein the first elongate flexible body is axially advanceable along the first shaft so that the end portion of the first elongate flexible body is disposed in the first chamber, and further comprising a second flexible body advanceable along the second shaft so that an end portion of the second flexible body is disposed in the first chamber, the end portion of the second flexible body comprising the corresponding end portion.

3. The system of claim 2, wherein the end portion of the first elongate flexible body has an opening configured for capturing the end portions of the second flexible body therein.

4. The system of claim 1, wherein the end portion of the first elongate flexible body comprises a snare, the snare biased to expand from a low profile configuration when released in the first chamber of the heart so as to expand the opening.

5. The system of claim 4, wherein the snare comprises a basket snare configured to expand by releasing the basket snare from a lumen of the first or second shaft so that the basket snare expands from a low profile insertion configuration to an expanded configuration encompassing a volume of the first chamber of the heart.

6. The system of claim 4, wherein the first or second shaft has a lumen, the snare configured to capture the corresponding end portion by withdrawing the snare into the lumen when the corresponding end portion extends through the lumen.

7. The system of claim 6, wherein the lumen extends along the second shaft, and wherein the corresponding end portion comprises a distal length of the tension member so that the tension member and first anchor are configured to be advanced to the first chamber along the first path by pulling the second end of the tension member with the first elongate flexible body through the septum and through the external wall.

8. The system of claim 6, wherein the corresponding end portion comprises a length of a guidewire, the guidewire having first and second opposed ends and configured so that the guidewire can extend from the first end portion outside the patient, into the first chamber along the first path, and through the septum, through the second chamber, through the external wall, and out of the patient to the opposed end along the second path.

9. The system of claim 1, wherein the second shaft comprises an at least semi-rigid curved needle, the curved needle having a sharp tissue penetrating tip at the distal end of the second shaft and a lumen extending axially toward the tip, the curved needle configured for forming the second path through the external wall and the septum.

10. The system of claim 1, further comprising an access tool configured for accessing the first chamber so as to define at least one of the first or second path, and a guide body advanceable from outside the patient to the first chamber along the access tool, the distal end of at least one of the first or second elongate bodies configured to be advanced to the first chamber using the guide body.

11. The system of claim 1, further comprising an axial force-application tool configured for applying a desired anchor migration inhibiting force between the anchors; wherein the second anchor has a variable force mode configured to allow axial sliding of the anchor along the tension member toward the first anchor and away from the first anchor, wherein the second anchor has a set-force mode configured to inhibit sliding of the anchor away from the first anchor, and wherein the anchor is configured for changing from the variable-force mode to the set-force mode while the axial force-application tool applies the desired anchor force between the tension member and the second anchor.

12. The system of claim 1, wherein the first elongate shaft comprises a flexible coronary catheter and the distal end of the first elongate shaft is configured to be advanced to the right ventricle through the right atrium and blood vessels in fluid communication therewith.

13. The system of claim 1, wherein the first elongate shaft comprises an at least semi-rigid shaft and the distal end of the first elongate shaft comprises a tissue-penetrating tip configured to be advanced to the right ventricle through a right atrial appendage of the heart.

14. The system of claim 1, wherein the tension member and the first anchor are configured to be advanced into the first chamber of the heart along the first path with the tension member advanced from the first chamber along the second path by pulling an end of the tension member along the second path through the second chamber so that the end of the tension member extends outside the heart.

15. The system of claim 1, wherein the tension member and the first anchor are configured to be advanced into the heart along the second path with the tension member trailing from the advancing first anchor so as to extend through the second chamber when the first anchor reaches the first chamber.

16. A system for treating a heart within a patient, the heart having a chamber border by a plurality of walls, the system comprising
- a first insertion device having a proximal end and a distal end, the distal end of the first insertion device being configured to be advanced from outside the patient into the heart along a first path so that the distal end of the first insertion device is disposed in the chamber;
- a second insertion device having a proximal end and a distal end, the distal end of the second insertion device being configured to be advanced along a second path from outside the heart so that the distal end of the second insertion device is disposed in the chamber;
- an elongate flexible body slidably coupled to one of the insertion devices, the elongate flexible body having a coupling member for in situ coupling, within the chamber of the heart, with a distal end portion extending from the other insertion device so as to join the first path with the second path;
an implant configured to be advanced along the joined paths, the implant including:
  a first anchor having a low profile configuration for advancement of the first anchor along the joined paths;
  a second anchor; and
  an elongate tension member having a first end coupled with the first anchor and a second end coupleable with the second anchor, the first anchor configured to deploy laterally from the low-profile configuration within the chamber, the tension member configured to extend from the first anchor in the chamber and through a first wall of the heart such that applying tension between the anchors with the tension member urges the first wall to engage with a second wall of the heart.

17. The system of claim 16, wherein the elongate flexible body is axially advanceable along the first insertion device so that the end portion of the elongate flexible body is disposed in the chamber, and further comprising a guidewire that is advanceable along the second insertion device so that an end portion of the guidewire is disposed in the chamber, the end portion of the guidewire comprising the distal end portion that extends from the other distal end portion extending.

18. The system of claim 16, wherein the coupling member of the elongate flexible body comprises a snare, wherein the snare is biased to expand from a low profile configuration when released in the chamber of the heart.

19. The system of claim 18, wherein the first or second insertion device has a lumen, and wherein the snare is configured to capture the distal end portion that extends from the other insertion device by drawing the snare into the lumen.

20. The system of claim 19, wherein the lumen extends along the second insertion device, and wherein the distal end portion that extends from the other insertion device is a distal length of the tension member, wherein the tension member and first anchor are configured to be advanced to the chamber along the first path by pulling the second end of the tension member with the elongate flexible body through the first wall and second wall of the heart.

21. The system of claim 19, wherein the distal end portion that extends from the other insertion device is a length of a guidewire, the guidewire having first and second opposed ends and being configured so that the guidewire is extendable from outside the patient, into the chamber along the first path, through the first and second walls of the heart, and outside the patient along the second path.

22. The system of claim 16, wherein the second insertion device comprises a semi-rigid curved needle, the curved needle having a sharp tissue penetrating tip at the distal end and a lumen extending axially toward the distal end, the curved needle configured for forming the second path through the first wall of the heart.

23. The system of claim 16, further comprising an axial force-application tool configured for applying a desired anchor migration inhibiting force between the anchors; wherein the second anchor has a variable force mode configured to allow axial sliding of the anchor along the tension member toward the first anchor and away from the first anchor, wherein the second anchor has a set-force mode configured to inhibit sliding of the anchor away from the first anchor, and wherein the anchor is configured for changing from the variable-force mode to the set-force mode while the axial force-application tool applies the desired anchor force between the tension member and the second anchor.

* * * * *